(12) United States Patent
Zhong et al.

(10) Patent No.: US 10,086,030 B2
(45) Date of Patent: *Oct. 2, 2018

(54) USE OF COMPOSITION IN PREPARING HEALTH CARE PRODUCTS OR MEDICINES FOR PREVENTING AND TREATING ALLERGIC DISEASES

(71) Applicant: JIANGZHONG PHARMACEUTICAL CO., LTD., Nanchang, Jiangxi (CN)

(72) Inventors: Hongguang Zhong, Nanchang (CN); Minzhi Yi, Nanchang (CN); Jianzhong Lu, Nanchang (CN)

(73) Assignee: Jiangzhong Pharmaceutical Co., Ltd., Nanchang (CN)

( * ) Notice: Subject to any disclaimer, the term of this patent is extended or adjusted under 35 U.S.C. 154(b) by 689 days.

This patent is subject to a terminal disclaimer.

(21) Appl. No.: 14/403,986

(22) PCT Filed: May 27, 2013

(86) PCT No.: PCT/CN2013/000619
§ 371 (c)(1),
(2) Date: Nov. 25, 2014

(87) PCT Pub. No.: WO2013/177944
PCT Pub. Date: Dec. 5, 2013

(65) Prior Publication Data
US 2015/0147351 A1 May 28, 2015

(30) Foreign Application Priority Data
May 29, 2012 (CN) .......................... 2012 1 0169736

(51) Int. Cl.
| | | |
|---|---|---|
| *A61K 36/738* | (2006.01) | |
| *A61K 9/08* | (2006.01) | |
| *A61K 36/068* | (2006.01) | |
| *A61K 36/074* | (2006.01) | |
| *A61K 36/258* | (2006.01) | |
| *A61K 36/344* | (2006.01) | |
| *A61K 36/36* | (2006.01) | |
| *A61K 36/481* | (2006.01) | |
| *A61K 9/00* | (2006.01) | |
| *A61K 36/73* | (2006.01) | |
| *A61K 36/062* | (2006.01) | |
| *A61K 9/14* | (2006.01) | |
| *A61K 9/16* | (2006.01) | |
| *A61K 9/20* | (2006.01) | |
| *A61K 9/48* | (2006.01) | |

(52) U.S. Cl.
CPC .......... *A61K 36/738* (2013.01); *A61K 9/0053* (2013.01); *A61K 9/08* (2013.01); *A61K 36/062* (2013.01); *A61K 36/068* (2013.01); *A61K 36/074* (2013.01); *A61K 36/258* (2013.01); *A61K 36/344* (2013.01); *A61K 36/36* (2013.01); *A61K 36/481* (2013.01); *A61K 36/73* (2013.01); *A61K 9/0056* (2013.01); *A61K 9/0095* (2013.01); *A61K 9/141* (2013.01); *A61K 9/1605* (2013.01); *A61K 9/2004* (2013.01); *A61K 9/4841* (2013.01); *A61K 2236/39* (2013.01)

(58) Field of Classification Search
CPC .................................................... A61K 36/738
See application file for complete search history.

(56) References Cited

U.S. PATENT DOCUMENTS

| | | | | |
|---|---|---|---|---|
| 8,986,750 B2 * | 3/2015 | Zhong | ................... | A61K 36/068 |
| | | | | 424/725 |
| 9,775,868 B2 * | 10/2017 | Zhong | ................... | A61K 36/258 |

FOREIGN PATENT DOCUMENTS

| | | |
|---|---|---|
| AU | 2007100050 | 2/2007 |
| AU | 2007100050 A4 * | 2/2007 |
| CN | 1225262 A | 8/1999 |
| CN | 1333054 A * | 1/2002 |
| CN | 1387911 A | 1/2003 |
| CN | 1539440 A | 10/2004 |
| CN | 101292742 A | 10/2008 |
| CN | 102000129 A | 4/2011 |
| CN | 102205005 A | 10/2011 |
| CN | 102228252 A | 11/2011 |
| CN | 102274258 | 12/2011 |
| CN | 102274258 A | 12/2011 |
| CN | 102274259 A | 12/2011 |

(Continued)

OTHER PUBLICATIONS

Second Office Action dated Jul. 4, 2016 for counterpart Chinese patent application No. 201210169736.2, along with the English translation; 7 pages.

(Continued)

*Primary Examiner* — Susan Hoffman
(74) *Attorney, Agent, or Firm* — Loza & Loza, LLP; Michael Fedrick

(57) ABSTRACT

The present invention relates to use of a composition in the manufacture of health care products or medicaments for prevention and treatment of allergic diseases. The composition is made from raw materials comprising 5 to 200 parts by weight of Ganoderma, 5 to 150 parts by weight of Radix Panacis Quinquefolii or Radix Et Rhizoma Ginseng, 1 to 90 parts by weight of fermented *Cordyceps sinensis* powder and/or 1 to 120 parts by weight of Cordyceps, or is a composition made from water and/or alcohol extracts of the above raw materials as active components. The allergic diseases include allergic rhinitis, allergic dermatitis, urticaria, and/or allergic asthma.

18 Claims, No Drawings

(56) References Cited

FOREIGN PATENT DOCUMENTS

| CN | 102697868 A | 10/2012 |
| KR | 2009116813 A | 11/2009 |
| WO | WO 2012/034534 A * | 3/2012 |

OTHER PUBLICATIONS

First office action dated Nov. 6, 2015 for counterpart Chinese Patent Application No. 201210169736.2.
Search report dated Nov. 6, 2015 for counterpart Chinese Patent Application No. 201210169736.2.
Dictionary of Chinese Medicine, Shanghai Science and Technology Press, pp. 38-45,1055-1058, and 1649-1653 (2006).
Database WPI Week 200334 Thomson Scientific,London,GB;AN 2003-355393; XP002745339; 1 page.
Database WPI Week 199950 Thomson Scientific,London,GB;AN 1999-581054; XP002745340; 1 page.
Extended European Search Report for 13796431.8 dated Oct. 23, 2015; 7 pages.
Ponomariov, V.D. Ekstragirovanie lekarstvennogo syrya [Extraction of drug raw materials], Moscow, Medicina, pp. 115-120 (1976).
Office Action dated Nov. 3, 2016, Russian Patent Application No. 2014151157.
Feng et al., "Affection on IgE, IL-5Rαand HLA-A of Juvenile Asthma During Recovery Stage with Compound Chinese Drug Prescription for Tonification", Journal of Nanjing TCM University, vol. 24, No. 5, Sep. 2008; 4 pages.
Fan, Wenyu, (2010) A brief review of pharmacological action of traditional Chiense drug Radix Et Rhizoma Ginseng and its applications, Xinjiang Journal of Traditional Chinese Medicine, vol. 28, Issue 4, pp. 89-92.
Li, Jinning. and Lei, Cailan, (2006), Tiaoyuan anti-allergy tablet in combination with Western medicine for treatment of allergic rhinitis: observation of 70 cases for efficacy, Traditional Chinese Medicine Journal, vol. 5, Issue 2, pp. 48-50.
RU Patent Appln. No. 2014151157. (3rd Office Action, dated Jun. 20, 2017).
EP Patent Application No. 13796431.8. (1st Office Action, dated Jun. 28, 2017).
Sun et al. "Effects of Cordyceps extract on cytokines and transcription factors in peripheral blood mononuclear cells of asthmatic children during remission stage." Zhong Xi Yi Jie He Xue Bao (4): 341-6 (Apr. 8, 2010).
Jeon et al. "Anti-allergic effects of white rose petal extract and anti-atopic properties of its hexane fraction." Arch Pharm Res. 32(6):823-30 (Jun. 2009).
Andoh et al. "Inhibitory effects of the methanol extract of Ganoderma lucidum on mosquito allergy-induced itch-associated responses in mice." J Pharmacol Sci. 114(3):292-7 (2010).
Sumiyoshi et al. "Effects of red ginseng extract on allergic reactions to food in Balb/c mice." J Ethnopharmacol.132(1): 206-12 (Oct. 28, 2010).
Chinese Patent Application No. 2012101697362. Supp. Search Report (dated Sep. 14, 2017).

* cited by examiner

USE OF COMPOSITION IN PREPARING HEALTH CARE PRODUCTS OR MEDICINES FOR PREVENTING AND TREATING ALLERGIC DISEASES

CROSS-REFERENCE TO RELATED APPLICATIONS

This application is the U.S. national stage of International Patent Application No. PCT/CN2013/000619, filed on May 27, 2013 and entitled USE OF COMPOSITION IN PREPARING HEALTH CARE PRODUCTS OR MEDICINES FOR PREVENTING AND TREATING ALLERGIC DISEASES, which claims the benefit of priority under 35 U.S.C. § 119 from Chinese Patent Application No. 201210169736.2, filed May 29, 2012. The disclosures of the foregoing applications are incorporated herein by reference in their entirety.

TECHNICAL FIELD

The present invention relates to a composition for prevention and treatment of allergic diseases and use thereof.

BACKGROUND ART

Patent application CN1509760A discloses a medicament for prevention and adjunctive treatment of cancer made from the raw materials fermented *Cordyceps sinensis* powder, Ganoderma and Fructus Lycii, which functions to enhance immunity and regulate endocrine and also plays a role in cleaning detrimental free radicals in the body and preventing recurrence of tumor. Patent application CN102228252A discloses a composition of traditional Chinese medicine comprising 5 to 150 parts by weight of Radix Panacis Quinquefolii or Radix Et Rhizoma Ginseng, 5 to 160 parts by weight of Ganoderma and 1 to 90 parts by weight of fermented *Cordyceps sinensis* powder, which functions to alleviate physical fatigue. Patent Application CN102000129A discloses a pharmaceutical composition comprising Cordyceps polysaccharides or fermented *Cordyceps sinensis* powder, Ganoderma and Radix Panacis Quinquefolii, which functions to enhance immunity. Up till now, no report or literature has shown that a composition made from Ganoderma, Radix Panacis Quinquefolii or Radix Et Rhizoma Ginseng, fermented *Cordyceps sinensis* powder and/or Cordyceps which functions to prevent and treat allergic diseases.

SUMMARY OF THE INVENTION

The objective of the present invention is to provide a composition for prevention and treatment of allergic diseases and the preparation method thereof.

In accordance with the present invention, we select and combine raw materials Ganoderma, Radix Panacis Quinquefolii or Radix Et Rhizoma Ginseng, fermented *Cordyceps sinensis* powder and/or Cordyceps, and we surprisingly found that such a composition or products made therefrom were capable of preventing and treating allergic diseases.

The present invention provides use of a composition comprising Ganoderma, Radix Panacis Quinquefolii or Radix Et Rhizoma Ginseng, fermented *Cordyceps sinensis* powder and/or Cordyceps, a composition made from raw materials comprising Ganoderma, Radix Panacis Quinquefolii or Radix Et Rhizoma Ginseng, fermented *Cordyceps sinensis* powder and/or Cordyceps, or a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic diseases.

Provided is use of a composition prepared by adding any one or more components of Flos Rosae Rugosae, Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, or to a composition made from raw materials comprising Ganoderma, Radix Panacis Quinquefolii or Radix Et Rhizoma Ginseng, fermented *Cordyceps sinensis* powder and/or Cordyceps, or to a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic diseases.

The present invention further provides use of a composition comprising Ganoderma, Radix Panacis Quinquefolii or Radix Et Rhizoma Ginseng, fermented *Cordyceps sinensis* powder and/or Cordyceps, and Flos Rosae Rugosae, a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic diseases.

Provided is use of a composition prepared by adding any one or more components of Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic diseases.

The present invention further provides use of a composition comprising Ganoderma, Radix Panacis Quinquefolii or Radix Et Rhizoma Ginseng, fermented *Cordyceps sinensis* powder and/or Cordyceps, a composition made from raw materials comprising Ganoderma, Radix Panacis Quinquefolii or Radix Et Rhizoma Ginseng, fermented *Cordyceps sinensis* powder and/or Cordyceps, or a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic rhinitis.

Provided is use of a composition prepared by adding any one or more components of Flos Rosae Rugosae, Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, or to a composition made from raw materials comprising Ganoderma, Radix Panacis Quinquefolii or Radix Et Rhizoma Ginseng, fermented *Cordyceps sinensis* powder and/or Cordyceps, or to a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic rhinitis.

Provided is use of a composition comprising Ganoderma, Radix Panacis Quinquefolii or Radix Et Rhizoma Ginseng, fermented *Cordyceps sinensis* powder and/or Cordyceps, and Flos Rosae Rugosae, a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic rhinitis.

Provided is use of a composition prepared by adding any one or more components of Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic rhinitis.

The present invention further provides use of a composition comprising Ganoderma, Radix Panacis Quinquefolii or Radix Et Rhizoma Ginseng, fermented *Cordyceps sinensis* powder and/or Cordyceps, a composition made from raw materials comprising Ganoderma, Radix Panacis Quinquefolii or Radix Et Rhizoma Ginseng, fermented *Cordyceps sinensis* powder and/or Cordyceps, or a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic dermatitis.

Provided is use of a composition prepared by adding any one or more components of Flos Rosae Rugosae, Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, or to a composition made from raw materials comprising Ganoderma, Radix Panacis Quinquefolii or Radix Et Rhizoma Ginseng, fermented *Cordyceps sinensis* powder and/or Cordyceps, or to a composition made from Ganoderma, Radix Panacis Quinquefolii or Radix Et Rhizoma Ginseng, fermented Cordyceps sinensis powder and/or Cordyceps, in the manufacture of health care products, medicaments, or products for preventing and treating allergic dermatitis.

Provided is use of a composition comprising Ganoderma, Radix Panacis Quinquefolii or Radix Et Rhizoma Ginseng, fermented *Cordyceps sinensis* powder and/or Cordyceps, and Flos Rosae Rugosae, a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic dermatitis.

Provided is use of a composition prepared by adding any one or more components of Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic dermatitis.

The present invention further provides use of a composition comprising Ganoderma, Radix Panacis Quinquefolii or Radix Et Rhizoma Ginseng, fermented *Cordyceps sinensis* powder and/or Cordyceps, a composition made from raw materials comprising Ganoderma, Radix Panacis Quinquefolii or Radix Et Rhizoma Ginseng, fermented *Cordyceps sinensis* powder and/or Cordyceps, or a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating urticaria.

Provided is use of a composition prepared by adding any one or more components of Flos Rosae Rugosae, Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, or to a composition made from raw materials comprising Ganoderma, Radix Panacis Quinquefolii or Radix Et Rhizoma Ginseng, fermented *Cordyceps sinensis* powder and/or Cordyceps, or to a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating urticaria.

Provided is use of a composition comprising Ganoderma, Radix Panacis Quinquefolii or Radix Et Rhizoma Ginseng, fermented *Cordyceps sinensis* powder and/or Cordyceps, and Flos Rosae Rugosae, a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating urticaria.

Provided is use of a composition prepared by adding any one or more components of Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating urticaria.

The present invention further provides use of a composition comprising Ganoderma, Radix Panacis Quinquefolii or Radix Et Rhizoma Ginseng, fermented *Cordyceps sinensis* powder and/or Cordyceps, a composition made from raw materials comprising Ganoderma, Radix Panacis Quinquefolii or Radix Et Rhizoma Ginseng, fermented *Cordyceps sinensis* powder and/or Cordyceps, or a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic asthma.

Provided is use of a composition prepared by adding any one or more components of Flos Rosae Rugosae, Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, or to a composition made from raw materials comprising Ganoderma, Radix Panacis Quinquefolii or Radix Et Rhizoma Ginseng, fermented *Cordyceps sinensis* powder and/or Cordyceps, or to a composition made from Ganoderma, Radix Panacis Quinquefolii or Radix Et Rhizoma Ginseng, fermented *Cordyceps sinensis* powder and/or Cordyceps, in the manufacture of health care products, medicaments, or products for preventing and treating allergic asthma.

Provided is use of a composition comprising Ganoderma, Radix Panacis Quinquefolii or Radix Et Rhizoma Ginseng, fermented *Cordyceps sinensis* powder and/or Cordyceps, and Flos Rosae Rugosae, a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic asthma.

Provided is use of a composition prepared by adding any one or more components of Ganoderma spore powder, Ganoderma spore oil, Radix Pseudostellariae, Folium Ginseng, Radix Codonopsis, and Radix Astragali to a composition comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from raw materials comprising Ganoderma, Radix Panacis Quinquefolii or Radix Et Rhizoma Ginseng, fermented *Cordyceps sinensis* powder and/or Cordyceps, and Flos Rosae Rugosae, or to a composition made from Ganoderma, Radix Panacis Quinquefolii or Radix Et Rhizoma Ginseng, fermented *Cordyceps sinensis* powder and/or Cordyceps, and Flos Rosae Rugosae, in the manufacture of health care products, medicaments, or products for preventing and treating allergic asthma.

The term "products" in the "health care products, medicaments, or products" mentioned above include those not encompassed in "health care products" or "medicaments", including any articles using the composition according to the present invention, for example, essential oils, incense products, and pillows.

Preferably, the composition for use according to the present invention for prevention and treatment of allergic diseases is made from the following raw materials in parts by weight: 5 to 200 parts of Ganoderma, 5 to 150 parts of Radix Panacis Quinquefolii or Radix Et Rhizoma Ginseng, 1 to 90 parts of fermented *Cordyceps sinensis* powder and/or 1 to 120 parts of Cordyceps.

Preferred are 20 to 120 parts of Ganoderma, 10 to 90 parts of Radix Panacis Quinquefolii or Radix Et Rhizoma Ginseng, 3 to 60 parts of fermented *Cordyceps sinensis* powder and/or 3 to 90 parts of *Cordyceps*.

More preferred are 40 parts of Ganoderma, 30 parts of Radix Panacis Quinquefolii or Radix Et Rhizoma Ginseng, 20 parts of fermented *Cordyceps sinensis* powder and/or 6.7 parts of *Cordyceps*.

The composition for use according to the present invention may further comprise the following additional materials that do not compromise the efficacy of the present invention, or water and/or alcohol extracts of these additional materials, in parts by weight: one or more of 5 to 90 parts of Flos Rosae Rugosae, 5 to 150 parts of Ganoderma spore powder, 1 to 90 parts of Ganoderma spore oil, 10 to 400 parts of Radix Pseudostellariae, 1 to 120 parts of Folium Ginseng, 3 to 400 parts of Radix Codonopsis and 3 to 400 parts of Radix Astragali, or any combination thereof.

Preferred are one or more of 10 to 60 parts of Flos Rosae Rugosae, 10 to 120 parts of Ganoderma spore powder, 10 to 60 parts of Ganoderma spore oil, 20 to 200 parts of Radix Pseudostellariae, 20 to 90 parts of Folium Ginseng, 20 to 200 parts of Radix Codonopsis and 20 to 200 parts of Radix Astragali, or any combination thereof.

More preferred are one or more of 30 parts of Flos Rosae Rugosae, 30 parts of Ganoderma spore powder, 20 parts of Ganoderma spore oil, 40 parts of Radix Pseudostellariae, 30 parts of Folium Ginseng, 40 parts of Radix Codonopsis and 40 parts of Radix Astragali, or any combination thereof.

Preferably, the composition for use according to the present invention is a composition of 5 to 200 parts of Ganoderma, 5 to 150 parts of Radix Panacis Quinquefolii or Radix Et Rhizoma Ginseng, 1 to 90 parts of fermented *Cordyceps sinensis* powder and/or 1 to 120 parts of Cordyceps, and 5 to 90 parts of Flos Rosae Rugosae.

More preferred are 20 to 120 parts of Ganoderma, 10 to 90 parts of Radix Panacis Quinquefolii or Radix Et Rhizoma Ginseng, 3 to 60 parts of fermented *Cordyceps sinensis* powder and/or 3 to 90 parts of Cordyceps, and 10 to 60 parts of Flos Rosae Rugosae.

More preferred are 40 parts of Ganoderma, 30 parts of Radix Panacis Quinquefolii or Radix Et Rhizoma Ginseng, 20 parts of fermented *Cordyceps sinensis* powder and/or 6.7 parts of Cordyceps, and 30 parts of Flos Rosae Rugosae.

In accordance with the present invention, Folium Ginseng, Radix Pseudostellariae, Radix Codonopsis, and/or Radix Astragali may be used instead of Radix Panacis Quinquefolii or Radix Et Rhizoma Ginseng.

In another aspect of the present invention, the compositions as mentioned above are provided.

The term "Ganoderma", as used herein, refers to the dry sporocarp of fungal species *Ganoderma lucidum* (Leyss.ex Fr.) Karst. or *Ganoderma sinense* Zhao, Xu et Zhang of the family Polyporaceae. It has a sweet taste and a plain nature, is involved in the heart, lung, liver and kidney channels, and has the effects of nourishing physical strength and calming and tranquilizing the mind. The term "Radix Et Rhizoma Ginseng", as used herein, refers to the dry root and rootstock of the plant species *Panax ginseng* C. A. Mey. of the family Araliaceae. It may be various types of ginseng, such as garden ginseng, wild ginseng, dried fresh ginseng, dried fresh wild ginseng, sugar-processed ginseng, and red ginseng. The term "Folium Ginseng" refers to the dry leaves of the plant species *Panax ginseng* C. A. Mey. of the family Araliaceae. The term "Radix Panacis Quinquefolii", as used herein, also known as American ginseng, *huaqishen*, *yangshen*, or *guangdongshen*, refers to the dry root of the plant species *Panax quinquefolium* L. of the family Araliaceae. It has a sweet and slightly bitter taste and a cool nature, is involved in the heart, lung and kidney channels, and has the effects of invigorating Qi, nourishing Yin, clearing heat, and promoting fluid production. The term "Cordyceps", as used herein, refers to a dry complex from a dead body of an insect larva of the family Hepialidae and a stroma of the fungal species *Cordyceps sinensis* (Berk.) sace. of the family Clavicipitaceae parasitizing on the larva.

The term "fermented *Cordyceps sinensis* powder", as used herein, refers to a product of strains that were originally isolated from the natural Cordyceps of *Cordyceps sinensis* (Berk.) sace. and have been cultured under fermentation conditions, wherein the strains may be one of *Paecilomyces hepialli* Chen et Dai, sp. nov, *Hirsutella sinensis* Liu, Guo, Yu-et Zeng, sp. nov, *Cephalosporium sinensis* Chen sp. nov, *Mortiscrslla hepialid* C.T.&B.liu, *Paecilomyces sinensis* Chen, Xiao et Shi, sp. nov, *Tolypocladium sinensis* C.lan Li, *Cephalosporium sinens* Chen sp. nov, *Scytalidium hepialii* C.L.Li, *Chrysosporium sinens* Z.Q.liang, *Verticillium sinens* Wamg sp. nov, *Cephalosporium acremonium* Corda, Icones Fungorum, *Synnematium sinensis* Yin & Shen, *Isaria farinose* (Holmsk.) Fr. Systema Mycologicum, *Metarhizium anisopliae* (Metsch)Sorokin, *Hirsutella hepialid* Chen et Shen, *Sporothrix insectorum* de Hong & H.C.Evans, *Gliocladium roseum* (link)Thom and *Mortierella* sp., or any combination thereof.

The strain from which the fermented *Cordyceps sinensis* powder of the present invention is derived is preferably one or more of *Paecilomyces hepialli* Chen et Dai, sp. nov, *Mortiscrslla hepialid* C.T.&B.liu, *Synnematium sinensis* Yin & Shen, *Gliocladium roseum* (link)Thom, *Mortierella* sp., *Cephalosporium sinensis* Chen sp. nov or *Hirsutella sinensis* Liu,Guo,Yu-et Zeng, sp. nov, or any combination thereof.

The term "Flos Rosae Rugosae", as used herein, refers to the dry flower bud of the plant species *Rosa rugosa* Thumb or *Rose rugosacv*. Plena of the family Rosaceae. It has a pungent, sweet and slightly bitter taste and a warm nature, and represents a warm-natured drug. Its most significant effects are to activate Qi flowing, resolve stagnation, harmonize the blood, and relieve pain.

The term "Radix Codonopsis" refers to the dry root of the plant species *Codonopsis pilosula* (Franch.) Nannf., *Codonopsis pilosula* Nannf.var.modesta (Nannf.) L.T.Shen, or *Codonopsis tangshen* Oliv. of the family Campanulaceae.

The term "Radix Pseudostellariae" used here in refers to the dry tuberous root of the plant species *Pseudostellaria heterophylla* (Miq.) Pax ex Pax et Hoffm. of the family Cargophyllaceae.

The term "Folium Ginseng" refers to the dry leaves of the plant species *Panax ginseng* C. A. Mey. of the family Araliaceae.

The term "Radix Astragali" refers to the dry root of the plant species *Astragalus membranaceus* (Fisch)Bge.var.mongholicus(Bge) Hsiao or *Astragalus membranaceus* (Fisch)Bge. of the family Fabaceae.

The Ganoderma spore powder according to the present invention is preferably sporoderm-broken Ganoderma spore powder.

The Ganoderma spore powder according to the present invention is sexual reproductive cells of Ganoderma, i.e., basidiospore powder.

The Ganoderma spore oil according to the present invention is a fatty lipid substance extracted from Ganoderma spore powder.

The preparation method of the composition according to the present invention comprises: direct mixing the raw materials in parts by weight; or mixing the raw materials in parts by weight and extracting them with water and/or alcohol to obtain the composition; or extracting one or more of the raw materials with water and/or alcohol and using the extract as the active ingredient to prepare the composition.

The alcohol according to the present invention is methanol or ethanol; the methanol may be at a concentration of 5 to 95%, and the ethanol may be at a concentration of 5 to 95%.

A process for preparing the water and/or alcohol extracts of the raw materials for the traditional Chinese medicine composition according to the present invention comprises the steps of 1) weighing out traditional Chinese drugs as the raw materials; and 2) extracting the raw materials under reflux with alcohol or water to obtain a liquid extract as the active ingredient, and adding auxiliary agent(s) to prepare various dosage forms.

The process for preparing the water and/or alcohol extracts of the raw materials for the traditional Chinese medicine composition according to the present invention may comprise the steps of 1) weighing out traditional Chinese drugs as the raw materials, adding methanol or ethanol thereto to carry out extraction, recovering methanol or ethanol from the extraction liquid, to afford Extract I;

2) evaporating alcohol from the residual drugs, adding water to carry out extraction, to afford Extract II; and 3) combining Extract I and Extract II, carrying out filtration, concentrating the filtrate to an appropriate amount, adding pharmaceutically conventional auxiliary agent(s) to prepare a desired formulation by a pharmaceutically conventional process.

The process for preparing the water and/or alcohol extracts of the raw materials for the traditional Chinese medicine composition according to the present invention may comprise the steps of 1) raw material preparation: weighing out traditional Chinese drugs as the raw materials;

2) extraction and concentration: soaking the Chinese drug raw materials processed in step 1) in water, then decocting several times by heating, combining the liquid extracts to carry out filtration, concentrating the filtrate to an appropriate amount, cooling the concentrate and subjecting it to high-speed centrifugation to remove impurities, and reserving the product until use;

3) formulation preparation: preparing the concentrate obtained in step 2), alone or together with medicinally acceptable auxiliary agent(s), into a desired formulation by a pharmaceutically conventional process;

wherein, in step 2) above, the raw materials are soaked for 20 to 60 min, then decocted 1 to 3 times by heating for extraction, with each decoction lasting for 1 to 2 h and having a 6 to 13-fold amount of water added.

The composition according to the present invention can be prepared into any dosage form by adding an auxiliary agent or excipient acceptable in health care products, medicaments, or products.

The dosage form may be any one of a tablet, an oral liquid, a granule, a capsule, an electuary, a dripping pill, a pill, a powder, a lozenge, a fluid extract, an extract, an injection, and a syrup.

In order to provide a better understanding of the spirit of the present invention, animal experiments using the pharmaceutical composition made from Ganoderma, Radix Panacis Quinquefolii or Radix Et Rhizoma Ginseng, fermented *Cordyceps sinensis* powder and/or Cordyceps and the pharmaceutical composition made from Ganoderma, Flos Rosae Rugosae, Radix Panacis Quinquefolii or Radix Et Rhizoma Ginseng, fermented *Cordyceps sinensis* powder and/or Cordyceps, as well as the results thereof, are described hereinafter to demonstrate the effectiveness of the composition of the present invention in prevention and treatment of allergic diseases, allergic rhinitis, allergic dermatitis, urticaria, and allergic asthma.

Similarly, addition of any one or more of Ganoderma spore powder, Ganoderma spore oil, Ginseng, Radix Pseudostellariae, Radix Codonopsis, and Radix Astragali, or any combination thereof, can also lead to the same pharmacologic actions.

DETAILED EMBODIMENTS

Example 1

300 g Radix Panacis Quinquefolii, 400 g Ganoderma, 67 g Cordyceps, 200 g fermented *Cordyceps sinensis* powder (*Paecilomyces hepialli* Chen et Dai, sp. nov), and 300 g Flos Rosae Rugosae were weighed out. The Radix Panacis Quinquefolii and Ganoderma were sliced, and the fermented *Cordyceps sinensis* powder was put in a cloth bag. The Cordyceps was pulverized and then put in a cloth bag. The above five drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and impurities therein were then removed by high-speed centrifugation. A paste was made by further concentration under reduced pressure, or fine particles were made by spray drying; auxiliary agent(s) frequently used for oral liquid was added thereto and uniformly mixed, and a 20,000 ml oral liquid was prepared by conventional processes for oral liquid.

Example 2

300 g Radix Panacis Quinquefolii, 400 g Ganoderma, 200 g fermented *Cordyceps sinensis* powder (*Hirsutella sinensis* Liu,Guo,Yu-et Zeng, sp. nov), and 300 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 3

2 kg Ganoderma, 1.5 kg Radix Panacis Quinquefolii, and 1 kg fermented *Cordyceps sinensis* powder were weighed out. The Radix Panacis Quinquefolii and Ganoderma were sliced and the fermented *Cordyceps sinensis* powder was put in a cloth bag. The above three drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, designated as Composition 3, was used in the efficacy experiments as below.

Example 4

4 kg Ganoderma, 3 kg Radix Panacis Quinquefolii, and 0.67 kg Cordyceps were weighed out. The Radix Panacis Quinquefolii and Ganoderma were sliced, and the Cordyceps was pulverized and then put in a cloth bag. The above three drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 4, was used in the efficacy experiments as below.

Example 5

4 kg Ganoderma, 3 kg Radix Panacis Quinquefolii, 0.67 kg Cordyceps, and 2 kg fermented *Cordyceps sinensis* powder were weighed out. The Radix Panacis Quinquefolii and Ganoderma were sliced. The Cordyceps was pulverized and then put in a cloth bag. The fermented *Cordyceps sinensis* powder was put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 5, was used in the efficacy experiments as below.

Example 6

2.0 kg Ganoderma, 1.5 kg Radix Panacis Quinquefolii, 1.0 kg fermented *Cordyceps sinensis* powder (*Hirsutella*

*sinensis* Liu,Guo,Yu-et Zeng, sp. nov), and 1.5 kg Flos Rosae Rugosae were weighed out. The Radix Panacis Quinquefolii and Ganoderma were sliced and the fermented *Cordyceps sinensis* powder was put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 6, was used in the efficacy experiments as below.

Example 7

1.5 kg Radix Panacis Quinquefolii, 2.0 kg Ganoderma, 0.33 kg Cordyceps, and 1.5 kg Flos Rosae Rugosae were weighed out. The Radix Panacis Quinquefolii and Ganoderma were sliced. The Cordyceps was pulverized and then put in a cloth bag. The above four drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 7, was used in the efficacy experiments as below.

Example 8

2.0 kg Ganoderma, 1.5 kg Radix Panacis Quinquefolii, 0.33 kg *Cordyceps*, 1.0 kg fermented *Cordyceps sinensis* powder (*Paecilomyces hepialli* Chen et Dai, sp. nov), and 1.5 kg Flos Rosae Rugosae were weighed out. The Radix Panacis Quinquefolii and Ganoderma were sliced. The Cordyceps was pulverized and then put in a cloth bag together with the fermented *Cordyceps sinensis* powder. The above five drugs were soaked in water for 30 min, and decocted 3 times by heating. The first decoction lasted for 2 h with a 13-fold amount of water added, and the following decoctions each lasted for 1 h with a 10-fold amount of water added for each decoction. The three liquid extracts were combined and filtered. The filtrate was concentrated to produce a clear paste, which was then spray-dried to prepare a composite powder. The composition obtained, Composition 8, was used in the efficacy experiments as below.

Example 9

150 g Radix Panacis Quinquefolii, 90 g fermented *Cordyceps sinensis* powder (*Hirsutella hepialid* Chen et Shen), 120 g *Cordyceps,* 200 g Ganoderma, and 90 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 10

500 g Radix Et Rhizoma Ginseng, 100 g fermented *Cordyceps sinensis* powder (*Synnematium sinensis* Yin & Shen), 500 g Ganoderma, and 500 g Flos Rosae Rugosae were weighed out. The Radix Et Rhizoma Ginseng and Ganoderma were sliced, and the fermented *Cordyceps sinensis* powder and Flos Rosae Rugosae were put in a cloth bag. The above four drugs were soaked in water for 30 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 11

500 g Radix Panacis Quinquefolii, 100 g fermented *Cordyceps sinensis* powder (*Hirsutella sinensis* Liu,Guo, Yu-et Zeng, sp. nov), 500 g Ganoderma, and 500 g Flos Rosae Rugosae were weighed out. The Radix Panacis Quinquefolii and Ganoderma were sliced, and the fermented *Cordyceps sinensis* powder and Flos Rosae Rugosae were put in a cloth bag. The above four drugs were soaked in water for 20 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 12

150 g Radix Panacis Quinquefolii, 120 g *Cordyceps,* 200 g Ganoderma, and 90 g Flos Rosae Rugosae were weighed out. The Radix Panacis Quinquefolii and Ganoderma were sliced. The Cordyceps was pulverized and then put in a cloth bag. The above four drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 13

150 g Radix Et Rhizoma Ginseng, 90 g fermented *Cordyceps sinensis* powder (*Gliocladium roseum*(link)

Thom), 200 g Ganoderma, and 90 g Flos Rosae Rugosae were weighed out. The Radix Et Rhizoma Ginseng and Ganoderma were sliced, and the fermented *Cordyceps sinensis* powder was put in a cloth bag. The above four drugs were soaked in water for 1 h, and decocted twice by heating. The first decoction lasted for 2 h with a 15-fold amount of water added, and the second decoction lasted for 1.5 h with a 10-fold amount of water added. The two liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 14

150 g Radix Panacis Quinquefolii, 90 g fermented *Cordyceps sinensis* powder (*Hirsutella hepialid* Chen et Shen), 120 g *Cordyceps*, 200 g Ganoderma, and 90 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 15

100 g Radix Panacis Quinquefolii, 30 g *Cordyceps*, 200 g Ganoderma, and 100 g Flos Rosae Rugosae were weighed out. The Radix Panacis Quinquefolii and Ganoderma were sliced. The Cordyceps was pulverized and then put in a cloth bag. The above four drugs were soaked in water for 30 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 16

150 g Radix Panacis Quinquefolii, 30 g fermented *Cordyceps sinensis* powder (*Hirsutella sinensis* Liu,Guo,Yu-et Zeng, sp. nov), 200 g Ganoderma, and 100 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 17

90 g Radix Panacis Quinquefolii, 90 g *Cordyceps*, 120 g Ganoderma, and 60 g Flos Rosae Rugosae were weighed out. The Radix Panacis Quinquefolii and Ganoderma were sliced. The Cordyceps was pulverized and then put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 18

90 g Radix Et Rhizoma Ginseng, 90 g *Cordyceps*, 120 g Ganoderma, and 60 g Flos Rosae Rugosae were weighed out. The Radix Et Rhizoma Ginseng and Ganoderma were sliced. The Cordyceps was pulverized and then put in a cloth bag. The above four drugs were soaked in water for 30 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 19

90 g Radix Panacis Quinquefolii, 60 g fermented *Cordyceps sinensis* powder (*Cephalosporium sinensis* Chen sp. nov), 120 g Ganoderma, and 60 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 20

300 g Radix Panacis Quinquefolii, 400 g Ganoderma, 67 g Cordyceps, and 300 g Flos Rosae Rugosae were weighed out. The Radix Panacis Quinquefolii and Ganoderma were sliced. The Cordyceps was pulverized and then put in a cloth bag. The above four drugs were soaked in water for 1 h, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 21

300 g Radix Panacis Quinquefolii, 400 g Ganoderma, 200 g fermented *Cordyceps sinensis* powder (*Paecilomyces hepialli* Chen et Dai, sp. nov), and 300 g Flos Rosae Rugosae were weighed out. The Radix Panacis Quinquefolii and Ganoderma were sliced, and the fermented *Cordyceps sinensis* powder was put in a cloth bag. The above four drugs were soaked in water for 20 min, and decocted 3 times by heating. Each decoction lasted for 1 h with a 10-fold amount of water added. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 22

500 g Radix Panacis Quinquefolii, 100 g *Cordyceps,* 500 g Ganoderma, 500 g Flos Rosae Rugosae and 500 g sporoderm-broken Ganoderma spore powder were weighed out. The Radix Panacis Quinquefolii and Ganoderma were sliced. The Cordyceps was pulverized and then put in a cloth bag. The above four drugs were soaked in water for 20 min, and decocted 3 times by heating. The first decoction lasted for 2 h with a 15-fold amount of water added, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the sporoderm-broken Ganoderma spore powder were added thereto and uniformly mixed; and various types of tablets were prepared by conventional processes for tablets.

Example 23

500 g Radix Et Rhizoma Ginseng, 100 g fermented *Cordyceps sinensis* powder (*Paecilomyces sinensis* Chen, Xiao et Shi, sp. nov), 500 g Ganoderma, 500 g Flos Rosae Rugosae and 500 g sporoderm-broken Ganoderma spore powder were weighed out. The Radix Et Rhizoma Ginseng and Ganoderma were sliced, and the fermented *Cordyceps sinensis* powder and the sporoderm-broken Ganoderma spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for tablets.

Example 24

150 g Radix Panacis Quinquefolii, 90 g fermented *Cordyceps sinensis* powder (*Tolypocladium sinensis* C.lan Li), 200 g Ganoderma, 90 g Flos Rosae Rugosae and 150 g sporoderm-broken Ganoderma spore powder were weighed out. The Radix Panacis Quinquefolii and Ganoderma were sliced, and the fermented *Cordyceps sinensis* powder was put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the Ganoderma spore powder were added thereto and uniformly mixed; and various types of tablets were prepared by conventional processes for tablets.

Example 25

500 g Radix Panacis Quinquefolii, 100 g *Cordyceps,* 500 g Ganoderma, 500 g Flos Rosae Rugosae and 100 g Ganoderma spore oil were weighed out. The Radix Panacis Quinquefolii and Ganoderma were sliced, and the Cordyceps was pulverized. Upon addition of 80% ethanol, the above four drugs were extracted twice under reflux, with each extraction lasting for 2 h, and then filtered. Ethanol was recovered from the liquid filtrate until no ethanol odor could be smelled. A paste was made by further concentration under reduced pressure, or fine particles were made by spray drying; auxiliary agents frequently used for dripping pills and the Ganoderma spore oil were added thereto and uniformly mixed; and dripping pills were prepared by conventional processes for dripping pills.

Example 26

500 g Radix Panacis Quinquefolii, 100 g fermented *Cordyceps sinensis* powder (*Synnematium sinensis* Yin & Shen), 500 g Ganoderma, 500 g Flos Rosae Rugosae, 500 g sporoderm-broken Ganoderma spore powder, 100 g Ganoderma spore oil and 100 g Folium Ginseng were weighed out. The Radix Panacis Quinquefolii and Ganoderma were sliced, and the fermented *Cordyceps sinensis* powder was put in a cloth bag. The above drugs were soaked in water for 40 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules, the sporoderm-broken Ganoderma spore powder and the Ganoderma spore oil were added thereto and uniformly mixed; and granules were prepared by conventional processes for granules.

Example 27

150 g Radix Panacis Quinquefolii, 90 g fermented *Cordyceps sinensis* powder (*Hirsutella hepialid* Chen et Shen), 200 g Ganoderma, 90 g Flos Rosae Rugosae and 400 g Radix Codonopsis were weighed out. The Radix Panacis Quinquefolii, Ganoderma and Radix Codonopsis were sliced, and the fermented *Cordyceps sinensis* powder was put in a cloth bag. The above five drugs were soaked in water for 40 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 28

150 g Radix Panacis Quinquefolii, 120 g *Cordyceps,* 200 g Ganoderma, 90 g Flos Rosae Rugosae and 400 g Radix Astragali were weighed out. The Radix Panacis Quinquefolii, Ganoderma and Radix Astragali were sliced. The Cordyceps was pulverized and then put in a cloth bag. The above five drugs were soaked in water for 20 min, and decocted 3 times by heating. The first decoction lasted for 2 h and the following decoctions each lasted for 1 h, with a 14-fold amount of water added for each decoction. The three liquid extracts were combined and filtered, the liquid filtrate was concentrated to an appropriate level, the liquid concentrate was left to cool down, and the impurities therein were then removed by high-speed centrifugation, auxiliary agent(s) frequently used for lozenges was added thereto and uniformly mixed, and lozenges were prepared by conventional processes for lozenges.

Example 29

500 g Radix Panacis Quinquefolii, 50 g fermented *Cordyceps sinensis* powder (*Paecilomyces hepialli* Chen et Dai, sp. nov), 50 g fermented *Cordyceps sinensis* powder (*Hirsutella sinensis* Liu,Guo,Yu-et Zeng, sp. nov), 500 g Ganoderma, 500 g Flos Rosae Rugosae and 300 g Radix Codonopsis were weighed out. The Radix Panacis Quinquefolii, Ganoderma and Radix Codonopsis were sliced, and the fermented *Cordyceps sinensis* powders were put in a cloth bag. The above five drugs were soaked in water for 1 h, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agent(s) frequently used for powder was added thereto and uniformly mixed; and powder was prepared by conventional processes for powder.

Example 30

500 g Radix Panacis Quinquefolii, 100 g *Cordyceps,* 500 g Ganoderma, 500 g Flos Rosae Rugosae and 300 g Radix Astragali were weighed out. The Radix Panacis Quinquefolii, Ganoderma and Radix Astragali were sliced. The Cordyceps was pulverized and then put in a cloth bag. The above five drugs were soaked in water for 20 min, and decocted 3 times by heating. The first decoction lasted for 2 h and the following decoctions each lasted for 1 h, with a 14-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 31

100 g Radix Panacis Quinquefolii, 200 g Ganoderma, 30 g Cordyceps, 3 g fermented *Cordyceps sinensis* powder (Cs-C-Q80 *Hirsutella sinensis* Liu,Guo,Yu-et Zeng, sp. nov), 100 g Flos Rosae Rugosae and 100 g Ganoderma spore powder were weighed out. The Radix Panacis Quinquefolii and Ganoderma were sliced, and the Cordyceps was pulverized and put in a cloth bag together with the Ganoderma spore powder. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets were added thereto and uniformly mixed; and various types of tablets were prepared by conventional processes for tablets.

Example 32

100 g Radix Panacis Quinquefolii, 200 g Ganoderma, 30 g fermented *Cordyceps sinensis* powder (*Mortiscrslla hepialid* C.T.& B.liu), 100 g Flos Rosae Rugosae and 100 g Ganoderma spore powder were weighed out. The Radix Panacis Quinquefolii and Ganoderma were sliced, and the fermented *Cordyceps sinensis* powder and the Ganoderma spore powder were put in a cloth bag. The above five drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills were added thereto and uniformly mixed; and various types of pills were prepared by conventional processes for pills.

Example 33

90 g Radix Panacis Quinquefolii, 120 g Ganoderma, 90 g *Cordyceps*, 60 g Flos Rosae Rugosae and 90 g Ganoderma spore oil were weighed out. The Radix Panacis Quinquefolii and Ganoderma were sliced. The Cordyceps was pulverized and then put in a cloth bag. The above four drugs were soaked in water for 30 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules and the Ganoderma spore oil were added thereto and uniformly mixed; and granules were prepared by conventional processes for granules.

Example 34

100 g Radix Panacis Quinquefolii, 200 g Ganoderma, 30 g *Cordyceps*, 100 g Flos Rosae Rugosae and 200 g Radix Pseudostellariae were weighed out. The Radix Panacis Quinquefolii and Ganoderma were sliced, and the Cordyceps was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, auxiliary agent(s) frequently used for soft extracts was added thereto and uniformly mixed, and a soft extract was prepared by conventional processes for soft extracts.

Example 35

100 g Radix Panacis Quinquefolii, 200 g Ganoderma, 30 g *Cordyceps*, 100 g Flos Rosae Rugosae and 200 g Folium Ginseng were weighed out. The Radix Panacis Quinquefolii and Ganoderma were sliced, and the Cordyceps was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 36

100 g Radix Panacis Quinquefolii, 200 g Ganoderma, 30 g fermented *Cordyceps sinensis* powder (Mortierella sp.), 100 g Flos Rosae Rugosae and 200 g Radix Codonopsis were weighed out. The Radix Panacis Quinquefolii, Ganoderma and Radix Codonopsis were sliced, and the fermented *Cordyceps sinensis* powder was put in a cloth bag. The above five drugs were soaked in water for 40 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 37

100 g Radix Panacis Quinquefolii, 200 g Ganoderma, 30 g fermented *Cordyceps sinensis* powder (*Verticillium* sinens Wamg sp. nov), 100 g Flos Rosae Rugosae and 200 g Radix Astragali were weighed out. The Radix Panacis Quinquefolii, Ganoderma and Radix Astragali were sliced, and the fermented *Cordyceps sinensis* powder was put in a cloth bag. The above five drugs were soaked in water for 40 min, and decocted 3 times by heating. The first decoction lasted for 2 h, and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for capsules were added thereto and uniformly mixed; and capsules were prepared by conventional processes for capsules.

Example 38

90 g Radix Panacis Quinquefolii, 120 g Ganoderma, 30 g fermented *Cordyceps sinensis* powder (*Cephalosporium sinensis* Chen sp. nov), 30 g fermented *Cordyceps sinensis* powder (*Synnematium sinensis* Yin & Shen), 60 g Flos Rosae Rugosae and 60 g Ganoderma spore oil were weighed out. The Radix Panacis Quinquefolii and Ganoderma were sliced, and the fermented *Cordyceps sinensis* powders were put in a cloth bag. The above four drugs were soaked in water for 1 h, and decocted 3 times by heating. The first decoction lasted for 2 h, and the following decoctions each lasted for 1 h, with a 13-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for pills and the Ganoderma spore oil were added thereto and uniformly mixed; and various types of pills were prepared by conventional processes for pills.

Example 39

90 g Radix Panacis Quinquefolii, 120 g Ganoderma, 90 g *Cordyceps*, 60 g Flos Rosae Rugosae, 200 g Radix Astragali, and 10 g Ganoderma spore oil were weighed out. The Radix Panacis Quinquefolii, Ganoderma and Radix Astragali were sliced, and the Cordyceps was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 40

300 g Radix Panacis Quinquefolii, 400 g Ganoderma, 200 g fermented *Cordyceps sinensis* powder (*Scytalidium hepialii* C.L.Li), 300 g Flos Rosae Rugosae and 400 g Ganoderma spore powder were weighed out. The Radix Panacis Quinquefolii and Ganoderma were sliced, and the Cordyceps was pulverized and then put in a cloth bag. The above four drugs were soaked in water for 20 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for tablets and the Ganoderma spore powder were added thereto and uniformly mixed; and various types of tablets were prepared by conventional processes for tablets. An oral liquid was prepared by adding auxiliary agent(s) frequently used for oral liquid. The composition obtained, Composition 40, was used in the efficacy experiments as below.

Example 41

300 g Radix Panacis Quinquefolii, 400 g Ganoderma, 67 g *Cordyceps,* 300 g Flos Rosae Rugosae and 20 g Ganoderma spore oil were weighed out. The Radix Panacis Quinquefolii and Ganoderma were sliced, and the Cordyceps was pulverized and then put in a cloth bag. The above four drugs were soaked in water for 30 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules and the Ganoderma spore oil were added thereto and uniformly mixed; and granules were prepared by conventional processes for granules.

Example 42

300 g Radix Panacis Quinquefolii, 400 g Ganoderma, 200 g fermented *Cordyceps sinensis* powder (*Cephalosporium sinens* Chen sp. nov), 300 g Flos Rosae Rugosae and 400 g Radix Pseudostellariae were weighed out. The Radix Panacis Quinquefolii and Ganoderma were sliced, and the fermented *Cordyceps sinensis* powder was put in a cloth bag. The above five drugs were soaked in water for 40 min, and decocted 3 times by heating. The first decoction lasted for 2 h and the following decoctions each lasted for 1 h, with a 10-fold amount of water added for each decoction. The three liquid extracts were combined and filtered, the liquid filtrate was concentrated to an appropriate level, the liquid concentrate was left to cool down, and the impurities therein were then removed by high-speed centrifugation. A paste was made by further concentration under reduced pressure, or fined particles were made by spray drying; auxiliary agents frequently used for tablets were added thereto and uniformly mixed; and various types of tablets were prepared by conventional processes for tablets.

Example 43

300 g Radix Panacis Quinquefolii, 400 g Ganoderma, 67 g *Cordyceps,* 300 g Flos Rosae Rugosae and 400 g Radix Pseudostellariae were weighed out. The Radix Panacis Quinquefolii and Ganoderma were sliced, and the Cordyceps was pulverized and then put in a cloth bag. The above five drugs were soaked in water for 40 min, and decocted 3 times by heating. The first decoction lasted for 2 h with a 15-fold amount of water added, and the following decoctions each lasted for 1 h with a 10-fold amount of water added for each decoction. The three liquid extracts were combined and filtered, the liquid filtrate was concentrated to an appropriate level, the liquid concentrate was left to cool down, the impurities therein were then removed by high-speed centrifugation, auxiliary agents frequently used for syrups were added thereto and uniformly mixed, and a syrup was prepared by conventional processes for syrups.

Example 44

300 g Radix Panacis Quinquefolii, 400 g Ganoderma, 100 g fermented *Cordyceps sinensis* powder (*Chrysosporium sinens* Z.Q.liang), 100 g fermented *Cordyceps sinensis* powder (*Hirsutella sinensis* Liu,Guo,Yu-et Zeng, sp. nov), and 300 g Flos Rosae Rugosae were weighed out. The Radix Panacis Quinquefolii and Ganoderma were sliced, and the fermented *Cordyceps sinensis* powders were put in a cloth bag. Upon addition of 5% methanol, the drugs were extracted twice under reflux, with each extraction lasting for 1 h. Then the liquid extracts were combined, and methanol was recovered to obtain an alcohol extract. The residual drugs were further decocted twice in water by heating. The first decoction lasted for 2 h, and the following decoction lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 45

300 g Radix Panacis Quinquefolii, 400 g Ganoderma, 67 g *Cordyceps,* 20 g fermented *Cordyceps sinensis* powder (*Hirsutella sinensis* Liu,Guo,Yu-et Zeng, sp. nov), and 300 g Flos Rosae Rugosae were weighed out. The Radix Panacis Quinquefolii and Ganoderma were sliced, and the Cordyceps was pulverized and then put in a cloth bag. Upon addition of 75% ethanol, the drugs were extracted for 2 h under reflux, and ethanol was recovered to obtain an alcohol extract. The residual drugs were further decocted three times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 46

300 g Radix Et Rhizoma Ginseng, 400 g Ganoderma, 200 g fermented *Cordyceps sinensis* powder (*Cephalosporium acremonium* Corda,Icones Fungorum), 300 g Flos Rosae Rugosae and 400 g Radix Codonopsis were weighed out. The Radix Et Rhizoma *Ginseng, Ganoderma* and Radix Codonopsis were sliced, and the fermented *Cordyceps sinensis* powder was put in a cloth bag. Upon addition of 95% methanol, the drugs were extracted twice under reflux, with each extraction lasting for 1 h. Then the liquid extracts were combined, and methanol was recovered to obtain an alcohol extract. The residual drugs were further decocted 3 times in water by heating. The first decoction lasted for 2 h, and the following decoctions lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 47

300 g Radix Et Rhizoma Ginseng, 400 g Ganoderma, 200 g fermented *Cordyceps sinensis* powder (*Sporothrix insectorum* de Hong & H.C.Evans), 300 g Flos Rosae Rugosae and 400 g Radix Codonopsis were weighed out. The Radix Et Rhizoma Ginseng and Ganoderma were sliced, and the Cordyceps was pulverized and put in a cloth bag. Upon addition of 95% ethanol, the drugs were extracted under reflux for 2 h, and ethanol was recovered to obtain an alcohol extract. The residual drugs were further decocted 3 times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 48

300 g Radix Et Rhizoma Ginseng, 400 g Ganoderma, 67 g *Cordyceps,* 300 g Flos Rosae Rugosae, 300 Ganoderma spore powder and 400 g Radix Astragali were weighed out. The Radix Et Rhizoma Ginseng and Ganoderma were sliced, and the Cordyceps was pulverized and then put in a cloth bag. Upon addition of 5% ethanol, the drugs were extracted under reflux for 2 h, and ethanol was recovered to obtain an alcohol extract. The residual drugs were further decocted twice in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 49

300 g Radix Panacis Quinquefolii, 400 g Ganoderma, 200 g fermented *Cordyceps sinensis* powder (*Isaria farinose* (Holmsk.)Fr.Systema Mycologicum), 300 g Flos Rosae Rugosae and 400 g Radix Astragali were weighed out. The Radix Panacis Quinquefolii and Ganoderma were sliced, and the fermented *Cordyceps sinensis* powder was put in a cloth bag. Upon addition of 95% methanol, the drugs were extracted twice under reflux for 2 h, with each extraction lasting for 1 h. Then the liquid extracts were combined, and methanol was recovered to obtain an alcohol extract. The residual drugs were further decocted 3 times in water by heating. The first decoction lasted for 2 h, and the following decoctions lasted for 1 h, with a 10-fold amount of water added for each decoction. The alcohol extract and water extracts were combined and filtered, the liquid filtrate was concentrated to an appropriate level, the liquid concentrate was left to cool down, and the impurities therein were then removed by high-speed centrifugation. A paste was made by further concentration under reduced pressure, or fine particles were made by spray drying; auxiliary agents frequently used for granules were added thereto and uniformly mixed; and granules were prepared by conventional processes for granules.

Example 50

300 g Radix Panacis Quinquefolii, 400 g Ganoderma, 67 g *Cordyceps,* 300 g Flos Rosae Rugosae, and 90 g Folium Ginseng were weighed out. The Radix Panacis Quinquefolii and Ganoderma were sliced, and the Cordyceps was pulverized and then put in a cloth bag. Upon addition of 5% ethanol, the drugs were extracted under reflux for 2 h, and ethanol was recovered to obtain an alcohol extract. The residual drugs were further decocted 3 times in water by heating, with each decoction lasting for 2 h. The alcohol extract and water extracts were combined and filtered, the liquid filtrate was concentrated to an appropriate level, the liquid concentrate was left to cool down, and the impurities therein were then removed by high-speed centrifugation, auxiliary agent(s) frequently used for oral liquid was added thereto and uniformly mixed, and a 20,000 ml oral liquid was prepared by conventional processes for oral liquid.

Example 51. Animal Experiment Report of
Composition 3 Obtained in Example 3 Against
Allergy and Allergic Dermatitis 1. Materials and Methods
1.1 Sources of Samples The test drug was Composition 3 (Radix Panacis Quinquefolii, Ganoderma, and fermented *Cordyceps sinensis* powder) provided by Jiangzhong Pharmaceutical Co. Ltd. as composite powder. 1 g dry composite powder was equivalent to 11.41 g total crude drugs. Its daily intake recommended for one person was 24 g crude drug/60 kg body weight.

1.2 Laboratory Animals

Clean grade healthy Kunming mice, half of which were male and the other half female, each weighing 18 to 22 g, were provided by the Laboratory Animal Center, Jiangxi University of Traditional Chinese Medicine (Certification Number: SCXK (Jiangxi) 2005-0001). Clean grade healthy SD rats, half of which were male and the other half female, were provided by the Laboratory Animal Center, Jiangxi University of Traditional Chinese Medicine (Certification Number: SCXK (Jiangxi) 2006-0001).

1.3 Primary Reagents

Ovalbumin (OVA) (Sigma, batch No.: 025K0594); Evans Blue (EB) (Sinopharm (Group) Shanghai Chemical Reagent Co., Ltd., batch No.: F20030714); histamine phosphate, manufactured by Shanghai Biological Reagent Factory, batch No.: 909035; 2,4-dinitrochlorobenzene, Chemical pure, manufactured by Guangzhou Chemical Reagent Factory, batch No.: 0703428; prednisone, manufactured by Xianju Pharmaceuticals Co. Ltd., batch No.: 090678.

1.4 Primary Instruments

BS110S electronic balance, manufactured by Sartorius Inc.; centrifuge (Anting, Shanghai); digital thermostatic water-bath (Jintan, Zhejiang); perforator (8 mm in diameter); micropipette (Gilson, France). OLYMPUS microscope; YT-6C water bath-slide driver (Yaguang Medical Electronics Technology Inc., Xiaogan, Hubei); PH140A incubator/oven (Shanghai Yiheng Technology Co., Ltd).

2. Experimental Methods
2.1 Animal Grouping

Animals were randomly divided into groups with 10 animals per group based on the body weight. A model control group, groups on the low, medium and high doses of Composition 3, and a positive drug control group (prednisone) were established.

2.2 Dosage Regime

The daily intake of test drug Composition 3 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (17.53 mg dry powder/ml, 35.06 mg dry powder/ml, and 105.18 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.765 mg dry powder/ml, 17.53 mg dry powder/ml, and 52.59 mg dry powder/ml) with distilled water to carry out experiments.

2.3 Effect of Composition 3 on Passive Anaphylaxis (PCA) in Rats Caused by Ovalbumin
2.3.1 Preparation of Antiserum 5% OVA in physiological saline was injected into a hind limb of the rats at 0.2 ml/hind limb, while a pertussis vaccine was injected intraperitoneally at 0.15 ml/rat. After a normal feeding of 13 days, blood was drawn from the eye socket, and was centrifuged at 2000 rpm for 15 min Anti-OVA serum was isolated therefrom and stored in a −20° C. refrigerator until use.

2.3.2 Establishment of Rat Anti-Ovalbumin Serum Models

Anti-ovalbumin serum was taken and diluted at 1:4 or 1:8 with physiological saline. 50 SD rats were randomly divided into 5 groups, i.e., a model control group, groups on the low, medium and high doses of Composition 3, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 3 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].

2.3.3 Effect of Composition 3 on Delayed Hypersensitivity in Mouse Auricle Skin Caused by 2,4-Dinitrochlorobenzene 50 mice were randomly divided into 5 groups, i.e., a model control group, groups on the low, medium and high doses of Composition 3, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 3 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 3 on Local Itching in Mice Caused by Low-Molecular-Weight Dextran 50 mice were randomly divided into 5 groups, i.e., a model control group, groups on the low, medium and high doses of Composition 3, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 3 on Capillary Permeability in Rats 50 rats were randomly divided into 5 groups, i.e., a model control group, groups on the low, medium and high doses of Composition 3, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 3 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

Experimental data were presented in $\bar{X} \pm S$. One-way ANOVA analysis was employed to compare the differences among the model control group and the groups on various doses of Composition 3. $P<0.05$ was considered as significantly different. $P<0.01$ was considered as highly significantly different.

3. Results 3.1 Effect of Composition 3 on Passive Anaphylaxis in Rats

Test results were shown in Tables 1 and 2. As compared to the model control group, the low dose group on Composition 3 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 3 all showed an effect of significant decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 3 had a significant inhibitory effect on passive anaphylaxis in rats.

TABLE 1

Effect of Composition 3 on the diameter of PCA blue spots in rats ($\bar{x} \pm s$)

| Groups | Dose (g crude drug/kg) | Number of animals | Diameter of blue spots (mm) 1:4 | 1:8 |
| --- | --- | --- | --- | --- |
| Model control group | 0.0 | 10 | 16.90 ± 2.61 | 10.26 ± 1.31 |
| Positive control group | 5.0 mg | 10 | 12.79 ± 1.88** | 7.43 ± 1.22** |
| Test drug low-dose group | 1.2 | 10 | 15.20 ± 1.44 | 9.44 ± 1.20 |
| Test drug medium-dose group | 2.4 | 10 | 14.15 ± 2.08* | 8.97 ± 1.33* |
| Test drug high-dose group | 7.2 | 10 | 13.32 ± 2.17** | 8.34 ± 1.15** |

*$P < 0.05$,
**$P < 0.01$ vs. model control group.

TABLE 2

Effect of Composition 3 on the mast cell degranulation and serum histamine content in PCA rats ($\bar{x} \pm s$)

| Groups | Dose (g crude drug/kg) | Number of animals | Degranulation | Histamine fluorescence (mg · L) |
| --- | --- | --- | --- | --- |
| Model control group | 0.0 | 10 | 60.80 ± 15.64 | 4.08 ± 0.93 |
| Positive control group | 5.0 mg | 10 | 22.54 ± 11.25** | 2.35 ± 0.65** |
| Test drug low-dose group | 1.2 | 10 | 48.42 ± 13.90 | 3.39 ± 0.86 |
| Test drug medium-dose group | 2.4 | 10 | 42.65 ± 16.27* | 2.97 ± 0.88* |
| Test drug high-dose group | 7.2 | 10 | 35.52 ± 13.28** | 2.62 ± 0.40** |

*$P < 0.05$,
**$P < 0.01$ vs. model control group.

3.2 Effect of Composition 3 on Delayed Hypersensitivity in Mouse Auricle Skin Caused by 2,4-Dinitrochlorobenzene The results were shown in Table 3. As compared to the model control group, the swelling degree of mouse auricle discs significantly decreased in the groups on the medium and high doses of Composition 3, indicating that Composition 3 had a good inhibitory effect on delayed hypersensitivity in mouse auricle skin caused by 2,4-dinitrochlorobenzene.

TABLE 3

Effect of Composition 3 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
| --- | --- | --- | --- |
| Model control group | 0.0 | 10 | 6.98 ± 0.74 |
| Positive control group | 5.0 mg | 10 | 5.07 ± 0.59** |
| Test drug low-dose group | 2.0 | 10 | 6.30 ± 0.90 |

TABLE 3-continued

Effect of Composition 3 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Test drug medium-dose group | 4.0 | 10 | 6.16 ± 0.64* |
| Test drug high-dose group | 12.0 | 10 | 5.42 ± 0.80** |

*$P < 0.05$,
**$P < 0.01$ vs. model control group.

3.3 Effect of Composition 3 on Local Itching in Mice Caused by Low-Molecular-Weight Dextran The test results were shown in Table 4. As compared to the model control group, the OD value significantly decreased in the rat groups on the medium and high doses of Composition 3, indicating that Composition 3 was significantly effective in decreasing the capillary permeability increase in rats caused by histamine phosphate.

TABLE 4

Effect of Composition 3 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 29.30 ± 6.62 |
| Positive control group | 5.0 mg | 10 | 18.30 ± 4.62** |
| Test drug low-dose group | 2.0 | 10 | 25.52 ± 7.80 |
| Test drug medium-dose group | 4.0 | 10 | 23.34 ± 5.24* |
| Test drug high-dose group | 12.0 | 10 | 20.10 ± 4.47** |

*$P < 0.05$,
**$P < 0.01$ vs. model control group.

3.4 Effect of Composition 3 on Capillary Permeability in Rats

The test results were shown in Table 5. As compared to the model control group, the OD value significantly decreased in the rat groups on the medium and high doses of Composition 3, indicating that Composition 3 was significantly effective in decreasing the capillary permeability increase in rats caused by histamine phosphate.

TABLE 5

Effect of Composition 3 on capillary permeability in rats ($\bar{x} \pm s$)

| Groups | Dose (g crude drug/kg) | Number of animals | OD value |
|---|---|---|---|
| Model control group | 0.0 | 10 | 0.994 ± 0.142 |
| Positive control group | 5.0 mg | 10 | 0.750 ± 0.116** |
| Test drug low-dose group | 1.2 | 10 | 0.960 ± 0.142 |
| Test drug medium-dose group | 2.4 | 10 | 0.857 ± 0.135* |
| Test drug high-dose group | 7.2 | 10 | 0.780 ± 0.127** |

*$P < 0.05$,
**$P < 0.01$ vs. model control group.

4. Conclusion

The animal experimental studies demonstrate that Composition 3 is significantly effective in inhibiting passive anaphylaxis in rats caused by ovalbumin, that Composition 3 is effective in inhibiting delayed hypersensitivity in mouse auricle skin caused by 2,4-dinitrochlorobenzene, and that Composition 3 is significantly effective in decreasing the capillary permeability increase in rats caused by histamine phosphate. The above results indicate good effectiveness of Composition 3 in resisting allergy and in preventing and treating allergic diseases such as allergic dermatitis and urticaria.

Example 52. Animal Experiment Report of Composition 3 Obtained in Example 3 in Prevention and Treatment of Allergic Rhinitis 1. Materials and Methods
1.1 Sources of Samples The test drug was Composition 3 (Radix Panacis Quinquefolii, Ganoderma, and fermented *Cordyceps sinensis* powder) provided by Jiangzhong Pharmaceutical Co. Ltd. as composite powder. 1 g dry composite powder was equivalent to 11.41 g total crude drugs.

1.2 Laboratory Animals

Clean grade SD rats, half of which were male and the other half female, each weighing 180 to 220 g, were provided by the Laboratory Animal Center, Jiangxi University of Traditional Chinese Medicine (Certification Number: SCXK (Jiangxi) 2006-0001). Guinea pigs, half of which were male and the other half female, each weighing 250 to 300 g, were from Dongchuang Experimental Animal Service Department, Kaifu District, Changsha.

1.3 Primary Reagents

Tolylene-2,4-diisocyanate (TDI) (Shanghai First Reagent Factory, batch No.: 090301); Ovalbumin (OVA) (Sigma, batch No.: 025K0594); Bi-yan-kang tablets (Foshan Dezhong Pharmaceutical Co., Ltd., batch No.: 090701); cAMP and cGMP kits (Great Wall Biochemicals).

1.4 Primary Instruments

Beckman-CX7 automatic blood biochemical analyzer; OLYMPUS microscope; TE2000-S inverted fluorescence phase contrast digital microscope (Nikon Inc., Japan); microtome (Leica, Germany); YT-6C water bath-slide driver (Yaguang Medical Electronics Technology Inc., Xiaogan, Hubei).

2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on the low, medium and high doses of Composition 3, with 10 animals in each group.

2.1.2 Dosage Regime

The daily intake of the test drug Composition 3 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. The volume of intragastric administration was calculated as 1.0 ml/100 g body weight. The blank control group and the allergic rhinitis model group were intragastrically given an equivalent volume of physiological saline; the Bi-yan-kang group was given the drug at a dose of 410 mg/kg. The intragastric administration was initiated after a successful modeling and carried out once per day for 21 consecutive days.

2.1.3 Establishment of Rat Allergic Rhinitis Animal Models 1 ml physiological saline was added to 0.3 mg OVA as an antigen[1] and 30 mg aluminum hydroxide powder as an adjuvant to prepare a suspension, which was intraperitoneally injected once every other day for 7 times in total. Afterwards, local immunization was conducted in each nasal cavity with 10 µl 5% OVA once per day for 7 days. An equivalent volume of physiological saline was administered to the blank control group. During the administration of the test drug, nasal administration with 50 µl 1% OVA was still conducted every other day.

Evaluation criteria for the effectiveness of modeling: the effectiveness was evaluated by scoring; during a 30-min observation after the challenging, the times of sneezing, the level of nose itching, and the amount of nasal secretion were recorded. The scoring criteria are shown in Table 1.

TABLE 1

Scoring criteria for allergic rhinitis symptoms

| Symptom score (pts) | Times of sneezing | Level of nose itching | Nasal mucus |
| --- | --- | --- | --- |
| 1 | 1~3 | Scratching the nose slightly | Reaching the anterior nasal aperture |
| 2 | 4~10 | Scratching the nose frequently | Beyond the anterior nasal aperture |
| 3 | above 10 | Scratching the nose continually | All over the face |

A total score of 5 pts indicated a successful modeling, after which the nasal administration was continued until the treatment experiment was completed.

2.1.4 Assay Indicators

Blood cAMP and cGMP levels were measured and mast cells in the nasal mucosa tissues were counted.

2.1.4.1 Blood cAMP and cGMP Measurement

Blood was drawn from the carotid artery, and serum was isolated for ELISA.

2.1.4.2 Nasal Mucosal Mast Cell Counting

Skin in the nasal maxillary area was peeled off, the maxillary was isolated from the skull and was dissected along the nasal median to expose the nasal septum and nasal cavities on both sides. The anterior and middle section of the nasal septum was cut off and fixed in a 10% formaldehyde solution for 72 h, then put into a decalcification solution to decalcify for 3 days, dehydrated with an alcohol gradient till clearness, and embedded in paraffin. Conventional sections of 4 µm were made and stained with toluidine blue, and were observed under a microscope to count the total number of mast cells in the sample.

2.2 Effect on Allergic Rhinitis in Guinea Pigs Caused by TDI 2.2.1. The Same as in 2.1.1.

2.2.2. The Same as in 2.1.2.

2.2.3 Establishment of Guinea Pig Allergic Rhinitis Animal Models

Modeling was carried out with TDI. Guinea pigs other than those in the blank control group were modeled using a 10% TDI. 10 µl was pipetted dropwise into both nasal cavities of the guinea pigs (5 µl for each side) once per day for consecutive 7 days, to establish guinea pig allergic rhinitis animal models[1]. An equivalent volume of olive oil was nasally administered to the blank control group. The nasal administration was continued until the treatment experiment was completed.

Evaluation criteria for the effectiveness of modeling: the effectiveness was evaluated by scoring; during a 30-min observation after the challenging, the times of sneezing, the level of nose itching, and the amount of nasal secretion were recorded. The scoring criteria are shown in Table 1.

2.2.4 Assay Indicators

Behavior observation; count of eosinophils in nasal secretion; total serum IgE and blood histamine measurements; nasal mucosa thickness measurement.

2.2.4.1 Guinea Pig Behavior Observation

After challenging with TDI nasal administration, scores were given according to the criteria in Table 1.

2.2.4.2 Count of Eosinophils (EOS) in Nasal Secretion

Nasal secretion from guinea pigs was smeared on a slide, and improved according to the Loren's method[2]. Apparent EOSs were visible in the field at 40× magnification under the digital microscope, and the number of EOSs in lamina propria at this site was counted in 3 to 5 high power fields and used to indicate the degree of infiltration of EOSs.

2.2.4.3 Total Serum IgE and Blood Histamine Measurement

One day after the administration was completed, the guinea pigs were anesthetized with 10% chloral hydrate and blood was drawn from the abdominal aorta. Total serum IgE was measured by radioimmunoassay. Another 5 ml of the blood was added in an anticoagulative tube and stored at −20° C. until use. Histamine was extracted, and the histamine content was determined by fluorescence spectrophotometry[3]. The equation for calculation was as follows:

Histamine content in blood (mg/L)=[(value of the sample−value of the sample blank)/(value of the standard−value of the standard blank)]×standard histamine concentration (The standard histamine concentration was 50.2 mg·L$^{-1}$).

2.2.4.4 Nasal Mucosa Thickness Measurement

Material collecting and sectioning were the same as in Experiment 2.1.4.2. After HE staining, the nasal mucosa thickness was measured quantitatively with an image analyzer. The distance from the apex of mucosal protrusions in the mucosa area covered with the pseudostratified ciliated columnar epithelium to the nasal septum cartilage (including the epithelial layer and lamina propria) in each sample was determined as the mucosa thickness.

2.3 Statistic Method

Experimental data were presented in $\bar{X} \pm S$. One-way ANOVA analysis was employed to compare the differences among the blank control group, the model control group and the groups on various doses of Composition 3. $P<0.05$ was considered as significantly different. $P<0.01$ was considered as highly significantly different.

3. Results
3.1 Effect of Composition 3 on Allergic Rhinitis in Rats Caused by Ovalbumin
3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased ($P<0.01$ or $P<0.05$), and the low-dose group also showed a tendency to decrease.

TABLE 2

Effect of Composition 3 on symptom scores of allergic rhinitis in rats before and after dosing ($\bar{x} \pm s$)

| Groups | Number of animals | Dose (g crude drug/kg) | Before dosing | After dosing | | |
|---|---|---|---|---|---|---|
| | | | | Day 7 | Day 14 | Day 21 |
| Blank control group | 10 | — | $0.28 \pm 0.31$ | $0.39 \pm 0.30$ | $0.37 \pm 0.25$ | $0.35 \pm 0.21$ |
| Model control group | 10 | — | $6.91 \pm 1.80^{}$ | $6.73 \pm 1.49^{}$ | $7.04 \pm 1.72^{}$ | $6.96 \pm 1.49^{}$ |
| Bi-yan-kang group | 10 | 0.41 | $7.20 \pm 1.47^{**}$ | $3.49 \pm 1.03^{\Delta\Delta}$ | $3.81 \pm 1.20^{\Delta\Delta}$ | $3.41 \pm 1.20^{\Delta\Delta}$ |
| Test drug low-dose group | 10 | 1.0 | $6.91 \pm 1.25^{**}$ | $5.79 \pm 1.02$ | $6.28 \pm 1.39$ | $5.87 \pm 1.30$ |
| Test drug medium-dose group | 10 | 2.0 | $7.26 \pm 1.68^{**}$ | $5.36 \pm 1.19^{\Delta}$ | $5.51 \pm 1.40^{\Delta}$ | $3.97 \pm 1.35^{\Delta\Delta}$ |
| Test drug high-dose group | 10 | 6.0 | $7.05 \pm 1.50^{**}$ | $4.09 \pm 1.07^{\Delta\Delta}$ | $3.85 \pm 1.29^{\Delta\Delta}$ | $3.55 \pm 1.13^{\Delta\Delta}$ |

Note:
$^{**}P < 0.01$ vs. blank control group;
$^{\Delta}P < 0.05$,
$^{\Delta\Delta}P < 0.01$ vs. model group.

3.1.2 Effect of Composition 3 on Serum cAMP and cGMP Levels in Rats

Experimental results were shown in Table 3. As compared to the blank control group, the model group showed a significantly decreased serum cAMP level ($P<0.01$) and a significantly increased serum cGMP level ($P<0.01$). As compared to the model control group, the Bi-yan-kang group and all test drug groups showed a significantly increased serum cAMP level ($P<0.01$ or $P<0.05$); the Bi-yan-kang group and the test drug medium- and high-dose groups showed a significantly decreased serum cGMP level ($P<0.01$ or $P<0.05$), and the low dose group also showed a tendency to decrease.

3.1.3 Effect of Composition 3 on mast cells in rat nasal mucosa

The experimental results were shown in Table 3. The number of nasal mucosa mast cells in the model control group significantly increased with a highly significant difference ($P<0.01$). As compared to the model control group, the number of nasal mucosa mast cells in the Bi-yan-kang group and the test drug treatment groups all significantly decreased with a significant difference ($P<0.01$)

TABLE 3

Effect of Composition 3 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell count (cells) |
|---|---|---|---|---|---|
| Blank control group | — | 10 | $20.85 \pm 4.87$ | $9.45 \pm 2.31$ | $1.59 \pm 1.25$ |
| Model control group | — | 10 | $10.96 \pm 3.82^{}$ | $14.31 \pm 4.57^{}$ | $13.82 \pm 4.67^{**}$ |
| Bi-yan-kang group | 0.41 | 10 | $17.30 \pm 3.51^{\Delta\Delta}$ | $9.51 \pm 2.32^{\Delta\Delta}$ | $5.78 \pm 2.18^{\Delta\Delta}$ |
| Test drug low-dose group | 1.0 | 10 | $14.45 \pm 3.79$ | $12.98 \pm 3.81$ | $8.56 \pm 3.22^{\Delta\Delta}$ |
| Test drug medium-dose group | 2.0 | 10 | $15.37 \pm 5.21$ | $10.56 \pm 2.72^{\Delta}$ | $7.87 \pm 3.45^{\Delta\Delta}$ |
| Test drug high-dose group | 6.0 | 10 | $17.81 \pm 4.22^{\Delta\Delta}$ | $9.22 \pm 3.76^{\Delta\Delta}$ | $6.14 \pm 2.23^{\Delta\Delta}$ |

Note:
$^{*}P < 0.05$,
$^{**}P < 0.01$ vs. blank control group;
$^{\Delta}P < 0.05$,
$^{\Delta\Delta}P < 0.01$ vs. model group.

3.2 Effect of Composition 3 on Allergic Rhinitis in Guinea Pigs Caused by TDI 3.2.1 Effect on Guinea Pig Behaviors Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 3 on symptom scores of allergic rhinitis in guinea pigs before and after dosing ($\bar{x} \pm s$)

| Groups | Number of animals | Dose (g crude drug/kg) | Before dosing | After dosing Day 7 | After dosing Day 14 | After dosing Day 21 |
|---|---|---|---|---|---|---|
| Blank control group | 10 | — | 0.45 ± 0.28 | 0.47 ± 0.29 | 0.42 ± 0.21 | 0.35 ± 0.24 |
| Model control group | 10 | — | 6.78 ± 1.72** | 6.67 ± 1.27** | 6.73 ± 1.12** | 6.40 ± 0.96** |
| Bi-yan-kang group | 10 | 0.41 | 6.53 ± 1.59** | 5.64 ± 0.96$^\Delta$ | 5.48 ± 0.82$^\Delta$ | 4.87 ± 1.28$^\Delta$ |
| Test drug low-dose group | 10 | 1.0 | 6.34 ± 1.60** | 6.20 ± 1.25 | 6.15 ± 0.98 | 5.33 ± 1.22 |
| Test drug medium-dose group | 10 | 2.0 | 6.82 ± 1.87** | 5.83 ± 1.38$^\Delta$ | 5.76 ± 1.32$^{\Delta\Delta}$ | 4.90 ± 0.76$^{\Delta\Delta}$ |
| Test drug high-dose group | 10 | 6.0 | 6.79 ± 1.73** | 5.76 ± 1.17$^{\Delta\Delta}$ | 5.53 ± 0.84$^{\Delta\Delta}$ | 4.89 ± 0.93$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 3 was effective in treating allergic rhinitis by inhibiting the blood histamine level and serum IgE.

TABLE 5

Effect of Composition 3 on blood histamine and total serum IgE in guinea pigs ($\bar{x} \pm s$)

| Groups | Number of animals | Dose (g crude drug/kg) | Histamine fluorescence (mg · L) | IgE(IU · ml$^{-1}$) |
|---|---|---|---|---|
| Blank control group | 10 | — | 2.29 ± 0.48 | 0.132 ± 0.025 |
| Model control group | 10 | — | 3.16 ± 0.89** | 0.172 ± 0.032** |
| Bi-yan-kang group | 10 | 0.41 | 2.14 ± 0.54$^{\Delta\Delta}$ | 0.128 ± 0.025$^{\Delta\Delta}$ |
| Test drug low-dose group | 10 | 1.0 | 3.04 ± 0.44 | 0.165 ± 0.027 |
| Test drug medium-dose group | 10 | 2.0 | 2.62 ± 0.42$^\Delta$ | 0.143 ± 0.027$^\Delta$ |
| Test drug high-dose group | 10 | 6.0 | 2.39 ± 0.38$^{\Delta\Delta}$ | 0.136 ± 0.021$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.3 Effect on Eosinophils (EOS) in Nasal Secretion of Guinea Pigs

Experimental results were shown in Table 6. The number of eosinophils in the model group significantly increased (P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness significantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 3 on EOS in nasal secretion and nasal mucosa thickness in guinea pigs ($\bar{x} \pm s$)

| Groups | Dose (g crude drug/kg) | Number of animals | Number of EOS ($\times 10^{-9}$/L) | Mucosa thickness (mm) |
| --- | --- | --- | --- | --- |
| Blank control group | — | 10 | 2.77 ± 1.27 | 0.162 ± 0.054 |
| Model control group | — | 10 | 17.67 ± 4.08** | 0.295 ± 0.069** |
| Bi-yan-kang group | 0.41 | 10 | 9.30 ± 3.67$^{\Delta\Delta}$ | 0.196 ± 0.051$^{\Delta\Delta}$ |
| Test drug low-dose group | 1.0 | 10 | 11.08 ± 4.01$^{\Delta\Delta}$ | 0.235 ± 0.052$^{\Delta\Delta}$ |
| Test drug medium-dose group | 2.0 | 10 | 10.42 ± 3.46$^{\Delta\Delta}$ | 0.216 ± 0.056$^{\Delta\Delta}$ |
| Test drug high-dose group | 6.0 | 10 | 9.54 ± 2.76$^{\Delta\Delta}$ | 0.207 ± 0.072$^{\Delta\Delta}$ |

Note:
*$P < 0.05$,
**$P < 0.01$ vs. blank group;
$^{\Delta}P < 0.05$,
$^{\Delta\Delta}P < 0.01$ vs. model group.

4. Conclusion

The animal experimental studies demonstrate that the effectiveness of Composition 3 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 3 is effective in resisting allergic rhinitis.

Example 53. Animal Experiment Report of Composition 3 Obtained in Example 3 in Prevention and Treatment of Allergic Asthma 1. Materials and Methods
1.1 Sources of Samples The test drug was Composition 3 (Radix Panacis Quinquefolii, Ganoderma, and fermented *Cordyceps sinensis* powder) provided by Jiangzhong Pharmaceutical Co. Ltd. as composite powder. 1 g dry composite powder was equivalent to 11.41 g total crude drugs.

1.2 Laboratory Animals

SD rats, half of which were male and the other half female, each weighing 180 to 220 g, were provided by the Laboratory Animal Center, Jiangxi University of Traditional Chinese Medicine (SCXK (Jiangxi) 2006-0001). Guinea pigs, half of which were male and the other half female, each weighing 180 to 220 g, were from Dongchuang Experimental Animal Scientific Service Department, Kaifu District, Changsha, Hunan Province (Certification Number: SCXK (Hunan) 2006-0001).

1.3 Primary Reagents

Ovalbumin (OVA) (Sigma, batch No.: 025K0594); acetylcholine chloride (Shanghai Jingchun Reagent Co., Ltd., batch No.: 21205); histamine phosphate (Shanghai Jingchun Reagent Co., Ltd., batch No.: 22270); dexamethasone (Zhengzhou Zhuofeng Pharmaceuticals, batch No.: 0904213); IL-4 and IFN-γ ELISA kits (Great Wall Biochemicals).

1.4 Primary Instruments

MD3000 biological signal acquisition and analysis system (Huaibeizhenghua Bioinstrumentation Co., Ltd.); ZH-100 respiratory transducer (Huaibeizhenghua Bioinstrumentation Co., Ltd.); 402A1 ultrasonic atomizer (Jiangsu Juyue Medical Device Co., Ltd.); OLYMPUS microscope; TE2000-S inverted fluorescence phase contrast digital microscope (Nikon Inc., Japan); microtome (Leica, Germany).

2. Experimental Methods
2.1 Effect on Allergic Asthma in Rats Caused by OVA
2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on the low, medium, and high doses of Composition 3, with 10 animals in each group.

2.1.2 Establishment of Rat Allergic Asthma Animal Models

On day 1, all animals except those in the blank control group were sensitized by intraperitoneal injection with 1 ml suspension containing 10 mg OVA, 200 mg Al(OH)$_3$ dry powder, and $6 \times 10^9$ inactivated pertussis vaccines in physiological saline, and were sensitized once again on day 8. From day 15, all animal groups other than the black control group were challenged with ultrasonically atomized 1% OVA for about 20 min each time, at 8 a.m. to 9 a.m. in the morning on each day, until the rats showed asthmatic onsets, which lasted for 3 weeks. During the atomization challenging, the rats showed symptoms such as agitation, sneezing, urinary and fecal incontinence, scratching on ears, and cyanosis, suggesting successful replication of the asthma model.

2.1.3 Dosage Regime

The daily intake of the test drug Composition 3 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.76 mg dry powder/ml, 17.52 mg dry powder/ml, 52.56 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 3 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.

2.1.4 Recording the Latent Period of Asthma Induced in Rats

A ZH-100 respiratory transducer was tied around the thoracic cage of each rat (the tension was adjusted to about 1 to 2 g so that the amplitude of the respiratory wave was 1 to 2 my). The transducer was connected to a MD3000 biological signal acquisition and analysis system. The animals were placed in a closed glass bell jar connected with an ultrasonic atomizer. The acquisition system was turned on and a segment of normal respiratory wave was recorded. Then ultrasonic atomization with 1% OVA was applied for 20 min, and the respiratory waves of induced asthma in the rats were continuously recorded over 30 min after the atomization was initiated. Meanwhile, the period from the beginning of atomization to occurrence of symptoms (indicated by the first twitch) was visually observed and recorded as the latent period of asthma.

2.1.5 Measurements of IL-4 and IFN-γ Levels 24 h after the final challenge, the rats were anaesthetized by intraperitoneal injection with 3% sodium pentobarbital (30 mg/kg). 5 to 10 ml blood was drawn, and serum IL-4 and IFN-γ levels were measured by ELISA.

2.2 Effect on Allergic Asthma in Guinea Pigs Caused by a Mixed Gas of Ach and his 2.2.1 The same as in 2.1.1.

2.2.2 Establishment of Guinea Pig Allergic Asthma Animal Models

On day 1, guinea pigs were placed in a closed 4 L glass bell jar, into which a 1:1 mixture solution of 2% Ach and 0.4% His was sprayed by ultrasonic atomization for 15 s. After completion of spraying, the latent period of asthma induced in the guinea pigs was recorded (i.e., the period from the end of the spraying to asthmatic onsets, extreme difficulty in breathing till twitching and falling down). Animals having a latent period of asthma longer than 120 s were excluded.

2.2.3 Dosage Regime

The same as in 2.1.3.

2.2.4 Recording of Latent Period of Asthma

The same as in 2.1.4.1.

2.2.5 Measurement of IgE in Serum and BALF

Dual-antibody sandwich radioimmunoassay was employed.

2.3 Statistic Method

Experimental data were presented in $\bar{X} \pm S$. One-way ANOVA analysis was employed to compare the differences among the groups. $P<0.05$ was considered as significantly different. $P<0.01$ was considered as highly significantly different.

3. Results 3.1 Effect of Composition 3 on Allergic Asthma in Rats Caused by OVA 3.1.1 Effect on the Latent Period of Asthma Induced in Rats Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged ($P<0.05$ or $P<0.01$).

TABLE 1

Effect on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 76.03 ± 13.23** | 75.62 ± 11.65** |
| Positive control group | 10 | 0.5 mg/kg | 75.84 ± 12.36** | 162.61 ± 17.88$^{\Delta\Delta}$ |
| Test drug low-dose group | 10 | 1.0 | 76.42 ± 14.42** | 87.15 ± 19.82 |
| Test drug medium-dose group | 10 | 2.0 | 75.49 ± 15.38** | 93.56 ± 21.75$^{\Delta}$ |
| Test drug high-dose group | 10 | 6.0 | 74.07 ± 17.56** | 112.87 ± 21.78$^{\Delta\Delta}$ |

Note:
**$P < 0.01$ vs. blank group;
$^{\Delta}P < 0.05$,
$^{\Delta\Delta}P < 0.01$ vs. model group.

2.1.6 Measurement of EOS Content in Lung Tissues

The left lung tissues were cut off and fixed in 4% polyformaldehyde for 4 to 5 h, then washed with water, dehydrated with an alcohol gradient, and immersed and embedded in paraffine. HE staining was performed with a successive sectioning process, inflammatory changes in the tissues were observed, and EOS infiltration was counted. For each section, 10 fields were randomly chosen under a microscope at high magnification (×400) by the same observer, and the numbers of EOS infiltration around bronchus and vessels were calculated and averaged as the representative value for this section.

3.1.2 Effect on Serum IL-4 and IFN-γ Levels in Rats

Experimental results were shown in Table 2. As compared to the blank control group, the model group showed a significantly decreased serum IFN-γ level ($P<0.01$) but a significantly increased serum IL-4 level ($P<0.01$), indicating a severe imbalance of the IFN-γ/IL-4 ratio during asthma onsets. As compared to the model group, the dexamethasone group and the test drug medium- and high-dose groups all showed a significantly decreased IL-4 level ($P<0.05$ or $P<0.01$) and a significantly increased IFN-γ level ($P<0.05$ or $P<0.01$), indicating that the test drug can redress the imbalanced IFN-γ/IL-4 ratio.

TABLE 2

Effect of Composition 3 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.33 ± 2.43 | 26.35 ± 4.56 |
| Model control group | — | 10 | 23.06 ± 3.29** | 11.52 ± 3.24** |
| Positive control group | 0.5 mg/kg | 10 | 12.88 ± 4.13^ΔΔ | 20.51 ± 4.65^ΔΔ |
| Test drug low-dose group | 1.0 | 10 | 21.07 ± 3.08 | 12.83 ± 3.68 |
| Test drug medium-dose group | 2.0 | 10 | 18.64 ± 3.81^Δ | 15.24 ± 3.78^Δ |
| Test drug high-dose group | 6.0 | 10 | 15.94 ± 3.26^ΔΔ | 18.58 ± 4.67^ΔΔ |

Note:
**$P < 0.01$ vs. blank group;
$^{\Delta}P < 0.05$,
$^{\Delta\Delta}P < 0.01$ vs. model group.

3.1.3 Effect on the EOS Content in Rat Lung Tissues

Experimental results were shown in Table 3. The number of EOS in rats in the model group significantly increased ($P<0.01$). As compared to the model group, the positive control group and the test drug medium- and high-dose groups showed a significantly decreased number of EOS ($P<0.01$), indicating that Composition 3 is effective in treating allergic asthma possibly by reducing the EOS content in rat lung tissues.

TABLE 3

Effect of Composition 3 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | 5.76 ± 1.35 |
| Model control group | — | 10 | 108.85 ± 12.74** |
| Positive control group | 0.5 mg/kg | 10 | 27.51 ± 4.31^ΔΔ |
| Test drug low-dose group | 1.0 | 10 | 98.21 ± 10.28 |
| Test drug medium-dose group | 2.0 | 10 | 89.13 ± 9.24^ΔΔ |
| Test drug high-dose group | 6.0 | 10 | 67.01 ± 8.57^ΔΔ |

Note:
**$P < 0.01$ vs. blank group;
$^{\Delta\Delta}P < 0.01$ vs. model group.

3.2 Effect of Composition 3 on Allergic Asthma in Guinea Pigs Caused by a Mixed Gas of Ach and his 3.2.1 Effect on the Latent Period of Asthma Induced in Guinea Pigs Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged ($P<0.05$ or $P<0.01$), which indicates that Composition 3 greatly improves the asthmatic symptoms in guinea pigs.

TABLE 4

Effect of Composition 3 on the latent period of asthma induced in guinea pigs ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 74.84 ± 14.6** | 77.23 ± 11.61** |
| Positive control group | 10 | 0.5 mg/kg | 77.32 ± 13.95** | 160.92 ± 19.72^ΔΔ |
| Test drug low-dose group | 10 | 1.0 | 76.52 ± 14.86** | 90.31 ± 19.23 |
| Test drug medium-dose group | 10 | 2.0 | 75.58 ± 15.37** | 94.74 ± 21.68^Δ |
| Test drug high-dose group | 10 | 6.0 | 75.18 ± 1534** | 113.73 ± 21.91^ΔΔ |

Note:
**$P < 0.01$ vs. blank group;
$^{\Delta}P < 0.05$,
$^{\Delta\Delta}P < 0.01$ vs. model group.

3.2.2 Effect on the Total IgE in Serum and BALF of Guinea Pigs

Experimental results were shown in Table 5. The total IgE content in serum and BALF in the model group significantly increased ($P<0.01$). As compared to the model group, the total IgE contents in serum and BALF in the dexamethasone group and in the groups on the medium and high doses of the test drug all significantly decreased ($P<0.01$ or $P<0.05$), indicating that both dexamethasone and the test drug can inhibit allergic inflammatory response in guinea pig's lung and improve asthmatic symptoms.

TABLE 5

Effect of Composition 3 on the total IgE in serum and BALF of guinea pigs ($\bar{x} \pm s$)

| Groups | Dose (g crude drug/kg) | Number of animals | serum (U/L) | BALF (U/L) |
|---|---|---|---|---|
| Blank control group | — | 10 | 3.02 ± 0.93 | 3.55 ± 0.87 |
| Model control group | — | 10 | 5.47 ± 1.33** | 5.32 ± 1.71** |
| Positive control group | 0.5 mg/kg | 10 | 3.58 ± 1.19^ΔΔ | 3.49 ± 0.82^ΔΔ |
| Test drug low-dose group | 1.0 | 10 | 5.24 ± 2.27 | 4.28 ± 1.44 |
| Test drug medium-dose group | 2.0 | 10 | 4.15 ± 1.14^Δ | 3.84 ± 1.42^Δ |
| Test drug high-dose group | 6.0 | 10 | 3.85 ± 1.12^ΔΔ | 3.12 ± 0.82^ΔΔ |

Note:
**$P < 0.01$ vs. blank group;
$^{\Delta}P < 0.05$,
$^{\Delta\Delta}P < 0.01$ vs. model group.

3.2.3 Effect on the EOS Content in Guinea Pigs' Lung Tissues

Experimental results were shown in Table 6. As compared to the blank control group, the level of EOS counts in guinea pigs in the model group significantly increased ($P<0.01$). As compared to the model group, the level of EOS counts in the positive control group and the test drug medium- and high-dose groups significantly decreased ($P<0.01$), indicating that Composition 3 is effective in treating allergic asthma possibly by decreasing the EOS content in guinea pigs' lung tissues.

TABLE 6

Effect of Composition 3 on the EOS content in guinea pigs' lung tissues
($\bar{x} \pm s$)

| Groups | Dose (g crude drug/kg) | Number of animals | EOS (cells/HP) |
|---|---|---|---|
| Blank control group | — | 10 | 4.24 ± 2.49 |
| Model control group | — | 10 | 97.61 ± 14.82** |
| Positive control group | 0.5 mg/kg | 10 | 31.78 ± 7.55$^{\triangle\triangle}$ |
| Test drug low-dose group | 1.0 | 10 | 88.28 ± 12.18 |
| Test drug medium-dose group | 2.0 | 10 | 77.25 ± 12.14$^{\triangle\triangle}$ |
| Test drug high-dose group | 6.0 | 10 | 61.24 ± 11.68$^{\triangle\triangle}$ |

Note:
**P < 0.01 vs. blank group;
$\triangle\triangle$P < 0.01 vs. model group.

4. Conclusion

The animal experimental studies demonstrate that Composition 3 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 3 is considered effective in resisting allergic asthma.

Example 54. Animal Experiment Report of Composition 4 Obtained in Example 4 Against Allergy and Allergic Dermatitis 1. Materials and Methods
1.1 Sources of Samples The test drug was Composition 4 (Radix Panacis Quinquefolii, Ganoderma, and Cordyceps) provided by Jiangzhong Pharmaceutical Co. Ltd. as composite powder. 1 g dry composite powder was equivalent to 10.97 g total crude drugs. Its daily intake recommended for one person was 24 g crude drug/60 kg body weight.
1.2 Laboratory Animals
The same as in Example 51.
1.3 Primary Reagents
The same as in Example 51.
1.4 Primary Instruments
The same as in Example 51.
2. Experimental Methods
2.1 Animal Grouping Animals were randomly divided into groups with 10 animals per group based on the body weights. A model control group, groups on the low, medium and high doses of Composition 4, and a positive drug control group (prednisone) were established.
2.2 Dosage Regime The daily intake of test drug Composition 4 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (18.23 mg dry powder/ml, 36.46 mg dry powder/ml, and 109.38 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (9.12 mg dry powder/ml, 18.23 mg dry powder/ml, and 54.69 mg dry powder/ml) with distilled water to carry out experiments.
2.3 Effect of Composition 4 on Passive Anaphylaxis (PCA) in Rats Caused by Ovalbumin
2.3.1 Preparation of Antiserum
The same as in Example 51.
2.3.2 Establishment of Rat Anti-Ovalbumin Serum Models Anti-ovalbumin serum was taken and diluted at 1:4 or 1:8 with physiological saline. 50 rats were randomly divided into 5 groups, i.e., a model control group, groups on the low, medium and high doses of Composition 4, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 4 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].
2.3.3 Effect of Composition 4 on Delayed Hypersensitivity in Mouse Auricle Skin Caused by 2,4-dinitrochlorobenzene[4]

50 mice were randomly divided into 5 groups, i.e., a model control group, groups on the low, medium and high doses of Composition 4, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 4 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 4 on Local Itching in Mice Caused by Low-Molecular-Weight Dextran[5]

The mice were randomly divided into 5 groups, i.e., a model control group, groups on the low, medium and high doses of Composition 4, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 4 on Capillary Permeability in Rats[6]

The rats were randomly divided into 5 groups, i.e., a model control group, groups on the low, medium and high doses of Composition 4, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 4 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

Experimental data were presented in $\bar{X} \pm S$. One-way ANOVA analysis was employed to compare the differences among the model control group and the groups on various doses of Composition 4. $P<0.05$ was considered as significantly different. $P<0.01$ was considered as highly significantly different.

3. Results 3.1 Effect of Composition 4 on Passive Anaphylaxis in Rats

Test results were shown in Tables 1 and 2. As compared to the model control group, the low dose group on Composition 4 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 4 all showed an effect of significantly decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 4 had a significant inhibitory effect on passive anaphylaxis in rats.

TABLE 1

Effect of Composition 4 on the diameter of PCA blue spots in rats ($\bar{x} \pm s$)

| Groups | Dose (g crude drug/kg) | Number of animals | Diameter of blue spots (mm) 1:4 | 1:8 |
|---|---|---|---|---|
| Model control group | 0.0 | 10 | 17.22 ± 2.57 | 10.62 ± 2.12 |
| Positive control group | 5.0 mg | 10 | 11.94 ± 1.90** | 7.23 ± 1.60** |
| Test drug low-dose group | 1.2 | 10 | 15.68 ± 1.58 | 9.36 ± 1.48 |
| Test drug medium-dose group | 2.4 | 10 | 14.80 ± 2.10* | 8.50 ± 1.62* |
| Test drug high-dose group | 7.2 | 10 | 13.62 ± 2.07** | 7.56 ± 1.70** |

*$P < 0.05$,
**$P < 0.01$ vs. model control group.

TABLE 2

Effect of Composition 4 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Model control group | 0.0 | 10 | 57.92 ± 9.65 | 4.17 ± 0.79 |
| Positive control group | 5.0 mg | 10 | 19.46 ± 8.72** | 1.92 ± 0.61** |
| Test drug low-dose group | 1.2 | 10 | 49.27 ± 9.05 | 3.58 ± 0.88 |
| Test drug medium-dose group | 2.4 | 10 | 46.48 ± 8.27* | 3.10 ± 0.92* |
| Test drug high-dose group | 7.2 | 10 | 29.31 ± 7.99** | 2.62 ± 0.76** |

*$P < 0.05$,
**$P < 0.01$ vs. model control group.

3.2 Effect of Composition 4 on Delayed Hypersensitivity in Mouse Auricle Skin Caused by 2,4-dinitrochlorobenzene The results were shown in Table 3. As compared to the model control group, the swelling degree of mouse auricle discs significantly decreased in the groups on the medium and high doses of Composition 4, indicating that Composition 4 had a good inhibitory effect on delayed hypersensitivity in mouse auricle skin caused by 2,4-dinitrochlorobenzene.

TABLE 3

Effect of Composition 4 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Model control group | 0.0 | 10 | 6.20 ± 0.90 |
| Positive control group | 5.0 mg | 10 | 4.22 ± 0.96** |
| Test drug low-dose group | 2.0 | 10 | 5.62 ± 0.87 |
| Test drug medium-dose group | 4.0 | 10 | 5.08 ± 0.94* |
| Test drug high-dose group | 12.0 | 10 | 4.60 ± 0.80** |

*$P < 0.05$,
**$P < 0.01$ vs. model control group.

3.3 Effect of Composition 4 on Local Itching in Mice Caused by Low-Molecular-Weight Dextran The test results were shown in Table 4. As compared to the model control group, the OD value significantly decreased in the rat groups on the medium and high doses of Composition 4, indicating that Composition 4 was significantly effective in decreasing the capillary permeability increase in rats caused by histamine phosphate.

TABLE 4

Effect of Composition 4 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 34.12 ± 9.54 |
| Positive control group | 5.0 mg | 10 | 14.25 ± 6.72** |
| Test drug low-dose group | 2.0 | 10 | 29.46 ± 8.03 |
| Test drug medium-dose group | 4.0 | 10 | 22.53 ± 9.50* |
| Test drug high-dose group | 12.0 | 10 | 18.12 ± 8.26** |

*$P < 0.05$,
**$P < 0.01$ vs. model control group.

3.4 Effect of Composition 4 on Capillary Permeability in Rats

The test results were shown in Table 5. As compared to the model control group, the OD value significantly decreased in the rat groups on the medium and high doses of Composition 4, indicating that Composition 4 was significantly effective in decreasing the capillary permeability increase in rats caused by histamine phosphate.

TABLE 5

Effect of Composition 4 on capillary permeability in rats ($\bar{x} \pm s$)

| Groups | Dose (g crude drug/kg) | Number of animals | OD value |
|---|---|---|---|
| Model control group | 0.0 | 10 | 0.978 ± 0.104 |
| Positive control group | 5.0 mg | 10 | 0.656 ± 0.088** |
| Test drug low-dose group | 1.2 | 10 | 0.924 ± 0.096 |
| Test drug medium-dose group | 2.4 | 10 | 0.851 ± 0.108* |
| Test drug high-dose group | 7.2 | 10 | 0.776 ± 0.122** |

*$P < 0.05$,
**$P < 0.01$ vs. model control group.

4. Conclusion

The animal experimental studies demonstrate that Composition 4 is significantly effective in inhibiting passive anaphylaxis in rats caused by ovalbumin, that Composition 4 is effective in inhibiting delayed hypersensitivity in mouse auricle skin caused by 2,4-dinitrochlorobenzene, and that Composition 4 is significantly effective in decreasing the capillary permeability increase in rats caused by histamine phosphate. The above results indicate good effectiveness of Composition 4 in resisting allergy and in preventing and treating allergic diseases such as allergic dermatitis and urticaria.

Example 55. Animal Experiment Report of Composition 4 Obtained in Example 4 in Prevention and Treatment of Allergic Rhinitis 1. Materials and Methods
1.1 Sources of Samples The test drug was Composition 4 (Radix Panacis Quinquefolii, Ganoderma, and Cordyceps) provided by Jiangzhong Pharmaceutical Co. Ltd. as composite powder. 1 g dry composite powder was equivalent to 10.97 g total crude drugs.
1.2 Laboratory Animals
The same as in Example 52.
1.3 Primary Reagents
The same as in Example 52.
1.4 Primary Instruments
The same as in Example 52.
2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on the low, medium and high doses of Composition 4, with 10 animals in each group.
2.1.2 Dosage Regime The daily intake of the test drug Composition 4 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. The volume of intragastric administration was calculated as 1.0 ml/100 g body weight. The blank control group and the allergic rhinitis model group were intragastrically given an equivalent volume of physiological saline; the Bi-yan-kang group was given the drug at a dose of 410 mg/kg. The intragastric administration was initiated after a successful modeling and carried out once per day for 21 consecutive days.
2.1.3 Establishment of Rat Allergic Rhinitis Animal Models
The same as in Example 52.
2.1.4 Assay Indicators
The same as in Example 52.
2.1.4.1 Blood cAMP and cGMP Measurement
The same as in Example 52.
2.1.4.2 Nasal Mucosal Mast Cell Counting
The same as in Example 52.
2.2 Effect on Allergic Rhinitis in Guinea Pigs Caused by TDI
2.2.1. The Same as in 2.1.1.
2.2.2. The Same as in 2.1.2.
2.2.3 Establishment of Guinea Pig Allergic Rhinitis Animal Models
The same as in Example 52.
2.2.4 Assay Indicators
The same as in Example 52.
2.2.4.1 Guinea Pig Behavior Observation
The same as in Example 52.
2.2.4.2 Counts of Eosinophils (EOS) in Nasal Secretion
The same as in Example 52.
2.2.4.3 Total Serum IgE and Blood Histamine Measurement
The same as in Example 52.

2.2.4.4 Nasal Mucosa Thickness Measurement

The same as in Example 52.

2.3 Statistic Method

Experimental data were presented in $\bar{X} \pm S$. One-way ANOVA analysis was employed to compare the differences among the blank control group, the model control group and the groups on various doses of Composition 4. $P<0.05$ was considered as significantly different. $P<0.01$ was considered as highly significantly different.

3. Results 3.1 Effect of Composition 4 on Allergic Rhinitis in Rats Caused by Ovalbumin 3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased ($P<0.01$ or $P<0.05$), and the low-dose group also showed a tendency to decrease.

TABLE 2

Effect of Composition 4 on symptom scores of allergic rhinitis in rats before and after dosing ($\bar{x} \pm s$)

| Groups | Number of animals | Dose (g crude drug/kg) | Before dosing | After dosing | | |
|---|---|---|---|---|---|---|
| | | | | Day 7 | Day 14 | Day 21 |
| Blank control group | 10 | — | 0.35 ± 0.31 | 0.40 ± 0.22 | 0.37 ± 0.19 | 0.33 ± 0.14 |
| Model control group | 10 | — | 6.68 ± 1.52** | 6.60 ± 1.27** | 6.90 ± 1.32** | 6.54 ± 1.16** |
| Bi-yan-kang group | 10 | 0.41 | 6.63 ± 1.24** | 3.24 ± 0.96$^{\Delta\Delta}$ | 3.67 ± 1.24$^{\Delta\Delta}$ | 2.96 ± 0.98$^{\Delta\Delta}$ |
| Test drug low-dose group | 10 | 1.0 | 6.74 ± 1.15** | 5.80 ± 0.85 | 5.76 ± 1.39 | 5.61 ± 1.06 |
| Test drug medium-dose group | 10 | 2.0 | 6.52 ± 1.34** | 5.27 ± 1.23$^{\Delta}$ | 5.29 ± 1.43$^{\Delta}$ | 4.56 ± 1.45$^{\Delta\Delta}$ |
| Test drug high-dose group | 10 | 6.0 | 6.69 ± 1.08** | 4.66 ± 0.82$^{\Delta\Delta}$ | 4.40 ± 1.36$^{\Delta\Delta}$ | 4.24 ± 1.33$^{\Delta\Delta}$ |

Note:
**$P < 0.01$ vs. blank control group;
$^{\Delta}P < 0.05$,
$^{\Delta\Delta}P < 0.01$ vs. model group.

3.1.2 Effect of Composition 4 on Serum cAMP and cGMP Levels in Rats

Experimental results were shown in Table 3. As compared to the blank control group, the model group showed a significantly decreased serum cAMP level ($P<0.01$) and a significantly increased serum cGMP level ($P<0.01$). As compared to the model control group, the Bi-yan-kang group and all test drug groups showed a significantly increased serum cAMP level ($P<0.01$ or $P<0.05$); the Bi-yan-kang group and the test drug medium- and high-dose groups showed a significantly decreased serum cGMP level ($P<0.01$ or $P<0.05$), and the low dose group also showed a tendency to decrease.

3.1.3 Effect of Composition 4 on Mast Cells in Rat Nasal Mucosa

The experimental results were shown in Table 3. The number of nasal mucosa mast cells in the model control group significantly increased with a highly significant difference ($P<0.01$). As compared to the model control group, the number of nasal mucosa mast cells in the Bi-yan-kang group and the test drug treatment groups all significantly decreased with a significant difference ($P<0.01$)

TABLE 3

Effect of Composition 4 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell count (cells) |
|---|---|---|---|---|---|
| Blank control group | — | 10 | 20.05 ± 4.97 | 9.80 ± 2.66 | 1.70 ± 1.39 |
| Model control group | — | 10 | 10.30 ± 3.88** | 14.85 ± 4.86** | 14.29 ± 4.73** |

TABLE 3-continued

Effect of Composition 4 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell count (cells) |
|---|---|---|---|---|---|
| Bi-yan-kang group | 0.41 | 10 | 18.30 ± 3.59$^{\Delta\Delta}$ | 9.00 ± 2.46$^{\Delta\Delta}$ | 5.86 ± 2.19$^{\Delta\Delta}$ |
| Test drug low-dose group | 1.0 | 10 | 14.15 ± 3.90$^{\Delta}$ | 12.45 ± 3.95 | 8.91 ± 3.47$^{\Delta\Delta}$ |
| Test drug medium-dose group | 2.0 | 10 | 15.85 ± 5.24$^{\Delta}$ | 10.60 ± 2.82$^{\Delta}$ | 7.77 ± 3.21$^{\Delta\Delta}$ |
| Test drug high-dose group | 6.0 | 10 | 16.75 ± 4.09$^{\Delta\Delta}$ | 9.20 ± 3.96$^{\Delta\Delta}$ | 6.54 ± 2.06$^{\Delta\Delta}$ |

Note:
*P < 0.05,
**P < 0.01 vs. blank group;
$^{\Delta}$P < 0.05,
$^{\Delta\Delta}$P < 0.01 vs. model group.

3.2 Effect of Composition 4 on Allergic Rhinitis in Guinea Pigs Caused by TDI 3.2.1 Effect on Guinea Pig Behaviors Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 4 on symptom scores of allergic rhinitis in guinea pigs before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.55 ± 0.71 | 0.49 ± 0.22 | 0.37 ± 0.29 | 0.43 ± 0.64 |
| Model control group | 10 | — | 6.28 ± 1.22** | 6.47 ± 1.17** | 6.54 ± 1.02** | 6.00 ± 0.96** |
| Bi-yan-kang group | 10 | 0.41 | 6.63 ± 1.09** | 5.34 ± 0.86$^{\Delta}$ | 5.34 ± 0.92$^{\Delta}$ | 4.77 ± 1.28$^{\Delta}$ |
| Test drug low-dose group | 10 | 1.0 | 6.54 ± 1.30** | 5.30 ± 1.35 | 5.69 ± 0.98 | 5.03 ± 1.32 |
| Test drug medium-dose group | 10 | 2.0 | 6.42 ± 1.07** | 5.03 ± 1.28$^{\Delta}$ | 4.76 ± 1.32$^{\Delta\Delta}$ | 4.50 ± 0.77$^{\Delta\Delta}$ |
| Test drug high-dose group | 10 | 6.0 | 6.69 ± 1.13** | 4.56 ± 1.07$^{\Delta\Delta}$ | 3.93 ± 0.84$^{\Delta\Delta}$ | 3.67 ± 0.93$^{\Delta\Delta}$ |

Note:
*P < 0.05,
**P < 0.01 vs. blank group;
$^{\Delta}$P < 0.05,
$^{\Delta\Delta}$P < 0.01 vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 4 was effective in treating allergic rhinitis by inhibiting the blood histamine level and serum IgE.

TABLE 5

Effect of Composition 4 on blood histamine and total serum IgE in guinea pigs ($\bar{x} \pm s$)

| Groups | Number of animals | Dose (g crude drug/kg) | Histamine fluorescence (mg · L) | IgE(IU · ml$^{-1}$) |
|---|---|---|---|---|
| Blank control group | 10 | — | 2.09 ± 0.40 | 0.123 ± 0.022 |
| Model control group | 10 | — | 3.15 ± 0.90** | 0.162 ± 0.034** |
| Bi-yan-kang group | 10 | 0.41 | 2.13 ± 0.47$^{\Delta\Delta}$ | 0.122 ± 0.024$^{\Delta\Delta}$ |
| Test drug low-dose group | 10 | 1.0 | 3.00 ± 0.45 | 0.136 ± 0.028 |
| Test drug medium-dose group | 10 | 2.0 | 2.32 ± 0.42$^{\Delta}$ | 0.128 ± 0.025$^{\Delta}$ |

TABLE 5-continued

Effect of Composition 4 on blood histamine and total serum IgE in guinea pigs ($\bar{x} \pm s$)

| Groups | Number of animals | Dose (g crude drug/kg) | Histamine fluorescence (mg · L) | IgE(IU · ml$^{-1}$) |
|---|---|---|---|---|
| Test drug high-dose group | 10 | 6.0 | 2.12 ± 0.38$^{\Delta\Delta}$ | 0.120 ± 0.010$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.3 Effect on Eosinophils (EOS) in Nasal Secretion of Guinea Pigs

Experimental results were shown in Table 6. The number of eosinophils in the model group significantly increased (P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness significantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 4 on EOS in nasal secretion and nasal mucosa thickness in guinea pigs ($\bar{x} \pm s$)

| Groups | Dose (g crude drug/kg) | Number of animals | Number of EOS (×10$^{-9}$/L) | Mucosa thickness (mm) |
|---|---|---|---|---|
| Blank control group | — | 10 | 2.67 ± 1.37 | 0.158 ± 0.051 |
| Model control group | — | 10 | 18.67 ± 4.18** | 0.285 ± 0.072** |
| Bi-yan-kang group | 0.41 | 10 | 9.29 ± 3.80$^{\Delta\Delta}$ | 0.198 ± 0.049$^{\Delta\Delta}$ |
| Test drug low-dose group | 1.0 | 10 | 13.28 ± 4.11$^{\Delta\Delta}$ | 0.215 ± 0.048$^{\Delta\Delta}$ |
| Test drug medium-dose group | 2.0 | 10 | 11.42 ± 3.56$^{\Delta\Delta}$ | 0.196 ± 0.069$^{\Delta\Delta}$ |
| Test drug high-dose group | 6.0 | 10 | 10.14 ± 2.86$^{\Delta\Delta}$ | 0.187 ± 0.061$^{\Delta\Delta}$ |

Note:
*P < 0.05,
**P < 0.01 vs. blank group;
$^\Delta$P < 0.05,
$^{\Delta\Delta}$P < 0.01 vs. model group.

4. Conclusion

The animal experimental studies demonstrate that the effectiveness of Composition 4 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 4 is effective in resisting allergic rhinitis.

Example 56. Animal Experiment Report of Composition 4 Obtained in Example 4 in Prevention and Treatment of Allergic Asthma 1. Materials and Methods
1.1 Sources of Samples The test drug was Composition 4 (Radix Panacis Quinquefolii, Ganoderma, and Cordyceps) provided by Jiangzhong Pharmaceutical Co. Ltd. as composite powder. 1 g dry composite powder was equivalent to 10.97 g total crude drugs.

1.2 Laboratory Animals
The same as in Example 53.
1.3 Primary Reagents
The same as in Example 53.
1.4 Primary Instruments
The same as in Example 53.
2. Experimental Methods
2.1 Effect on Allergic Asthma in Rats Caused by OVA
2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on the low, medium and high doses of Composition 4, with 10 animals in each group.

2.1.2 Establishment of Rat Allergic Asthma Animal Models
The same as in Example 53.
2.1.3 Dosage Regime The daily intake of the test drug Composition 4 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (9.12 mg dry powder/ml, 18.23 mg dry powder/ml, 54.69 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 4 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.

2.1.4 Recording of Latent Period of Asthma in Rats
The same as in Example 53.
2.1.5 Measurements of IL-4 and IFN-γ Levels
The same as in Example 53.

2.1.6 Measurement of EOS Content in Lung Tissues

The same as in Example 53.

2.2 Effect on Allergic Asthma in Guinea Pigs Caused by a Mixed Gas of Ach and His 2.2.1. The Same as in 2.1.1.

2.2.2 Establishment of Guinea Pig Allergic Asthma Animal Models

The same as in Example 53.

2.2.3 Dosage Regime

The same as in 2.1.3.

2.2.4 Recording of Latent Period of Asthma

The same as in 2.1.4.1.

2.2.5 Measurement of IgE in Serum and BALF

The same as in Example 53.

2.3 Statistic Method

The same as in Example 53.

3 Results 3.1 Effect of Composition 4 on Allergic Asthma in Rats Caused by OVA 3.1.1 Effect on the Latent Period of Asthma Induced in Rats Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged ($P<0.05$ or $P<0.01$).

TABLE 1

Effect of Composition 4 on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 77.24 ± 13.82** | 75.54 ± 12.86** |
| Positive control group | 10 | 0.5 mg/kg | 74.66 ± 11.09** | 159.77 ± 20.28$^{\Delta\Delta}$ |
| Test drug low-dose group | 10 | 1.0 | 75.63 ± 15.30** | 85.03 ± 21.32 |
| Test drug medium-dose group | 10 | 2.0 | 78.52 ± 14.07** | 96.50 ± 23.65$^{\Delta}$ |
| Test drug high-dose group | 10 | 6.0 | 78.59 ± 17.13** | 102.67 ± 23.87$^{\Delta\Delta}$ |

Note:
**$P < 0.01$ vs. blank group;
$^{\Delta}P < 0.05$,
$^{\Delta\Delta}P < 0.01$ vs. model group.

3.1.2 Effect on Serum IL-4 and IFN-γ Levels in Rats

Experimental results were shown in Table 2. As compared to the blank control group, the model group showed a significantly decreased serum IFN-γ level ($P<0.01$) but a significantly increased serum IL-4 level ($P<0.01$), indicating a severe imbalance of the IFN-γ/IL-4 ratio during asthma onsets. As compared to the model group, the dexamethasone group and the test drug medium- and high-dose groups all showed a significantly decreased IL-4 level ($P<0.05$ or $P<0.01$) and a significantly increased IFN-γ level ($P<0.05$ or $P<0.01$), indicating that the test drug can redress the imbalanced IFN-γ/IL-4 ratio.

TABLE 2

Effect of Composition 4 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.72 ± 2.53 | 24.31 ± 4.17 |
| Model control group | — | 10 | 22.45 ± 3.58** | 11.85 ± 3.46** |
| Positive control group | 0.5 mg/kg | 10 | 13.51 ± 4.31$^{\Delta\Delta}$ | 20.26 ± 4.86$^{\Delta\Delta}$ |
| Test drug low-dose group | 1.0 | 10 | 20.57 ± 3.18 | 13.78 ± 3.77 |
| Test drug medium-dose group | 2.0 | 10 | 18.25 ± 4.14$^{\Delta}$ | 15.60 ± 3.82$^{\Delta}$ |
| Test drug high-dose group | 6.0 | 10 | 16.12 ± 3.37$^{\Delta\Delta}$ | 17.36 ± 4.96$^{\Delta\Delta}$ |

Note:
**$P < 0.01$ vs. blank group;
$^{\Delta}P < 0.05$,
$^{\Delta\Delta}P < 0.01$ vs. model group.

3.1.3 Effect on the EOS Content in Rat Lung Tissues

Experimental results were shown in Table 3. The number of EOS in rats in the model group significantly increased ($P<0.01$). As compared to the model group, the positive control group and the test drug medium- and high-dose groups showed a significantly decreased number of EOS ($P<0.01$), indicating that Composition 4 is effective in treating allergic asthma possibly by reducing the EOS content in rat lung tissues.

TABLE 3

Effect of Composition 4 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | 2.24 ± 0.85 |
| Model control group | — | 10 | 103.60 ± 13.94** |
| Positive control group | 0.5 mg/kg | 10 | 28.39 ± 4.26$^{\Delta\Delta}$ |
| Test drug low-dose group | 1.0 | 10 | 93.21 ± 11.29 |
| Test drug medium-dose group | 2.0 | 10 | 78.13 ± 10.34$^{\Delta\Delta}$ |
| Test drug high-dose group | 6.0 | 10 | 65.22 ± 8.49$^{\Delta\Delta}$ |

Note:
**$P < 0.01$ vs. blank group;
$^{\Delta\Delta}P < 0.01$ vs. model group.

3.2 Effect of Composition 4 on Allergic Asthma in Guinea Pigs Caused by a Mixed Gas of Ach and his 3.2.1 Effect on the Latent Period of Asthma Induced in Guinea Pigs Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged ($P<0.05$ or $P<0.01$), which indicates that Composition 4 greatly improves the asthmatic symptoms in guinea pigs.

TABLE 4

Effect of Composition 4 on the latent period of asthma induced in guinea pigs ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 76.18 ± 10.82** | 77.00 ± 10.96** |
| Positive control group | 10 | 0.5 mg/kg | 75.63 ± 9.09** | 155.77 ± 16.28$^{\Delta\Delta}$ |
| Test drug low-dose group | 10 | 1.0 | 76.54 ± 14.30** | 83.03 ± 21.32 |
| Test drug medium-dose group | 10 | 2.0 | 77.82 ± 15.07** | 97.50 ± 24.77$^{\Delta}$ |
| Test drug high-dose group | 10 | 6.0 | 79.69 ± 19.13** | 110.67 ± 24.93$^{\Delta\Delta}$ |

Note:
**P < 0.01 vs. blank group;
$^{\Delta}$P < 0.05,
$^{\Delta\Delta}$P < 0.01 vs. model group.

3.2.2 Effect on the Total IgE in Serum and BALF of Guinea Pigs

Experimental results were shown in Table 5. The total IgE content in serum and BALF in the model group significantly increased (P<0.01). As compared to the model group, the total IgE contents in serum and BALF in the dexamethasone group and in the groups on the medium and high doses of the test drug all significantly decreased (P<0.01 or P<0.05), indicating that both dexamethasone and the test drug can inhibit allergic inflammatory response in guinea pig's lung and improve asthmatic symptoms.

TABLE 5

Effect of Composition 4 on the total IgE in serum and BALF of guinea pigs ($\bar{x} \pm s$)

| Groups | Dose (g crude drug/kg) | Number of animals | Serum (U/L) | BALF (U/L) |
|---|---|---|---|---|
| Blank control group | — | 10 | 2.04 ± 0.83 | 3.61 ± 0.84 |
| Model control group | — | 10 | 5.62 ± 1.37** | 5.32 ± 1.24** |
| Positive control group | 0.5 mg/kg | 10 | 3.75 ± 1.31$^{\Delta\Delta}$ | 3.72 ± 0.72$^{\Delta\Delta}$ |
| Test drug low-dose group | 1.0 | 10 | 5.11 ± 2.18 | 4.15 ± 1.57 |
| Test drug medium-dose group | 2.0 | 10 | 4.25 ± 1.14$^{\Delta}$ | 3.92 ± 1.45$^{\Delta}$ |
| Test drug high-dose group | 6.0 | 10 | 4.01 ± 1.09$^{\Delta\Delta}$ | 3.89 ± 0.96$^{\Delta\Delta}$ |

Note:
**P < 0.01 vs. blank group;
$^{\Delta}$P < 0.05,
$^{\Delta\Delta}$P < 0.01 vs. model group.

3.2.3 Effect on the EOS Content in Guinea Pigs' Lung Tissues

Experimental results were shown in Table 6. As compared to the blank control group, the level of EOS counts in guinea pigs in the model group significantly increased (P<0.01). As compared to the model group, the level of EOS counts in the positive control group and the test drug medium- and high-dose groups significantly decreased (P<0.01), indicating that Composition 4 is effective in treating allergic asthma possibly by decreasing the EOS content in guinea pigs' lung tissues.

TABLE 6

Effect of Composition 4 on the EOS content in guinea pigs' lung tissues ($\bar{x} \pm s$)

| Groups | Dose (g crude drug/kg) | Number of animals | EOS (cells/HP) |
|---|---|---|---|
| Blank control group | — | 10 | 5.24 ± 2.85 |
| Model control group | — | 10 | 93.60 ± 14.94** |
| Positive control group | 0.5 mg/kg | 10 | 30.79 ± 7.25$^{\Delta\Delta}$ |
| Test drug low-dose group | 1.0 | 10 | 82.28 ± 12.19 |
| Test drug medium-dose group | 2.0 | 10 | 70.25 ± 12.04$^{\Delta\Delta}$ |
| Test drug high-dose group | 6.0 | 10 | 59.22 ± 11.69$^{\Delta\Delta}$ |

Note:
**P < 0.01 vs. blank group;
$^{\Delta\Delta}$P < 0.01 vs. model group.

4. Conclusion

The animal experimental studies demonstrate that Composition 4 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 4 is considered effective in resisting allergic asthma.

Example 57. Animal Experiment Report of Composition 5 Obtained in Example 5 Against Allergy and Allergic Dermatitis 1. Materials and Methods
1.1 Sources of Samples The test drug was Composition 5 (Radix Panacis Quinquefolii, Ganoderma, fermented *Cordyceps sinensis* powder and Cordyceps) provided by Jiangzhong Pharmaceutical Co. Ltd. as composite powder. 1 g dry composite powder was equivalent to 12.39 g total crude drugs. Its daily intake recommended for one person was 24 g crude drug/60 kg body weight.

1.2 Laboratory Animals
The same as in Example 51.
1.3 Primary Reagents
The same as in Example 51.
1.4 Primary Instruments
The same as in Example 51.
2. Experimental Methods
2.1 Animal Grouping Animals were randomly divided into groups with 10 animals per group based on the body weights. A model control group, groups on the low, medium and high doses of Composition 5, and a positive drug control group (prednisone) were established.

2.2 Dosage Regime

The daily intake of test drug Composition 5 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (16.14 mg dry powder/ml, 32.28 mg dry powder/ml, and 96.84 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.08 mg dry powder/ml, 16.14 mg dry powder/ml, and 48.42 mg dry powder/ml) with distilled water to carry out experiments.

2.3 Effect of Composition 5 on Passive Anaphylaxis (PCA) in Rats Caused by Ovalbumin
2.3.1 Preparation of Antiserum
The same as in Example 51.
2.3.2 Establishment of Rat Anti-Ovalbumin Serum Models[1]

Anti-ovalbumin serum was taken and diluted at 1:4 or 1:8 with physiological saline.

50 rats were randomly divided into 5 groups, i.e., a model control group, groups on the low, medium and high doses of Composition 5, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 5 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].

2.3.3 Effect of Composition 5 on Delayed Hypersensitivity in Mouse Auricle Skin Caused by 2,4-Dinitrochlorobenzene[4]

The mice were randomly divided into 5 groups, i.e., a model control group, groups on the low, medium and high doses of Composition 5, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 5 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 5 on Local Itching in Mice Caused by Low-Molecular-Weight Dextran[5]

The mice were randomly divided into 5 groups, i.e., a model control group, groups on the low, medium and high doses of Composition 5, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 5 on Capillary Permeability in Rats[6]

The rats were randomly divided into 5 groups, i.e., a model control group, groups on the low, medium and high doses of Composition 5, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 5 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

Experimental data were presented in $\bar{X}\pm S$. One-way ANOVA analysis was employed to compare the differences among the model control group and the groups on various doses of Composition 5. $P<0.05$ was considered as significantly different. $P<0.01$ was considered as highly significantly different.

3. Results 3.1 Effect of Composition 5 on Passive Anaphylaxis in Rats

Test results were shown in Tables 1 and 2. As compared to the model control group, the low dose group on Composition 5 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 5 all showed an effect of significantly decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 5 had a significant inhibitory effect on passive anaphylaxis in rats.

3.2 Effect of Composition 5 on Delayed Hypersensitivity in Mouse Auricle Skin Caused by 2,4-dinitrochlorobenzene The results were shown in Table 3. As compared to the model control group, the swelling degree of mouse auricle discs significantly decreased in the groups on the medium and high doses of Composition 5, indicating that Composition 5 had a good inhibitory effect on delayed hypersensitivity in mouse auricle skin caused by 2,4-dinitrochlorobenzene.

TABLE 3

Effect of Composition 5 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Model control group | 0.0 | 10 | 6.82 ± 0.86 |
| Positive control group | 5.0 mg | 10 | 4.80 ± 0.73** |
| Test drug low-dose group | 2.0 | 10 | 6.21 ± 0.69 |
| Test drug medium-dose group | 4.0 | 10 | 5.86 ± 0.76* |
| Test drug high-dose group | 12.0 | 10 | 5.21 ± 0.85** |

*$P < 0.05$,
**$P < 0.01$ vs. model control group.

3.3 Effect of Composition 5 on Local Itching in Mice Caused by Low-Molecular-Weight Dextran The test results were shown in Table 4. As compared to the model control group, the OD value significantly decreased in the rat groups on the medium and high doses of Composition 5, indicating that Composition 5 was significantly effective in decreasing the capillary permeability increase in rats caused by histamine phosphate.

TABLE 1

Effect of Composition 5 on the diameter of PCA blue spots in rats ($\bar{x} \pm s$)

| Groups | Dose (g crude drug/kg) | Number of animals | Diameter of blue spots (mm) 1:4 | 1:8 |
|---|---|---|---|---|
| Model control group | 0.0 | 10 | 15.66 ± 2.28 | 9.54 ± 1.52 |
| Positive control group | 5.0 mg | 10 | 11.35 ± 1.74** | 6.72 ± 1.31** |
| Test drug low-dose group | 1.2 | 10 | 13.92 ± 1.95 | 8.53 ± 1.28 |
| Test drug medium-dose group | 2.4 | 10 | 12.77 ± 2.24* | 8.07 ± 1.30* |
| Test drug high-dose group | 7.2 | 10 | 12.10 ± 2.30** | 7.32 ± 1.17 ** |

*$P < 0.05$,
**$P < 0.01$ vs. model control group.

TABLE 2

Effect of Composition 5 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Model control group | 0.0 | 10 | 59.42 ± 12.16 | 3.95 ± 0.87 |
| Positive control group | 5.0 mg | 10 | 21.33 ± 10.48** | 2.12 ± 0.72** |
| Test drug low-dose group | 1.2 | 10 | 48.05 ± 12.54 | 3.21 ± 0.80 |
| Test drug medium-dose group | 2.4 | 10 | 44.29 ± 12.66* | 2.85 ± 0.84* |
| Test drug high-dose group | 7.2 | 10 | 34.80 ± 12.07** | 2.43 ± 0.62** |

*$P < 0.05$,
**$P < 0.01$ vs. model control group.

TABLE 4

Effect of Composition 5 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 28.66 ± 6.70 |
| Positive control group | 5.0 mg | 10 | 17.20 ± 4.08** |
| Test drug low-dose group | 2.0 | 10 | 23.21 ± 5.90 |
| Test drug medium-dose group | 4.0 | 10 | 20.42 ± 6.34* |
| Test drug high-dose group | 12.0 | 10 | 18.55 ± 4.92** |

*$P < 0.05$,
**$P < 0.01$ vs. model control group.

3.4 Effect of Composition 5 on Capillary Permeability in Rats

The test results were shown in Table 5. As compared to the model control group, the OD value significantly decreased in the rat groups on the medium and high doses of Composition 5, indicating that Composition 5 was significantly effective in decreasing the capillary permeability increase in rats caused by histamine phosphate.

TABLE 5

Effect of Composition 5 on capillary permeability in rats ($\bar{x} \pm s$)

| Groups | Dose (g crude drug/kg) | Number of animals | OD value |
|---|---|---|---|
| Model control group | 0.0 | 10 | 1.020 ± 0.130 |
| Positive control group | 5.0 mg | 10 | 0.756 ± 0.102** |
| Test drug low-dose group | 1.2 | 10 | 0.953 ± 0.133 |
| Test drug medium-dose group | 2.4 | 10 | 0.908 ± 0.105* |
| Test drug high-dose group | 7.2 | 10 | 0.842 ± 0.094** |

*$P < 0.05$,
**$P < 0.01$ vs. model control group.

4. Conclusion

The animal experimental studies demonstrate that Composition 5 is significantly effective in inhibiting passive anaphylaxis in rats caused by ovalbumin, that Composition 5 is effective in inhibiting delayed hypersensitivity in mouse auricle skin caused by 2,4-dinitrochlorobenzene, and that Composition 5 is significantly effective in decreasing the capillary permeability increase in rats caused by histamine phosphate. The above results indicate good effectiveness of Composition 5 in resisting allergy and in preventing and treating allergic diseases such as allergic dermatitis and urticaria.

Example 58. Animal Experiment Report of Composition 5 Obtained in Example 5 in Prevention and Treatment of Allergic Rhinitis

1. Materials and Methods
1.1 Sources of Samples

The test drug was Composition 5 (Radix Panacis Quinquefolii, Ganoderma, fermented *Cordyceps sinensis* powder and Cordyceps) provided by Jiangzhong Pharmaceutical Co. Ltd. as composite powder. 1 g dry composite powder was equivalent to 12.39 g total crude drugs.
1.2 Laboratory Animals
The same as in Example 52.
1.3 Primary Reagents
The same as in Example 52.
1.4 Primary Instruments
The same as in Example 52.

2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on the low, medium and high doses of Composition 5, with 10 animals in each group.

2.1.2 Dosage Regime

The daily intake of the test drug Composition 5 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. The blank control group and the allergic rhinitis model group were intragastrically given an equivalent volume of physiological saline; the Bi-yan-kang group was given the drug at a dose of 410 mg/kg. The volume of intragastric administration was calculated as 1.0 ml/100 g body weight. The intragastric administration was initiated after a successful modeling and carried out once per day for 21 consecutive days.

2.1.3 Establishment of Rat Allergic Rhinitis Animal Models
The same as in Example 52.
2.1.4 Assay Indicators
The same as in Example 52.
2.1.4.1 Blood cAMP and cGMP Measurement
The same as in Example 52.
2.1.4.2 Nasal Mucosal Mast Cell Counting
The same as in Example 52.
2.2 Effect on Allergic Rhinitis in Guinea Pigs Caused by TDI
2.2.1. The Same as in 2.1.1.
2.2.2. The Same as in 2.1.2.
2.2.3 Establishment of guinea pig allergic rhinitis animal models
The same as in Example 52.
2.2.4 Assay Indicators
The same as in Example 52.
2.2.4.1 Guinea Pig Behavior Observation
The same as in Example 52.
2.2.4.2 Counts of Eosinophils (EOS) in Nasal Secretion
The same as in Example 52.
2.2.4.3 Total Serum IgE and Blood Histamine Measurement
The same as in Example 52.
2.2.4.4 Nasal Mucosa Thickness Measurement
The same as in Example 52.
2.3 Statistic Method Experimental data were presented in $\bar{X} \pm S$. One-way ANOVA analysis was employed to compare the differences among the blank control group, the model control group and the groups on various doses of Composition 5. $P < 0.05$ was considered as significantly different. $P < 0.01$ was considered as highly significantly different.

3. Results
3.1 Effect of Composition 5 on Allergic Rhinitis in Rats Caused by Ovalbumin
3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased ($P < 0.01$ or $P < 0.05$), and the low-dose group also showed a tendency to decrease.

TABLE 2

Effect of Composition 5 on symptom scores of allergic rhinitis in rats before and after dosing ($\bar{x} \pm s$)

| Groups | Number of animals | Dose (g crude drug/kg) | Before dosing | After dosing Day 7 | After dosing Day 14 | After dosing Day 21 |
|---|---|---|---|---|---|---|
| Blank control group | 10 | — | 0.33 ± 0.29 | 0.44 ± 0.26 | 0.39 ± 0.21 | 0.35 ± 0.19 |
| Model control group | 10 | — | 6.71 ± 1.49** | 6.57 ± 1.24** | 7.10 ± 1.35** | 6.51 ± 1.18** |
| Bi-yan-kang group | 10 | 0.41 | 6.58 ± 1.21** | 3.21 ± 0.97$^{\Delta\Delta}$ | 3.68 ± 1.23$^{\Delta\Delta}$ | 2.95 ± 1.02$^{\Delta\Delta}$ |
| Test drug low-dose group | 10 | 1.0 | 6.75 ± 1.18** | 5.82 ± 0.87 | 5.89 ± 1.42 | 5.63 ± 1.08 |
| Test drug medium-dose group | 10 | 2.0 | 6.54 ± 1.29** | 5.40 ± 1.24$^{\Delta}$ | 5.31 ± 1.45$^{\Delta}$ | 4.57 ± 1.43$^{\Delta\Delta}$ |
| Test drug high-dose group | 10 | 6.0 | 6.75 ± 1.14** | 4.68 ± 0.84$^{\Delta\Delta}$ | 4.45 ± 1.38$^{\Delta\Delta}$ | 4.26 ± 1.31$^{\Delta\Delta}$ |

Note:
**$P < 0.01$ vs. blank control group;
$^{\Delta}P < 0.05$,
$^{\Delta\Delta}P < 0.01$ vs. model group.

3.1.2 Effect of Composition 5 on Serum cAMP and cGMP Levels in Rats

Experimental results were shown in Table 3. As compared to the blank control group, the model group showed a significantly decreased serum cAMP level ($P<0.01$) and a significantly increased serum cGMP level ($P<0.01$). As compared to the model control group, the Bi-yan-kang group and all test drug groups showed a significantly increased serum cAMP level ($P<0.01$ or $P<0.05$); the Bi-yan-kang group and the test drug medium- and high-dose groups showed a significantly decreased serum cGMP level ($P<0.01$ or $P<0.05$), and the low dose group also showed a tendency to decrease.

3.1.3 Effect of Composition 5 on Mast Cells in Rat Nasal Mucosa

The experimental results were shown in Table 3. The number of nasal mucosa mast cells in the model control group significantly increased with a highly significant difference ($P<0.01$). As compared to the model control group, the number of nasal mucosa mast cells in the Bi-yan-kang group and the test drug treatment groups all significantly decreased with a significant difference ($P<0.01$).

TABLE 3

Effect of Composition 5 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell counts (cells) |
|---|---|---|---|---|---|
| Blank control group | — | 10 | 19.98 ± 4.96 | 9.72 ± 2.64 | 1.69 ± 1.41 |
| Model control group | — | 10 | 10.27 ± 3.85** | 14.83 ± 4.88** | 14.33 ± 4.75** |
| Bi-yan-kang group | 0.41 | 10 | 18.25 ± 3.62$^{\Delta\Delta}$ | 9.03 ± 2.52$^{\Delta\Delta}$ | 5.87 ± 2.23$^{\Delta\Delta}$ |
| Test drug low-dose group | 1.0 | 10 | 14.13 ± 3.91$^{\Delta}$ | 12.40 ± 4.01 | 8.64 ± 3.51$^{\Delta\Delta}$ |
| Test drug medium-dose group | 2.0 | 10 | 15.86 ± 5.23$^{\Delta}$ | 10.58 ± 2.84$^{\Delta}$ | 7.79 ± 3.18$^{\Delta\Delta}$ |
| Test drug high-dose group | 6.0 | 10 | 17.74 ± 4.12$^{\Delta\Delta}$ | 9.25 ± 4.05$^{\Delta\Delta}$ | 6.56 ± 2.17$^{\Delta\Delta}$ |

Note:
*$P < 0.05$,
**$P < 0.01$ vs. blank group;
$^{\Delta}P < 0.05$,
$^{\Delta\Delta}P < 0.01$ vs. model group.

3.2 Effect of Composition 5 on Allergic Rhinitis in Guinea Pigs Caused by TDI

3.2.1 Effect on Guinea Pig Behaviors

Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 5 on symptom scores of allergic rhinitis in guinea pigs before and after dosing ($\bar{x} \pm s$)

| Groups | Number of animals | Dose (g crude drug/kg) | Before dosing | After dosing Day 7 | After dosing Day 14 | After dosing Day 21 |
|---|---|---|---|---|---|---|
| Blank control group | 10 | — | 0.57 ± 0.73 | 0.48 ± 0.35 | 0.36 ± 0.30 | 0.41 ± 0.66 |
| Model control group | 10 | — | 6.27 ± 1.24** | 6.51 ± 1.18** | 6.51 ± 1.04** | 5.91 ± 0.92** |
| Bi-yan-kang group | 10 | 0.41 | 6.65 ± 1.13** | 5.31 ± 0.87$^\Delta$ | 5.364 ± 0.91$^\Delta$ | 4.79 ± 1.31$^\Delta$ |
| Test drug low-dose group | 10 | 1.0 | 6.56 ± 1.28** | 5.37 ± 1.35 | 5.72 ± 0.99 | 5.08 ± 1.35 |
| Test drug medium-dose group | 10 | 2.0 | 6.44 ± 1.05** | 5.35 ± 1.26$^\Delta$ | 4.75 ± 1.30$^{\Delta\Delta}$ | 4.54 ± 0.79$^{\Delta\Delta}$ |
| Test drug high-dose group | 10 | 6.0 | 6.71 ± 1.15** | 4.57 ± 1.08$^{\Delta\Delta}$ | 3.94 ± 0.87$^{\Delta\Delta}$ | 3.66 ± 0.95$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 5 was effective in treating allergic rhinitis by inhibiting the blood histamine level and serum IgE.

(P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness sig-

TABLE 5

Effect of Composition 5 on blood histamine and total serum IgE in guinea pigs ($\bar{x} \pm s$)

| Groups | Number of animals | Dose (g crude drug/kg) | Histamine fluorescence (mg · L) | IgE (IU · mL$^{-1}$) |
|---|---|---|---|---|
| Blank control group | 10 | — | 2.13 ± 0.34 | 0.125 ± 0.021 |
| Model control group | 10 | — | 3.17 ± 0.88** | 0.160 ± 0.033** |
| Bi-yan-kang group | 10 | 0.41 | 2.15 ± 0.46$^{\Delta\Delta}$ | 0.121 ± 0.025$^{\Delta\Delta}$ |
| Test drug low-dose group | 10 | 1.0 | 2.94 ± 0.46 | 0.135 ± 0.029 |
| Test drug medium-dose group | 10 | 2.0 | 2.33 ± 0.41$^\Delta$ | 0.124 ± 0.026$^\Delta$ |
| Test drug high-dose group | 10 | 6.0 | 2.15 ± 0.37$^{\Delta\Delta}$ | 0.118 ± 0.009$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.3 Effect on Eosinophils (EOS) in Nasal Secretion of Guinea Pigs

Experimental results were shown in Table 6. The number of eosinophils in the model group significantly increased nificantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 5 on EOS in nasal secretion and nasal mucosa thickness in guinea pigs ($\bar{x} \pm s$)

| Groups | Dose (g crude drug/kg) | Number of animals | Number of EOS ($\times 10^{-9}$/L) | Mucosa thickness (mm) |
| --- | --- | --- | --- | --- |
| Blank control group | — | 10 | 2.68 ± 1.36 | 0.157 ± 0.050 |
| Model control group | — | 10 | 18.64 ± 4.14** | 0.283 ± 0.071** |
| Bi-yan-kang group | 0.41 | 10 | 9.27 ± 3.75$^{\Delta\Delta}$ | 0.199 ± 0.047$^{\Delta\Delta}$ |
| Test drug low-dose group | 1.0 | 10 | 11.27 ± 4.13$^{\Delta\Delta}$ | 0.214 ± 0.049$^{\Delta\Delta}$ |
| Test drug medium-dose group | 2.0 | 10 | 9.44 ± 3.55$^{\Delta\Delta}$ | 0.191 ± 0.067$^{\Delta\Delta}$ |
| Test drug high-dose group | 6.0 | 10 | 7.12 ± 2.76$^{\Delta\Delta}$ | 0.186 ± 0.059$^{\Delta\Delta}$ |

Note:
*$P < 0.05$,
**$P < 0.01$ vs. blank group;
$^{\Delta}P < 0.05$,
$^{\Delta\Delta}P < 0.01$ vs. model group.

4. Conclusion

The animal experimental studies demonstrate that the effectiveness of Composition 5 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 5 is effective in resisting allergic rhinitis.

Example 59. Animal Experiment Report of Composition 5 Obtained in Example 5 in Prevention and Treatment of Allergic Asthma 1. Materials and Methods
1.1 Sources of Samples The test drug was Composition 5 (Radix Panacis Quinquefolii, Ganoderma, fermented *Cordyceps sinensis* powder and Cordyceps) provided by Jiangzhong Pharmaceutical Co. Ltd. as composite powder. 1 g dry composite powder was equivalent to 12.39 g total crude drugs.
1.2 Laboratory Animals
The same as in Example 53.
1.3 Primary Reagents
The same as in Example 53.
1.4 Primary Instruments
The same as in Example 53.
2. Experimental Methods
2.1 Effect on Allergic Asthma in Rats Caused by OVA
2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on the low, medium and high doses of Composition 5, with 10 animals in each group.

2.1.2 Establishment of Rat Allergic Asthma Animal Models
The same as in Example 53.
2.1.3 Dosage Regime The daily intake of the test drug Composition 5 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.07 mg dry powder/ml, 16.14 mg dry powder/ml, 48.43 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 5 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.
2.1.4 Recording of Latent Period of Asthma in Rats
The same as in Example 53.
2.1.5 Measurements of IL-4 and IFN-γ Levels
The same as in Example 53.
2.1.6 Measurement of EOS Content in Lung Tissues
The same as in Example 53.
2.2 Effect on Allergic Asthma in Guinea Pigs Caused by a Mixed Gas of Ach and his
2.2.1. The Same as in 2.1.1.
2.2.2 Establishment of Guinea Pig Allergic Asthma Animal Models
The same as in Example 53.
2.2.3 Dosage Regime
The same as in 2.1.3.
2.2.4 Recording of Latent Period of Asthma
The same as in 2.1.4.1.
2.2.5 Measurement of IgE in Serum and BALF
Dual-antibody sandwich radioimmunoassay was employed.
2.3 Statistic Method
The same as in Example 53.

3. Results
3.1 Effect of Composition 5 on Allergic Asthma in Rats Caused by OVA
3.1.1 Effect on the Latent Period of Asthma Induced in Rats Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged ($P<0.05$ or $P<0.01$).

TABLE 1

Effect of Composition 5 on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 77.31 ± 13.84** | 75.61 ± 12.89** |
| Positive control group | 10 | 0.5 mg/kg | 74.64 ± 11.03** | 160.21 ± 20.32$^{\Delta\Delta}$ |
| Test drug low-dose group | 10 | 1.0 | 75.62 ± 15.28** | 85.04 ± 21.35 |
| Test drug medium-dose group | 10 | 2.0 | 78.49 ± 14.08** | 96.48 ± 23.61$^{\Delta}$ |
| Test drug high-dose group | 10 | 6.0 | 77.84 ± 17.43** | 102.68 ± 23.85$^{\Delta\Delta}$ |

Note:
**$P < 0.01$ vs. blank group;
$^{\Delta}P < 0.05$,
$^{\Delta\Delta}P < 0.01$ vs. model group.

3.1.2 Effect on Serum IL-4 and IFN-γ Levels in Rats

Experimental results were shown in Table 2. As compared to the blank control group, the model group showed a significantly decreased serum IFN-γ level ($P<0.01$) but a significantly increased serum IL-4 level ($P<0.01$), indicating a severe imbalance of the IFN-γ/IL-4 ratio during asthma onsets. As compared to the model group, the dexamethasone group and the test drug medium- and high-dose groups all showed a significantly decreased IL-4 level ($P<0.05$ or $P<0.01$) and a significantly increased IFN-γ level ($P<0.05$ or $P<0.01$), indicating that the test drug can redress the imbalanced IFN-γ/IL-4 ratio.

TABLE 2

Effect of Composition 5 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.70 ± 2.55 | 24.29 ± 4.18 |
| Model control group | — | 10 | 22.46 ± 3.57** | 11.81 ± 3.42** |
| Positive control group | 0.5 mg/kg | 10 | 13.50 ± 4.28$^{\Delta\Delta}$ | 20.27 ± 4.88$^{\Delta\Delta}$ |
| Test drug low-dose group | 1.0 | 10 | 20.59 ± 3.15 | 13.79 ± 3.71 |
| Test drug medium-dose group | 2.0 | 10 | 18.26 ± 4.13$^{\Delta}$ | 15.58 ± 3.80$^{\Delta}$ |
| Test drug high-dose group | 6.0 | 10 | 16.14 ± 3.32$^{\Delta\Delta}$ | 17.32 ± 4.98$^{\Delta\Delta}$ |

Note:
**$P < 0.01$ vs. blank group;
$^{\Delta}P < 0.05$,
$^{\Delta\Delta}P < 0.01$ vs. model group.

3.1.3 Effect on the EOS Content in Rat Lung Tissues

Experimental results were shown in Table 3. The number of EOS in rats in the model group significantly increased ($P<0.01$). As compared to the model group, the positive control group and the test drug medium- and high-dose groups showed a significantly decreased number of EOS ($P<0.01$), indicating that Composition 5 is effective in treating allergic asthma possibly by reducing the EOS content in rat lung tissues.

TABLE 3

Effect of Composition 5 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | 2.26 ± 0.87 |
| Model control group | — | 10 | 105.60 ± 13.96** |
| Positive control group | 0.5 mg/kg | 10 | 28.42 ± 4.24$^{\Delta\Delta}$ |
| Test drug low-dose group | 1.0 | 10 | 95.23 ± 11.32 |
| Test drug medium-dose group | 2.0 | 10 | 71.43 ± 10.44$^{\Delta\Delta}$ |
| Test drug high-dose group | 6.0 | 10 | 65.32 ± 8.59$^{\Delta\Delta}$ |

Note:
**$P < 0.01$ vs. blank group;
$^{\Delta\Delta}P < 0.01$ vs. model group.

3.2 Effect of Composition 5 on Allergic Asthma in Guinea Pigs Caused by a Mixed Gas of Ach and his
3.2.1 Effect on the Latent Period of Asthma Induced in Guinea Pigs Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged (P<0.05 or P<0.01), which indicates that Composition 5 greatly improves the asthmatic symptoms in guinea pigs.

TABLE 4

Effect of Composition 5 on the latent period of asthma induced in guinea pigs
($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 77.18 ± 10.82** | 78.03 ± 10.94** |
| Positive control group | 10 | 0.5 mg/kg | 75.65 ± 9.10** | 155.78 ± 16.24$^{\Delta\Delta}$ |
| Test drug low-dose group | 10 | 1.0 | 76.51 ± 14.32** | 83.01 ± 21.35 |
| Test drug medium-dose group | 10 | 2.0 | 77.83 ± 15.08** | 97.49 ± 24.75$^{\Delta}$ |
| Test drug high-dose group | 10 | 6.0 | 79.64 ± 19.14** | 110.64 ± 24.91$^{\Delta\Delta}$ |

Note:
**P < 0.01 vs. blank group;
$^{\Delta}$P < 0.05,
$^{\Delta\Delta}$P < 0.01 vs. model group.

3.2.2 Effect on the Total IgE in Serum and BALF of Guinea Pigs

Experimental results were shown in Table 5. The total IgE content in serum and BALF in the model group significantly increased (P<0.01). As compared to the model group, the total IgE contents in serum and BALF in the dexamethasone group and in the groups on the medium and high doses of the test drug all significantly decreased (P<0.01 or P<0.05), indicating that both dexamethasone and the test drug can inhibit allergic inflammatory response in guinea pigs' lung and improve asthmatic symptoms.

TABLE 5

Effect of Composition 5 on the total IgE in serum and BALF of guinea pigs
($\bar{x} \pm s$)

| Groups | Dose (g crude drug/kg) | Number of animals | Serum (U/L) | BALF (U/L) |
|---|---|---|---|---|
| Blank control group | — | 10 | 2.01 ± 0.85 | 3.60 ± 0.81 |
| Model control group | — | 10 | 5.63 ± 1.36** | 5.30 ± 1.25** |
| Positive control group | 0.5 mg/kg | 10 | 3.74 ± 1.32$^{\Delta\Delta}$ | 3.70 ± 0.73$^{\Delta\Delta}$ |
| Test drug low-dose group | 1.0 | 10 | 5.13 ± 2.17 | 4.18 ± 1.59 |
| Test drug medium-dose group | 2.0 | 10 | 4.27 ± 1.11$^{\Delta}$ | 3.90 ± 1.46$^{\Delta}$ |
| Test drug high-dose group | 6.0 | 10 | 3.98 ± 1.13$^{\Delta\Delta}$ | 3.88 ± 0.94$^{\Delta\Delta}$ |

Note:
**P < 0.01 vs. blank group;
$^{\Delta}$P < 0.05,
$^{\Delta\Delta}$P < 0.01 vs. model group.

3.2.3 Effect on the EOS Content in Guinea Pigs' Lung Tissues

Experimental results were shown in Table 6. As compared to the blank control group, the level of EOS counts in guinea pigs in the model group significantly increased (P<0.01). As compared to the model group, the level of EOS counts in the positive control group and the test drug medium- and high-dose groups significantly decreased (P<0.01), indicating that Composition 5 is effective in treating allergic asthma possibly by decreasing the EOS content in guinea pigs' lung tissues.

TABLE 6

Effect of Composition 5 on the EOS content in guinea pigs' lung tissues
($\bar{x} \pm s$)

| Groups | Dose (g crude drug/kg) | Number of animals | EOS (cells/HP) |
|---|---|---|---|
| Blank control group | — | 10 | 5.23 ± 2.75 |
| Model control group | — | 10 | 93.63 ± 14.91** |
| Positive control group | 0.5 mg/kg | 10 | 30.77 ± 7.21$^{\Delta\Delta}$ |
| Test drug low-dose group | 1.0 | 10 | 85.27 ± 12.09 |
| Test drug medium-dose group | 2.0 | 10 | 70.27 ± 12.14$^{\Delta\Delta}$ |
| Test drug high-dose group | 6.0 | 10 | 59.24 ± 11.68$^{\Delta\Delta}$ |

Note:
**P < 0.01 vs. blank group;
$^{\Delta\Delta}$P < 0.01 vs. model group.

4. Conclusion

The animal experimental studies demonstrate that Composition 5 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 5 is considered effective in resisting allergic asthma.

Example 60. Animal Experiment Report of Composition 6 Obtained in Example 6 Against Allergy and Allergic Dermatitis 1. Materials and Methods 1.1 Sources of Samples The test drug was Composition 6 (Radix Panacis Quinquefolii, Ganoderma, fermented *Cordyceps sinensis* powder and Flos Rosae Rugosae) provided by Jiangzhong Pharmaceutical Co. Ltd. as composite powder. 1 g dry composite powder was equivalent to 12.56 g total crude drugs. Its daily intake recommended for one person was 24 g crude drug/60 kg body weight.

1.2 Laboratory Animals

The same as in Example 51.

1.3 Primary Reagents

The same as in Example 51.

1.4 Primary Instruments

The same as in Example 51.

2. Experimental Methods 2.1 Animal Grouping

Animals were randomly divided into groups with 10 animals per group based on the body weights. A model control group, groups on the low, medium and high doses of Composition 6, and a positive drug control group (prednisone) were established.

2.2 Dosage Regime

The daily intake of test drug Composition 6 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (15.925 mg dry powder/ml, 31.85 mg dry powder/ml, and 95.55 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (7.96 mg dry powder/ml, 15.92 mg dry powder/ml, and 47.76 mg dry powder/ml) with distilled water to carry out experiments.

2.3 Effect of Composition 6 on Passive Anaphylaxis (PCA) in Rats Caused by Ovalbumin 2.3.1 Preparation of Antiserum The same as in Example 51.

2.3.2 Establishment of Rat Anti-Ovalbumin Serum Models

Anti-ovalbumin serum was taken and diluted at 1:4 or 1:8 with physiological saline. 50 rats were randomly divided into 5 groups, i.e., a model control group, groups on the low, medium and high doses of Composition 6, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 6 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].

2.3.3 Effect of Composition 6 on Delayed Hypersensitivity in Mouse Auricle Skin Caused by 2,4-Dinitrochlorobenzene 50 mice were randomly divided into 5 groups, i.e., a model control group, groups on the low, medium and high doses of Composition 6, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 6 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 6 on Local Itching in Mice Caused by Low-Molecular-Weight Dextran The mice were randomly divided into 5 groups, i.e., a model control group, groups on the low, medium and high doses of Composition 6, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 6 on Capillary Permeability in Rats

The rats were randomly divided into 5 groups, i.e., a model control group, groups on the low, medium and high doses of Composition 6, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 6 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

Experimental data were presented in $\bar{X} \pm S$. One-way ANOVA analysis was employed to compare the differences among the model control group and the groups on various doses of Composition 6. $P<0.05$ was considered as significantly different. $P<0.01$ was considered as highly significantly different.

3. Results

3.1 Effect of Composition 6 on Passive Anaphylaxis in Rats

Test results were shown in Tables 1 and 2. As compared to the model control group, the low dose group on Composition 6 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 6 all showed an effect of significantly decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 6 had a significant inhibitory effect on passive anaphylaxis in rats.

TABLE 1

Effect of Composition 6 on the diameter of PCA blue spots in rats ($\bar{x} \pm s$)

| Groups | Dose (g crude drug/kg) | Number of animals | Diameter of blue spots (mm) 1:4 | 1:8 |
|---|---|---|---|---|
| Model control group | 0.0 | 10 | 17.34 ± 2.35 | 11.32 ± 1.64 |
| Positive control group | 5.0 mg | 10 | 13.22 ± 1.90** | 8.65 ± 1.52** |
| Test drug low-dose group | 1.2 | 10 | 15.78 ± 2.02 | 10.56 ± 1.43 |
| Test drug medium-dose group | 2.4 | 10 | 14.61 ± 2.32* | 9.72 ± 1.52* |
| Test drug high-dose group | 7.2 | 10 | 14.16 ± 2.08** | 9.10 ± 1.29** |

*$P < 0.05$,
**$P < 0.01$ vs. model control group.

TABLE 2

Effect of Composition 6 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Model control group | 0.0 | 10 | 58.42 ± 12.33 | 3.86 ± 0.82 |
| Positive control group | 5.0 mg | 10 | 19.80 ± 10.57** | 2.07 ± 0.76** |
| Test drug low-dose group | 1.2 | 10 | 47.16 ± 12.72 | 3.10 ± 0.84 |
| Test drug medium-dose group | 2.4 | 10 | 43.26 ± 11.42* | 2.84 ± 0.80* |
| Test drug high-dose group | 7.2 | 10 | 33.60 ± 10.67** | 2.21 ± 0.67** |

*$P < 0.05$,
**$P < 0.01$ vs. model control group.

3.2 Effect of Composition 6 on Delayed Hypersensitivity in Mouse Auricle Skin Caused by 2,4-Dinitrochlorobenzene The results were shown in Table 3. As compared to the model control group, the swelling degree of mouse auricle discs significantly decreased in the groups on the medium and high doses of Composition 6, indicating that Composition 6 had a good inhibitory effect on delayed hypersensitivity in mouse auricle skin caused by 2,4-dinitrochlorobenzene.

TABLE 3

Effect of Composition 6 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Model control group | 0.0 | 10 | 6.67 ± 0.69 |
| Positive control group | 5.0 mg | 10 | 4.62 ± 0.79** |
| Test drug low-dose group | 2.0 | 10 | 6.05 ± 0.82 |

TABLE 3-continued

Effect of Composition 6 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Test drug medium-dose group | 4.0 | 10 | 5.72 ± 0.84* |
| Test drug high-dose group | 12.0 | 10 | 5.07 ± 0.80** |

*$P < 0.05$,
**$P < 0.01$ vs. model control group.

3.3 Effect of Composition 6 on Local Itching in Mice Caused by Low-Molecular-Weight Dextran The test results were shown in Table 4. As compared to the model control group, the OD value significantly decreased in the rat groups on the medium and high doses of Composition 6, indicating that Composition 6 was significantly effective in decreasing the capillary permeability increase in rats caused by histamine phosphate.

TABLE 4

Effect of Composition 6 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 27.38 ± 6.82 |
| Positive control group | 5.0 mg | 10 | 15.43 ± 4.56** |
| Test drug low-dose group | 2.0 | 10 | 22.39 ± 5.73 |
| Test drug medium-dose group | 4.0 | 10 | 19.54 ± 6.02* |
| Test drug high-dose group | 12.0 | 10 | 17.27 ± 4.22** |

*$P < 0.05$,
**$P < 0.01$ vs. model control group.

3.4 Effect of Composition 6 on Capillary Permeability in Rats

The test results were shown in Table 5. As compared to the model control group, the OD value significantly decreased in the rat groups on the medium and high doses of Composition 6, indicating that Composition 6 was significantly effective in decreasing the capillary permeability increase in rats caused by histamine phosphate.

TABLE 5

Effect of Composition 6 on capillary permeability in rats ($\bar{x} \pm s$)

| Groups | Dose (g crude drug/kg) | Number of animals | OD value |
|---|---|---|---|
| Model control group | 0.0 | 10 | 1.037 ± 0.108 |
| Positive control group | 5.0 mg | 10 | 0.773 ± 0.109** |
| Test drug low-dose group | 1.2 | 10 | 0.969 ± 0.136 |
| Test drug medium-dose group | 2.4 | 10 | 0.924 ± 0.121* |
| Test drug high-dose group | 7.2 | 10 | 0.860 ± 0.090** |

*$P < 0.05$,
**$P < 0.01$ vs. model control group.

4. Conclusion

The animal experimental studies demonstrate that Composition 6 is significantly effective in inhibiting passive anaphylaxis in rats caused by ovalbumin, that Composition 6 is effective in inhibiting delayed hypersensitivity in mouse auricle skin caused by 2,4-dinitrochlorobenzene, and that Composition 6 is significantly effective in decreasing the capillary permeability increase in rats caused by histamine phosphate. The above results indicate good effectiveness of Composition 6 in resisting allergy and in preventing and treating allergic diseases such as allergic dermatitis and urticaria.

Example 61. Animal Experiment Report of Composition 6 Obtained in Example 6 in Prevention and Treatment of Allergic Rhinitis 1. Materials and Methods
1.1 Sources of Samples The test drug was Composition 6 (Radix Panacis Quinquefolii, Ganoderma, fermented *Cordyceps sinensis* powder and Flos Rosae Rugosae) provided by Jiangzhong Pharmaceutical Co. Ltd. as composite powder. 1 g dry composite powder was equivalent to 12.56 g total crude drugs.
1.2 Laboratory Animals
The same as in Example 52.
1.3 Primary Reagents
The same as in Example 52.
1.4 Primary Instruments
The same as in Example 52.
2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on the low, medium and high doses of Composition 6, with 10 animals in each group.
2.1.2 Dosage Regime The daily intake of the test drug Composition 6 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. The blank control group and the allergic rhinitis model group were intragastrically given an equivalent volume of physiological saline; the Bi-yan-kang group was given the drug at a dose of 410 mg/kg. The volume of intragastric administration was calculated as 1.0 ml/100 g body weight. The intragastric administration was initiated after a successful modeling and carried out once per day for 21 consecutive days.
2.1.3 Establishment of Rat Allergic Rhinitis Animal Models
The same as in Example 52.
2.1.4 Assay Indicators
The same as in Example 52.
2.1.4.1 Blood cAMP and cGMP Measurement
The same as in Example 52.
2.1.4.2 Nasal Mucosal Mast Cell Counting
The same as in Example 52.
2.2 Effect on Allergic Rhinitis in Guinea Pigs Caused by TDI
2.2.1. The Same as in 2.1.1.
2.2.2. The Same as in 2.1.2.
2.2.3 Establishment of Guinea Pig Allergic Rhinitis Animal Models
The same as in Example 52.
2.2.4 Assay Indicators
The same as in Example 52.
2.2.4.1 Guinea Pig Behavior Observation
The same as in Example 52.

2.2.4.2 Counts of Eosinophils (EOS) in Nasal Secretion
The same as in Example 52.
2.2.4.3 Total Serum IgE and Blood Histamine Measurement
The same as in Example 52.
2.2.4.4 Nasal Mucosa Thickness Measurement
The same as in Example 52.

2.3 Statistic Method

Experimental data were presented in $\bar{X}\pm S$. One-way ANOVA analysis was employed to compare the differences among the blank control group, the model control group and the groups on various doses of Composition 6. P<0.05 was considered as significantly different. P<0.01 was considered as highly significantly different.

3. Results 3.1 Effect of Composition 6 on Allergic Rhinitis in Rats Caused by Ovalbumin 3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 2

Effect of Composition 6 on symptom scores of allergic rhinitis in rats before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.33 ± 0.29 | 0.44 ± 0.26 | 0.39 ± 0.21 | 0.35 ± 0.19 |
| Model control group | 10 | — | 6.71 ± 1.49** | 6.57 ± 1.24** | 7.10 ± 1.35** | 6.51 ± 1.18** |
| Bi-yan-kang group | 10 | 0.41 | 6.58 ± 1.21** | 3.21 ± 0.97$^{\Delta\Delta}$ | 3.68 ± 1.23$^{\Delta\Delta}$ | 2.95 ± 1.02$^{\Delta\Delta}$ |
| Test drug low-dose group | 10 | 1.0 | 6.75 ± 1.18** | 5.82 ± 0.87 | 5.89 ± 1.42 | 5.63 ± 1.08 |
| Test drug medium-dose group | 10 | 2.0 | 6.54 ± 1.29** | 5.40 ± 1.24$^{\Delta}$ | 5.31 ± 1.45$^{\Delta}$ | 4.57 ± 1.43$^{\Delta\Delta}$ |
| Test drug high-dose group | 10 | 6.0 | 6.75 ± 1.14** | 4.68 ± 0.84$^{\Delta\Delta}$ | 4.45 ± 1.38$^{\Delta\Delta}$ | 4.26 ± 1.31$^{\Delta\Delta}$ |

Note:
**P < 0.01 vs. blank control group;
$^{\Delta}$P < 0.05,
$^{\Delta\Delta}$P < 0.01 vs. model group.

3.1.2 Effect of Composition 6 on Serum cAMP and cGMP Levels in Rats

Experimental results were shown in Table 3. As compared to the blank control group, the model group showed a significantly decreased serum cAMP level (P<0.01) and a significantly increased serum cGMP level (P<0.01). As compared to the model control group, the Bi-yan-kang group and all test drug groups showed a significantly increased serum cAMP level (P<0.01 or P<0.05); the Bi-yan-kang group and the test drug medium- and high-dose groups showed a significantly decreased serum cGMP level (P<0.01 or P<0.05), and the low dose group also showed a tendency to decrease.

3.1.3 Effect of Composition 6 on Mast Cells in Rat Nasal Mucosa

The experimental results were shown in Table 3. The number of nasal mucosa mast cells in the model control group significantly increased with a highly significant difference (P<0.01). As compared to the model control group, the number of nasal mucosa mast cells in the Bi-yan-kang group and the test drug treatment groups all significantly decreased with a significant difference (P<0.01).

TABLE 3

Effect of Composition 6 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell counts (cells) |
|---|---|---|---|---|---|
| Blank control group | — | 10 | 19.98 ± 4.96 | 9.72 ± 2.64 | 1.69 ± 1.41 |
| Model control group | — | 10 | 10.27 ± 3.85** | 14.83 ± 4.88** | 14.33 ± 4.75** |
| Bi-yan-kang group | 0.41 | 10 | 18.25 ± 3.62$^{\Delta\Delta}$ | 9.03 ± 2.52$^{\Delta\Delta}$ | 5.87 ± 2.23$^{\Delta\Delta}$ |
| Test drug low-dose group | 1.0 | 10 | 14.13 ± 3.91$^{\Delta}$ | 12.40 ± 4.01 | 8.64 ± 3.51$^{\Delta\Delta}$ |

TABLE 3-continued

Effect of Composition 6 on serum cAMP and cGMP levels and nasal mucosa mast cells in rats ($\bar{x} \pm s$)

| Groups | Dose (g crude drug/kg) | Number of animals | cGMP (pmol/ml) | cGMP (pmol/ml) | Mast cell counts (cells) |
|---|---|---|---|---|---|
| Test drug medium-dose group | 2.0 | 10 | 15.86 ± 5.23$^\Delta$ | 10.58 ± 2.84$^\Delta$ | 7.79 ± 3.18$^{\Delta\Delta}$ |
| Test drug high-dose group | 6.0 | 10 | 17.74 ± 4.12$^{\Delta\Delta}$ | 9.25 ± 4.05$^{\Delta\Delta}$ | 6.56 ± 2.17$^{\Delta\Delta}$ |

Note:
*$P < 0.05$,
**$P < 0.01$ vs. blank group;
$^\Delta P < 0.05$,
$^{\Delta\Delta}P < 0.01$ vs. model group.

3.2 Effect of Composition 6 on Allergic Rhinitis in Guinea Pigs Caused by TDI 3.2.1 Effect on Guinea Pig Behaviors Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 6 on symptom scores of allergic rhinitis in guinea pigs before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.54 ± 0.70 | 0.48 ± 0.33 | 0.35 ± 0.27 | 0.41 ± 0.63 |
| Model control group | 10 | — | 6.27 ± 1.21** | 6.3 ± 1.19** | 6.53 ± 1.01** | 6.01 ± 0.97** |
| Bi-yan-kang group | 10 | 0.41 | 6.64 ± 1.08** | 5.28 ± 0.86$^\Delta$ | 5.35 ± 0.94$^\Delta$ | 4.79 ± 1.25$^\Delta$ |
| Test drug low-dose group | 10 | 1.0 | 6.56 ± 1.31** | 5.31 ± 1.37 | 5.68 ± 0.93 | 5.04 ± 1.35 |
| Test drug medium-dose group | 10 | 2.0 | 6.43 ± 1.09** | 5.02 ± 1.29$^\Delta$ | 4.74 ± 1.31$^{\Delta\Delta}$ | 4.51 ± 0.79$^{\Delta\Delta}$ |
| Test drug high-dose group | 10 | 6.0 | 6.66 ± 1.12** | 4.53 ± 1.08$^{\Delta\Delta}$ | 3.93 ± 0.82$^{\Delta\Delta}$ | 3.63 ± 0.92$^{\Delta\Delta}$ |

Note:
*$P < 0.05$,
**$P < 0.01$ vs. blank group;
$^\Delta P < 0.05$,
$^{\Delta\Delta}P < 0.01$ vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 6 was effective in treating allergic rhinitis by inhibiting the blood histamine level and serum IgE.

TABLE 5

Effect of Composition 6 on blood histamine and total serum IgE in guinea pigs ($\bar{x} \pm s$)

| Groups | Number of animals | Dose (g crude drug/kg) | Histamine fluorescence (mg · L) | IgE (IU · ml$^{-1}$) |
|---|---|---|---|---|
| Blank control group | 10 | — | 2.08 ± 0.41 | 0.124 ± 0.023 |
| Model control group | 10 | — | 3.14 ± 0.91** | 0.163 ± 0.037** |
| Bi-yan-kang group | 10 | 0.41 | 2.14 ± 0.48$^{\Delta\Delta}$ | 0.121 ± 0.020$^{\Delta\Delta}$ |
| Test drug low-dose group | 10 | 1.0 | 3.01 ± 0.46 | 0.137 ± 0.026 |

TABLE 5-continued

Effect of Composition 6 on blood histamine and total serum IgE in guinea pigs ($\bar{x} \pm s$)

| Groups | Number of animals | Dose (g crude drug/kg) | Histamine fluorescence (mg · L) | IgE (IU · ml$^{-1}$) |
|---|---|---|---|---|
| Test drug medium-dose group | 10 | 2.0 | 2.31 ± 0.45$^\Delta$ | 0.127 ± 0.024$^\Delta$ |
| Test drug high-dose group | 10 | 6.0 | 2.10 ± 0.39$^{\Delta\Delta}$ | 0.121 ± 0.019$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.3 Effect on Eosinophils (EOS) in Nasal Secretion of Guinea Pigs

Experimental results were shown in Table 6. The number of eosinophils in the model group significantly increased (P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness significantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 6 on EOS in nasal secretion and nasal mucosa thickness in guinea pigs ($\bar{x} \pm s$)

| Groups | Dose (g crude drug/kg) | Number of animals | Number of EOS (×10$^{-9}$/L) | Mucosa thickness (mm) |
|---|---|---|---|---|
| Blank control group | — | 10 | 2.68 ± 1.39 | 0.159 ± 0.050 |
| Model control group | — | 10 | 18.66 ± 4.17** | 0.286 ± 0.071** |
| Bi-yan-kang group | 0.41 | 10 | 10.30 ± 3.81$^{\Delta\Delta}$ | 0.199 ± 0.048$^{\Delta\Delta}$ |
| Test drug low-dose group | 1.0 | 10 | 13.29 ± 4.12$^{\Delta\Delta}$ | 0.216 ± 0.047$^{\Delta\Delta}$ |
| Test drug medium-dose group | 2.0 | 10 | 12.41 ± 3.54$^{\Delta\Delta}$ | 0.195 ± 0.068$^{\Delta\Delta}$ |
| Test drug high-dose group | 6.0 | 10 | 11.13 ± 2.87$^{\Delta\Delta}$ | 0.196 ± 0.063$^{\Delta\Delta}$ |

Note:
*P < 0.05,
**P < 0.01 vs. blank group;
$^\Delta$P < 0.05,
$^{\Delta\Delta}$P < 0.01 vs. model group.

4. Conclusion

The animal experimental studies demonstrate that the effectiveness of Composition 6 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 6 is effective in resisting allergic rhinitis.

Example 62. Animal Experiment Report of Composition 6 Obtained in Example 6 in Prevention and Treatment of Allergic Asthma 1. Materials and Methods 1.1 Sources of Samples The test drug was Composition 6 (Radix Panacis Quinquefolii, Ganoderma, fermented *Cordyceps sinensis* powder and Flos Rosae Rugosae) provided by Jiangzhong Pharmaceutical Co. Ltd. as composite powder. 1 g dry composite powder was equivalent to 12.56 g total crude drugs.

1.2 Laboratory Animals

The same as in Example 53.

1.3 Primary Reagents

The same as in Example 53.

1.4 Primary Instruments

The same as in Example 53.

2. Experimental Methods 2.1 Effect on Allergic Asthma in Rats Caused by OVA 2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on the low, medium and high doses of Composition 6, with 10 animals in each group.

2.1.2 Establishment of Rat Allergic Asthma Animal Models
The same as in Example 53.

2.1.3 Dosage Regime
The daily intake of the test drug Composition 6 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (7.96 mg dry powder/ml, 15.92 mg dry powder/ml, 47.77 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 6 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.

2.1.4 Recording of Latent Period of Asthma in Rats
The same as in Example 53.

2.1.5 Measurements of IL-4 and IFN-γ Levels
The same as in Example 53.

2.1.6 Measurement of EOS Content in the Lung Tissues
The same as in Example 53.

2.2 Effect on Allergic Asthma in Guinea Pigs Caused by a Mixed Gas of Ach and his 2.2.1. The Same as in 2.1.1.

2.2.2 Establishment of Guinea Pig Allergic Asthma Animal Models
The same as in Example 53.

2.2.3 Dosage Regime
The same as in 2.1.3.

2.2.4 Recording of Latent Period of Asthma
The same as in 2.1.4.1.

2.2.5 Measurement of IgE in Serum and BALF
The same as in Example 53.

2.3 Statistic Method
The same as in Example 53.

3 Results 3.1 Effect of Composition 6 on Allergic Asthma in Rats Caused by OVA 3.1.1 Effect on the Latent Period of Asthma Induced in Rats
Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged (P<0.05 or P<0.01).

TABLE 1

Effect of Composition 6 on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 77.23 ± 13.81** | 75.52 ± 12.88** |
| Positive control group | 10 | 0.5 mg/kg | 74.67 ± 11.10** | 159.78 ± 20.27△△ |
| Test drug low-dose group | 10 | 1.0 | 75.62 ± 15.31** | 85.01 ± 21.33 |
| Test drug medium-dose group | 10 | 2.0 | 78.51 ± 14.09** | 96.52 ± 23.67△ |
| Test drug high-dose group | 10 | 6.0 | 78.58 ± 17.14** | 112.30 ± 25.8647△△ |

Note:
**P < 0.01 vs. blank group;
△P < 0.05,
△△P < 0.01 vs. model group.

3.1.2 Effect on Serum IL-4 and IFN-γ Levels in Rats
Experimental results were shown in Table 2. As compared to the blank control group, the model group showed a significantly decreased serum IFN-γ level (P<0.01) but a significantly increased serum IL-4 level (P<0.01), indicating a severe imbalance of the IFN-γ/IL-4 ratio during asthma onsets. As compared to the model group, the dexamethasone group and the test drug medium- and high-dose groups all showed a significantly decreased IL-4 level (P<0.05 or P<0.01) and a significantly increased IFN-γ level (P<0.05 or P<0.01), indicating that the test drug can redress the imbalanced IFN-γ/IL-4 ratio.

TABLE 2

Effect of Composition 6 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.71 ± 2.52 | 24.31 ± 4.19 |
| Model control group | — | 10 | 22.43 ± 3.57** | 11.83 ± 3.48** |

TABLE 2-continued

Effect of Composition 6 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Positive control group | 0.5 mg/kg | 10 | $13.50 \pm 4.32^{\Delta\Delta}$ | $20.27 \pm 4.89^{\Delta\Delta}$ |
| Test drug low-dose group | 1.0 | 10 | $20.56 \pm 3.19$ | $13.79 \pm 3.75$ |
| Test drug medium-dose group | 2.0 | 10 | $18.23 \pm 4.12^{\Delta\Delta}$ | $15.61 \pm 3.81^{\Delta}$ |
| Test drug high-dose group | 6.0 | 10 | $16.11 \pm 3.38^{\Delta\Delta}$ | $17.35 \pm 4.92^{\Delta\Delta}$ |

Note:
\*\*P < 0.01 vs. blank group;
$^{\Delta}$P < 0.05,
$^{\Delta\Delta}$P < 0.01 vs. model group.

3.1.3 Effect on the EOS Content in Rat Lung Tissues

Experimental results were shown in Table 3. The number of EOS in rats in the model group significantly increased (P<0.01). As compared to the model group, the positive control group and the test drug medium- and high-dose groups showed a significantly decreased number of EOS (P<0.01), indicating that Composition 6 is effective in treating allergic asthma possibly by reducing the EOS content in rat lung tissues.

TABLE 3

Effect of Composition 6 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | $2.22 \pm 0.86$ |
| Model control group | — | 10 | $103.61 \pm 13.93^{**}$ |
| Positive control group | 0.5 mg/kg | 10 | $28.40 \pm 4.25^{\Delta\Delta}$ |
| Test drug low-dose group | 1.0 | 10 | $93.22 \pm 11.28$ |
| Test drug medium-dose group | 2.0 | 10 | $78.11 \pm 10.36^{\Delta\Delta}$ |
| Test drug high-dose group | 6.0 | 10 | $65.20 \pm 8.47^{\Delta\Delta}$ |

Note:
\*\*P < 0.01 vs. blank group;
$^{\Delta\Delta}$P < 0.01 vs. model group.

3.2 Effect of Composition 6 on Allergic Asthma in Guinea Pigs Caused by a Mixed Gas of Ach and his 3.2.1 Effect on the Latent Period of Asthma Induced in Guinea Pigs Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged (P<0.05 or P<0.01), which indicates that Composition 6 greatly improves the asthmatic symptoms in guinea pigs.

TABLE 4

Effect of Composition 6 on the latent period of asthma induced in guinea pigs ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | $76.17 \pm 10.81^{}$ | $77.01 \pm 10.95^{}$ |
| Positive control group | 10 | 0.5 mg/kg | $75.62 \pm 9.10^{**}$ | $155.78 \pm 16.29^{\Delta\Delta}$ |
| Test drug low-dose group | 10 | 1.0 | $76.52 \pm 14.31^{**}$ | $83.02 \pm 21.31$ |
| Test drug medium-dose group | 10 | 2.0 | $77.80 \pm 15.09^{**}$ | $97.51 \pm 24.78^{\Delta}$ |
| Test drug high-dose group | 10 | 6.0 | $79.71 \pm 19.12^{**}$ | $110.68 \pm 24.91^{\Delta\Delta}$ |

Note:
\*\*P < 0.01 vs. blank group;
$^{\Delta}$P < 0.05,
$^{\Delta\Delta}$P < 0.01 vs. model group.

3.2.2 Effect on the Total IgE in Serum and BALF of Guinea Pigs

Experimental results were shown in Table 5. The total IgE content in serum and BALF in the model group significantly increased (P<0.01). As compared to the model group, the total IgE contents in serum and BALF in the dexamethasone group and in the groups on the medium and high doses of the test drug all significantly decreased (P<0.01 or P<0.05), indicating that both dexamethasone and the test drug can inhibit allergic inflammatory response in guinea pigs' lung and improve asthmatic symptoms.

TABLE 5

Effect of Composition 6 on the total IgE in serum and BALF of guinea pigs ($\bar{x} \pm s$)

| Groups | Dose (g crude drug/kg) | Number of animals | Serum (U/L) | BALF (U/L) |
|---|---|---|---|---|
| Blank control group | — | 10 | $2.08 \pm 0.81$ | $3.60 \pm 0.85$ |
| Model control group | — | 10 | $5.61 \pm 1.38^{}$ | $5.30 \pm 1.26^{}$ |
| Positive control group | 0.5 mg/kg | 10 | $3.74 \pm 1.30^{\Delta\Delta}$ | $3.71 \pm 0.70^{\Delta\Delta}$ |

TABLE 5-continued

Effect of Composition 6 on the total IgE in serum and BALF of guinea pigs ($\bar{x} \pm s$)

| Groups | Dose (g crude drug/kg) | Number of animals | Serum (U/L) | BALF (U/L) |
|---|---|---|---|---|
| Test drug low-dose group | 1.0 | 10 | 5.10 ± 2.19 | 4.13 ± 1.56 |
| Test drug medium-dose group | 2.0 | 10 | 4.24 ± 1.12$^\Delta$ | 3.91 ± 1.47$^\Delta$ |
| Test drug high-dose group | 6.0 | 10 | 4.03 ± 1.04$^{\Delta\Delta}$ | 3.87 ± 0.91$^{\Delta\Delta}$ |

Note:
\*\*P < 0.01 vs. blank group;
$^\Delta$P < 0.05,
$^{\Delta\Delta}$P < 0.01 vs. model group.

3.2.3 Effect on the EOS Content in Guinea Pigs' Lung Tissues

Experimental results were shown in Table 6. As compared to the blank control group, the level of EOS counts in guinea pigs in the model group significantly increased (P<0.01). As compared to the model group, the level of EOS counts in the positive control group and the test drug medium- and high-dose groups significantly decreased (P<0.01), indicating that Composition 6 is effective in treating allergic asthma possibly by decreasing the EOS content in guinea pigs' lung tissues.

TABLE 6

Effect of Composition 6 on the EOS content in guinea pigs' lung tissues ($\bar{x} \pm s$)

| Groups | Dose (g crude drug/kg) | Number of animals | EOS (cells/HP) |
|---|---|---|---|
| Blank control group | — | 10 | 5.22 ± 2.86 |
| Model control group | — | 10 | 93.61 ± 14.95\*\* |
| Positive control group | 0.5 mg/kg | 10 | 30.80 ± 7.23$^{\Delta\Delta}$ |
| Test drug low-dose group | 1.0 | 10 | 82.29 ± 12.21 |
| Test drug medium-dose group | 2.0 | 10 | 66.26 ± 12.02$^{\Delta\Delta}$ |
| Test drug high-dose group | 6.0 | 10 | 59.2137 ± 10.66$^{\Delta\Delta}$ |

Note:
\*\*P < 0.01 vs. blank group;
$^{\Delta\Delta}$P < 0.01 vs. model group.

4. Conclusion

The animal experimental studies demonstrate that Composition 6 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 6 is considered effective in resisting allergic asthma.

Example 63. Animal Experiment Report of Composition 7 Obtained in Example 7 Against Allergy and Allergic Dermatitis 1. Materials and Methods
1.1 Sources of Samples The test drug was Composition 7 (Radix Panacis Quinquefolii, Ganoderma, Cordyceps and Flos Rosae Rugosae) provided by Jiangzhong Pharmaceutical Co. Ltd. as composite powder. 1 g dry composite powder was equivalent to 12.19 g total crude drugs. Its daily intake recommended for one person was 24 g crude drug/60 kg body weight.
1.2 Laboratory Animals The same as in Example 51.
1.3 Primary Reagents The same as in Example 51.
1.4 Primary Instruments The same as in Example 51.
2. Experimental Methods
2.1 Animal grouping Animals were randomly divided into groups with 10 animals per group based on the body weights. A model control group, groups on the low, medium and high doses of Composition 7, and a positive drug control group (prednisone) were established.
2.2 Dosage Regime The daily intake of test drug Composition 7 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (16.405 mg dry powder/ml, 32.81 mg dry powder/ml, and 98.43 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.205 mg dry powder/ml, 16.41 mg dry powder/ml, and 49.23 mg dry powder/ml) with distilled water to carry out experiments.
2.3 Effect of Composition 7 on Passive Anaphylaxis (PCA) in Rats Caused by Ovalbumin
2.3.1 Preparation of Antiserum The same as in Example 51.
2.3.2 Establishment of the Rat Anti-Ovalbumin Serum Models Anti-ovalbumin serum was taken and diluted at 1:4 or 1:8 with physiological saline. 50 rats were randomly divided into 5 groups, i.e., a model control group, groups on the low, medium and high doses of Composition 7, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 7 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].

2.3.3 Effect of Composition 7 on Delayed Hypersensitivity in Mouse Auricle Skin Caused by 2,4-Dinitrochlorobenzene[4]

50 mice were randomly divided into 5 groups, i.e., a model control group, groups on the low, medium and high doses of Composition 7, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 7 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 7 on Local Itching in Mice Caused by Low-Molecular-Weight Dextran[5]

The mice were randomly divided into 5 groups, i.e., a model control group, groups on the low, medium and high doses of Composition 7, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 7 on Capillary Permeability in Rats[6]

The rats were randomly divided into 5 groups, i.e., a model control group, groups on the low, medium and high doses of Composition 7, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 7 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

Experimental data were presented in $\bar{X} \pm S$. One-way ANOVA analysis was employed to compare the differences among the model control group and the groups on various doses of Composition 7. $P<0.05$ was considered as significantly different. $P<0.01$ was considered as highly significantly different.

3. Results 3.1 Effect of Composition 7 on Passive Anaphylaxis in Rats

Test results were shown in Tables 1 and 2. As compared to the model control group, the low dose group on Composition 7 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 7 all showed an effect of significantly decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 7 had a significant inhibitory effect on passive anaphylaxis in rats.

TABLE 1

Effect of Composition 7 on the diameter of PCA blue spots in rats ($\bar{x} \pm s$)

| Groups | Dose (g crude drug/kg) | Number of animals | Diameter of blue spots (mm) 1:4 | 1:8 |
|---|---|---|---|---|
| Model control group | 0.0 | 10 | 17.50 ± 2.27 | 11.66 ± 1.92 |
| Positive control group | 5.0 mg | 10 | 12.48 ± 2.16** | 8.32 ± 1.63** |
| Test drug low-dose group | 1.2 | 10 | 15.65 ± 2.44 | 10.55 ± 1.78 |
| Test drug medium-dose group | 2.4 | 10 | 14.80 ± 2.02* | 9.70 ± 1.39* |
| Test drug high-dose group | 7.2 | 10 | 13.68 ± 2.50** | 9.02 ± 1.56** |

*P < 0.05,
**P < 0.01 vs. model control group.

TABLE 2

Effect of Composition 7 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Model control group | 0.0 | 10 | 59.60 ± 12.88 | 3.95 ± 0.95 |
| Positive control group | 5.0 mg | 10 | 17.54 ± 11.23** | 2.11 ± 0.70** |

TABLE 2-continued

Effect of Composition 7 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Test drug low-dose group | 1.2 | 10 | 48.20 ± 12.54 | 3.24 ± 0.82 |
| Test drug medium-dose group | 2.4 | 10 | 44.17 ± 11.96* | 2.96 ± 0.77* |
| Test drug high-dose group | 7.2 | 10 | 32.54 ± 10.03** | 2.32 ± 0.69** |

*$P < 0.05$,
**$P < 0.01$ vs. model control group.

3.2 Effect of Composition 7 on Delayed Hypersensitivity in Mouse Auricle Skin Caused by 2,4-Dinitrochlorobenzene The results were shown in Table 3. As compared to the model control group, the swelling degree of mouse auricle discs significantly decreased in the groups on the medium and high doses of Composition 7, indicating that Composition 7 had a good inhibitory effect on delayed hypersensitivity in mouse auricle skin caused by 2,4-dinitrochlorobenzene.

TABLE 3

Effect of Composition 7 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Model control group | 0.0 | 10 | 6.95 ± 0.77 |
| Positive control group | 5.0 mg | 10 | 4.84 ± 0.70** |
| Test drug low-dose group | 2.0 | 10 | 6.23 ± 0.89 |
| Test drug medium-dose group | 4.0 | 10 | 5.90 ± 0.80* |
| Test drug high-dose group | 12.0 | 10 | 5.21 ± 0.85** |

*$P < 0.05$,
**$P < 0.01$ vs. model control group.

3.3 Effect of Composition 7 on Local Itching in Mice Caused by Low-Molecular-Weight Dextran The test results were shown in Table 4. As compared to the model control group, the OD value significantly decreased in the rat groups on the medium and high doses of Composition 7, indicating that Composition 7 was significantly effective in decreasing the capillary permeability increase in rats caused by histamine phosphate.

TABLE 4

Effect of Composition 7 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 28.42 ± 6.08 |
| Positive control group | 5.0 mg | 10 | 15.57 ± 5.33** |
| Test drug low-dose group | 2.0 | 10 | 23.44 ± 6.21 |
| Test drug medium-dose group | 4.0 | 10 | 20.38 ± 6.92* |
| Test drug high-dose group | 12.0 | 10 | 17.62 ± 5.06** |

*$P < 0.05$,
**$P < 0.01$ vs. model control group.

3.4 Effect of Composition 7 on Capillary Permeability in Rats

The test results were shown in Table 5. As compared to the model control group, the OD value significantly decreased in the rat groups on the medium and high doses of Composition 7, indicating that Composition 7 was significantly effective in decreasing the capillary permeability increase in rats caused by histamine phosphate.

TABLE 5

Effect of Composition 7 on capillary permeability in rats ($\bar{x} \pm s$)

| Groups | Dose (g crude drug/kg) | Number of animals | OD value |
|---|---|---|---|
| Model control group | 0.0 | 10 | 0.943 ± 0.086 |
| Positive control group | 5.0 mg | 10 | 0.662 ± 0.090** |
| Test drug low-dose group | 1.2 | 10 | 0.885 ± 0.102 |
| Test drug medium-dose group | 2.4 | 10 | 0.832 ± 0.088* |
| Test drug high-dose group | 7.2 | 10 | 0.724 ± 0.095** |

*$P < 0.05$,
**$P < 0.01$ vs. model control group.

4. Conclusion

The animal experimental studies demonstrate that Composition 7 is significantly effective in inhibiting passive anaphylaxis in rats caused by ovalbumin, that Composition 7 is effective in inhibiting delayed hypersensitivity in mouse auricle skin caused by 2,4-dinitrochlorobenzene, and that Composition 7 is significantly effective in decreasing the capillary permeability increase in rats caused by histamine phosphate. The above results indicate good effectiveness of Composition 7 in resisting allergy and in preventing and treating allergic diseases such as allergic dermatitis and urticaria.

Example 64. Animal Experiment Report of Composition 7 Obtained in Example 7 in Prevention and Treatment of Allergic Rhinitis 1. Materials and Methods
1.1 Sources of Samples The test drug was Composition 7 (Radix Panacis Quinquefolii, Ganoderma, Cordyceps and Flos Rosae Rugosae) provided by Jiangzhong Pharmaceutical Co. Ltd. as composite powder. 1 g dry composite powder was equivalent to 12.19 g total crude drugs.

1.2 Laboratory Animals
The same as in Example 52.
1.3 Primary Reagents
The same as in Example 52.
1.4 Primary Instruments
The same as in Example 52.
2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on low, medium and high doses of Composition 7, with 10 animals in each group.

2.1.2 Dosage Regime

The daily intake of the test drug Composition 7 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. The blank control group and the allergic rhinitis model group were intragastrically given an equivalent volume of physiological saline; the Bi-yan-kang group was given the drug at a dose of 410 mg/kg. The volume of intragastric administration was calculated as 1.0 ml/100 g body weight. The intragastric administration was initiated after a successful modeling and carried out once per day for 21 consecutive days.

2.1.3 Establishment of Rat Allergic Rhinitis Animal Models
The same as in Example 52.
2.1.4 Assay Indicators
The same as in Example 52.
2.1.4.1 Blood cAMP and cGMP Measurement
The same as in Example 52.
2.1.4.2 Nasal Mucosal Mast Cell Counting
The same as in Example 52.
2.2 Effect on Guinea Pig Allergic Rhinitis Caused by TDI
2.2.1. The Same as in 2.1.1.
2.2.2. The Same as in 2.1.2.
2.2.3 Establishment of Guinea Pig Allergic Rhinitis Animal Models
The same as in Example 52.
2.2.4 Assay Indicators
The same as in Example 52.
2.2.4.1 Guinea Pig Behavior Observation
The same as in Example 52.
2.2.4.2 Counts of Eosinophils (EOS) in Nasal Secretion
The same as in Example 52.
2.2.4.3 Total Serum IgE and Blood Histamine Measurement
The same as in Example 52.
2.2.4.4 Nasal Mucosa Thickness Measurement
The same as in Example 52.

2.3 Statistic Method

Experimental data were presented in $\bar{X}\pm S$. One-way ANOVA analysis was employed to compare the differences among the blank control group, the model control group and the groups on various doses of Composition 7. P<0.05 was considered as significantly different. P<0.01 was considered as highly significantly different.

3. Results 3.1 Effect of Composition 7 on Allergic Rhinitis in Rats Caused by Ovalbumin 3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 2

Effect of Composition 7 on symptom scores of allergic rhinitis in rats before and after dosing ($\bar{x} \pm s$)

| Groups | Number of animals | Dose (g crude drug/kg) | Before dosing | After dosing Day 7 | After dosing Day 14 | After dosing Day 21 |
|---|---|---|---|---|---|---|
| Blank control group | 10 | — | 0.34 ± 0.30 | 0.41 ± 0.23 | 0.38 ± 0.21 | 0.32 ± 0.15 |
| Model control group | 10 | — | 6.69 ± 1.51** | 6.61 ± 1.28** | 6.91 ± 1.31** | 6.51 ± 1.18** |
| Bi-yan-kang group | 10 | 0.41 | 6.62 ± 1.23** | 3.22 ± 0.97$^{\Delta\Delta}$ | 3.68 ± 1.22$^{\Delta\Delta}$ | 2.93 ± 1.01$^{\Delta\Delta}$ |
| Test drug low-dose group | 10 | 1.0 | 6.72 ± 1.16** | 5.81 ± 0.86 | 5.75 ± 1.41 | 5.60 ± 1.07 |
| Test drug medium-dose group | 10 | 2.0 | 6.51 ± 1.32** | 5.28 ± 1.21$^{\Delta}$ | 5.31 ± 1.44 | 4.54 ± 1.46$^{\Delta\Delta}$ |
| Test drug high-dose group | 10 | 6.0 | 6.71 ± 1.09** | 4.68 ± 0.81$^{\Delta\Delta}$ | 4.41 ± 1.37$^{\Delta\Delta}$ | 4.22 ± 1.36$^{\Delta\Delta}$ |

Note:
**P < 0.01 vs. blank control group;
$^{\Delta}$P < 0.05,
$^{\Delta\Delta}$P < 0.01 vs. model group.

3.1.2 Effect of Composition 7 on Serum cAMP and cGMP Levels in Rats

Experimental results were shown in Table 3. As compared to the blank control group, the model group showed a significantly decreased serum cAMP level (P<0.01) and a significantly increased serum cGMP level (P<0.01). As compared to the model control group, the Bi-yan-kang group and all test drug groups showed a significantly increased serum cAMP level (P<0.01 or P<0.05); the Bi-yan-kang group and the test drug medium- and high-dose groups showed a significantly decreased serum cGMP level (P<0.01 or P<0.05), and the low dose group also showed a tendency to decrease.

3.1.3 Effect of Composition 7 on Mast Cells in Rat Nasal Mucosa

The experimental results were shown in Table 3. The number of nasal mucosa mast cells in the model control group significantly increased with a highly significant difference (P<0.01). As compared to the model control group, the number of nasal mucosa mast cells in the Bi-yan-kang group and the test drug treatment groups all significantly decreased with a significant difference (P<0.01)

TABLE 3

Effect of Composition 7 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell counts (cells) |
|---|---|---|---|---|---|
| Blank control group | — | 10 | 20.06 ± 4.99 | 9.81 ± 2.67 | 1.70 ± 1.39 |
| Model control group | — | 10 | 10.31 ± 3.89** | 14.84 ± 4.88** | 14.28 ± 4.71** |
| Bi-yan-kang group | 0.41 | 10 | 18.31 ± 3.62$^{\Delta\Delta}$ | 9.01 ± 2.49$^{\Delta\Delta}$ | 5.87 ± 2.21$^{\Delta\Delta}$ |
| Test drug low-dose group | 1.0 | 10 | 14.01 ± 3.99 | 12.43 ± 3.94 | 9.83 ± 3.54$^{\Delta\Delta}$ |
| Test drug medium-dose group | 2.0 | 10 | 15.84 ± 5.22$^{\Delta}$ | 10.61 ± 2.83$^{\Delta}$ | 8.75 ± 3.20$^{\Delta\Delta}$ |
| Test drug high-dose group | 6.0 | 10 | 17.73 ± 4.10$^{\Delta\Delta}$ | 9.21 ± 3.97$^{\Delta\Delta}$ | 6.53 ± 2.08$^{\Delta\Delta}$ |

Note:
*P < 0.05,
**P < 0.01 vs. blank group;
$^{\Delta}$P < 0.05,
$^{\Delta\Delta}$P < 0.01 vs. model group.

3.2 Effect of Composition 7 on Allergic Rhinitis in Guinea Pigs Caused by TDI 3.2.1 Effect on Guinea Pig Behaviors Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 7 on symptom scores of allergic rhinitis in guinea pigs before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.50 ± 0.62 | 0.43 ± 0.31 | 0.38 ± 0.20 | 0.42 ± 0.65 |
| Model control group | 10 | — | 6.29 ± 1.21** | 6.48 ± 1.16** | 6.53 ± 1.01** | 6.02 ± 0.98** |
| Bi-yan-kang group | 10 | 0.41 | 6.62 ± 1.11** | 5.32 ± 0.89$^{\Delta}$ | 5.31 ± 0.93$^{\Delta}$ | 4.78 ± 1.29$^{\Delta}$ |
| Test drug low-dose group | 10 | 1.0 | 6.53 ± 1.30** | 5.31 ± 1.36 | 5.71 ± 0.99 | 5.02 ± 1.31 |
| Test drug medium-dose group | 10 | 2.0 | 6.41 ± 1.09** | 5.02 ± 1.29$^{\Delta}$ | 4.77 ± 1.31$^{\Delta\Delta}$ | 4.51 ± 0.79$^{\Delta\Delta}$ |
| Test drug high-dose group | 10 | 6.0 | 6.71 ± 1.12** | 4.57 ± 1.08$^{\Delta\Delta}$ | 3.92 ± 0.82$^{\Delta\Delta}$ | 3.69 ± 0.91$^{\Delta\Delta}$ |

Note:
*P < 0.05,
**P < 0.01 vs. blank group;
$^{\Delta}$P < 0.05,
$^{\Delta\Delta}$P < 0.01 vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 7 was effective in treating allergic rhinitis by inhibiting the blood histamine level and serum IgE.

TABLE 5

Effect of Composition 7 on blood histamine and total serum IgE in guinea pigs ($\bar{x} \pm s$)

| Groups | Number of animals | Dose (g crude drug/kg) | Histamine fluorescence (mg · L) | IgE (IU · ml$^{-1}$) |
|---|---|---|---|---|
| Blank control group | 10 | — | 2.15 ± 0.41 | 0.122 ± 0.021 |
| Model control group | 10 | — | 3.16 ± 0.91** | 0.161 ± 0.035** |
| Bi-yan-kang group | 10 | 0.41 | 2.14 ± 0.48$^{\Delta\Delta}$ | 0.120 ± 0.025$^{\Delta\Delta}$ |
| Test drug low-dose group | 10 | 1.0 | 3.02 ± 0.47 | 0.137 ± 0.029 |

TABLE 5-continued

Effect of Composition 7 on blood histamine and total serum IgE in guinea pigs ($\bar{x} \pm s$)

| Groups | Number of animals | Dose (g crude drug/kg) | Histamine fluorescence (mg · L) | IgE (IU · ml$^{-1}$) |
|---|---|---|---|---|
| Test drug medium-dose group | 10 | 2.0 | 2.31 ± 0.44$^{\triangle}$ | 0.127 ± 0.026$^{\triangle}$ |
| Test drug high-dose group | 10 | 6.0 | 2.12 ± 0.39$^{\triangle\triangle}$ | 0.120 ± 0.010$^{\triangle\triangle}$ |

Note:
*P < 0.05,
**P < 0.01 vs. blank group;
$^{\triangle}$P < 0.05,
$^{\triangle\triangle}$P < 0.01 vs. model group.

3.2.3 Effect on Eosinophils (EOS) in Nasal Secretion of Guinea Pigs

Experimental results were shown in Table 6. The number of eosinophils in the model group significantly increased (P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness significantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 7 on EOS in nasal secretion and nasal mucosa thickness in guinea pigs ($\bar{x} \pm s$)

| Groups | Dose (g crude drug/kg) | Number of animals | Number of EOS (×10$^{-9}$/L) | Mucosa thickness (mm) |
|---|---|---|---|---|
| Blank control group | — | 10 | 2.60 ± 1.36 | 0.157 ± 0.052 |
| Model control group | — | 10 | 17.52 ± 4.21** | 0.284 ± 0.070** |
| Bi-yan-kang group | 0.41 | 10 | 12.28 ± 3.81$^{\triangle\triangle}$ | 0.197 ± 0.045$^{\triangle\triangle}$ |
| Test drug low-dose group | 1.0 | 10 | 12.29 ± 4.13$^{\triangle\triangle}$ | 0.204 ± 0.049$^{\triangle\triangle}$ |
| Test drug medium-dose group | 2.0 | 10 | 11.41 ± 3.57$^{\triangle\triangle}$ | 0.184 ± 0.066$^{\triangle\triangle}$ |
| Test drug high-dose group | 6.0 | 10 | 10.13 ± 2.86$^{\triangle\triangle}$ | 0.166 ± 0.068$^{\triangle\triangle}$ |

Note:
*P < 0.05,
**P < 0.01 vs. blank group;
$^{\triangle}$P < 0.05,
$^{\triangle\triangle}$P < 0.01 vs. model group.

4. Conclusion

The animal experimental studies demonstrate that the effectiveness of Composition 7 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 7 is effective in resisting allergic rhinitis.

Example 65. Animal Experiment Report of Composition 7 Obtained in Example 7 in Prevention and Treatment of Allergic Asthma 1. Materials and Methods
1.1 Sources of Samples The test drug was Composition 7 (Radix Panacis Quinquefolii, Ganoderma, Cordyceps and Flos Rosae Rugosae) provided by Jiangzhong Pharmaceutical Co. Ltd. as composite powder. 1 g dry composite powder was equivalent to 12.19 g total crude drugs.

1.2 Laboratory Animals
The same as in Example 53.
1.3 Primary Reagents
The same as in Example 53.
1.4 Primary Instruments
The same as in Example 53.
2. Experimental Methods
2.1 Effect on Allergic Asthma in Rats Caused by OVA
2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on low, medium and high doses of Composition 7, with 10 animals in each group.

2.1.2 Establishment of Rat Allergic Asthma Animal Models
The same as in Example 53.
2.1.3 Dosage Regime The daily intake of the test drug Composition 7 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (8.20 mg dry powder/ml, 16.41 mg dry powder/ml, 49.22 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 7 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.

2.1.4 Recording of Latent Period of Asthma in Rats
The same as in Example 53.

2.1.5 Measurements of IL-4 and IFN-γ Levels
The same as in Example 53.

2.1.6 Measurement of EOS Content in the Lung Tissues
The same as in Example 53.

2.2 Effect on Allergic Asthma in Guinea Pigs Caused by a Mixed Gas of Ach and his 2.2.1. The Same as in 2.1.1.

2.2.2 Establishment of Guinea Pig Allergic Asthma Animal Models
The same as in Example 53.

2.2.3 Dosage Regime
The same as in 2.1.3.

2.2.4 Recording of Latent Period of Asthma
The same as in 2.1.4.1.

2.2.5 Measurement of IgE in Serum and BALF
The same as in Example 53.

2.3 Statistic Method
The same as in Example 53.

3. Results 3.1 Effect of Composition 7 on Allergic Asthma in Rats Caused by OVA 3.1.1 Effect on the Latent Period of Asthma Induced in Rats
Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged ($P<0.05$ or $P<0.01$).

TABLE 1

Effect of Composition 7 on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 75.46 ± 13.57** | 76.92 ± 12.05** |
| Positive control group | 10 | 0.5 mg/kg | 72.88 ± 10.96** | 156.30 ± 21.44$^{\Delta\Delta}$ |
| Test drug low-dose group | 10 | 1.0 | 73.72 ± 14.20** | 86.27 ± 20.88 |
| Test drug medium-dose group | 10 | 2.0 | 72.65 ± 14.33** | 95.64 ± 22.62$^{\Delta}$ |
| Test drug high-dose group | 10 | 6.0 | 73.19 ± 13.36** | 102.68 ± 23.89$^{\Delta\Delta}$ |

Note:
**$P < 0.01$ vs. blank group;
$^{\Delta}P < 0.05$,
$^{\Delta\Delta}P < 0.01$ vs. model group.

3.1.2 Effect on Serum IL-4 and IFN-γ Levels in Rats
Experimental results were shown in Table 2. As compared to the blank control group, the model group showed a significantly decreased serum IFN-γ level ($P<0.01$) but a significantly increased serum IL-4 level ($P<0.01$), indicating a severe imbalance of the IFN-γ/IL-4 ratio during asthma onsets. As compared to the model group, the dexamethasone group and the test drug medium- and high-dose groups all showed a significantly decreased IL-4 level ($P<0.05$ or $P<0.01$) and a significantly increased IFN-γ level ($P<0.05$ or $P<0.01$), indicating that the test drug can redress the imbalanced IFN-γ/IL-4 ratio.

TABLE 2

Effect of Composition 7 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.84 ± 2.66 | 23.87 ± 4.26 |
| Model control group | — | 10 | 22.18 ± 3.09** | 12.45 ± 3.35** |
| Positive control group | 0.5 mg/kg | 10 | 12.90 ± 4.67$^{\Delta\Delta}$ | 19.29 ± 4.04$^{\Delta\Delta}$ |
| Test drug low-dose group | 1.0 | 10 | 20.21 ± 3.56 | 13.66 ± 3.21 |
| Test drug medium-dose group | 2.0 | 10 | 18.90 ± 4.06$^{\Delta}$ | 15.87 ± 3.26$^{\Delta}$ |
| Test drug high-dose group | 6.0 | 10 | 16.97 ± 3.54$^{\Delta\Delta}$ | 18.92 ± 4.24$^{\Delta\Delta}$ |

Note:
**$P < 0.01$ vs. blank group;
$^{\Delta}P < 0.05$,
$^{\Delta\Delta}P < 0.01$ vs. model group.

3.1.3 Effect on the EOS Content in Rat Lung Tissues
Experimental results were shown in Table 3. The number of EOS in rats in the model group significantly increased ($P<0.01$). As compared to the model group, the positive control group and the test drug medium- and high-dose groups showed a significantly decreased number of EOS ($P<0.01$), indicating that Composition 7 is effective in treating allergic asthma possibly by reducing the EOS content in rat lung tissues.

TABLE 3

Effect of Composition 7 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | 2.60 ± 0.92 |
| Model control group | — | 10 | 105.72 ± 14.56** |
| Positive control group | 0.5 mg/kg | 10 | 35.64 ± 6.18$^{\Delta\Delta}$ |
| Test drug low-dose group | 1.0 | 10 | 93.76 ± 11.90 |
| Test drug medium-dose group | 2.0 | 10 | 79.47 ± 12.08$^{\Delta\Delta}$ |

TABLE 3-continued

Effect of Composition 7 on the EOS content in rat lung tissues ($\bar{x} \pm s$)

| Groups | Dose (g crude drug/kg) | Number of animals | EOS (cells/HP) |
|---|---|---|---|
| Test drug high-dose group | 6.0 | 10 | 68.56 ± 8.32$^{\Delta\Delta}$ |

Note:
**$P < 0.01$ vs. blank group;
$^{\Delta\Delta}P < 0.01$ vs. model group.

3.2 Effect of Composition 7 on Allergic Asthma in Guinea Pigs Caused by a Mixed Gas of Ach and His 3.2.1 Effect on the Latent Period of Asthma Induced in Guinea Pigs Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged ($P < 0.05$ or $P < 0.01$), which indicates that Composition 7 greatly improves the asthmatic symptoms in guinea pig.

TABLE 4

Effect of Composition 7 on the latent period of asthma induced in guinea pigs ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 74.33 ± 11.26** | 72.87 ± 11.21** |
| Positive control group | 10 | 0.5 mg/kg | 70.68 ± 9.65** | 150.46 ± 16.80$^{\Delta\Delta}$ |
| Test drug low-dose group | 10 | 1.0 | 72.92 ± 10.65** | 82.96 ± 21.65 |
| Test drug medium-dose group | 10 | 2.0 | 73.67 ± 11.86** | 96.44 ± 20.27$^{\Delta}$ |
| Test drug high-dose group | 10 | 6.0 | 75.42 ± 10.45** | 113.35 ± 25.92$^{\Delta\Delta}$ |

Note:
**$P < 0.01$ vs. blank group;
$^{\Delta}P < 0.05$,
$^{\Delta\Delta}P < 0.01$ vs. model group.

3.2.2 Effect on the Total IgE in Serum and BALF of Guinea Pigs

Experimental results were shown in Table 5. The total IgE content in serum and BALF in the model group significantly increased ($P < 0.01$). As compared to the model group, the total IgE contents in serum and BALF in the dexamethasone group and in the groups on the medium and high doses of the test drug all significantly decreased ($P < 0.01$ or $P < 0.05$), indicating that both dexamethasone and the test drug can inhibit allergic inflammatory response in guinea pigs' lung and improve asthmatic symptoms.

TABLE 5

Effect of Composition 7 on the total IgE serum and BALF of guinea pigs ($\bar{x} \pm s$)

| Groups | Dose (g crude drug/kg) | Number of animals | Serum (U/L) | BALF (U/L) |
|---|---|---|---|---|
| Blank control group | — | 10 | 2.04 ± 0.83 | 3.72 ± 0.76 |
| Model control group | — | 10 | 5.69 ± 1.22** | 5.41 ± 1.38** |
| Positive control group | 0.5 mg/kg | 10 | 3.70 ± 1.26$^{\Delta\Delta}$ | 3.50 ± 0.78$^{\Delta\Delta}$ |
| Test drug low-dose group | 1.0 | 10 | 5.24 ± 2.45 | 4.36 ± 1.21 |
| Test drug medium-dose group | 2.0 | 10 | 4.28 ± 1.02$^{\Delta}$ | 3.88 ± 1.49$^{\Delta}$ |
| Test drug high-dose group | 6.0 | 10 | 3.95 ± 1.34$^{\Delta\Delta}$ | 3.65 ± 0.91$^{\Delta\Delta}$ |

Note:
**$P < 0.01$ vs. blank group;
$^{\Delta}P < 0.05$,
$^{\Delta\Delta}P < 0.01$ vs. model group.

3.2.3 Effect on the EOS Content in Guinea Pigs' Lung Tissues

Experimental results were shown in Table 6. As compared to the blank control group, the level of EOS counts in guinea pigs in the model group significantly increased ($P < 0.01$). As compared to the model group, the level of EOS counts in the positive control group and the test drug medium- and high-dose groups significantly decreased ($P < 0.01$), indicating that Composition 7 is effective in treating allergic asthma possibly by decreasing the EOS content in guinea pigs' lung tissues.

TABLE 6

Effect of Composition 7 on the EOS content in guinea pigs' lung tissues ($\bar{x} \pm s$)

| Groups | Dose (g crude drug/kg) | Number of animals | EOS (cells/HP) |
|---|---|---|---|
| Blank control group | — | 10 | 5.40 ± 2.67 |
| Model control group | — | 10 | 90.613 ± 13.25** |
| Positive control group | 0.5 mg/kg | 10 | 31.70 ± 9.52$^{\Delta\Delta}$ |
| Test drug low-dose group | 1.0 | 10 | 86.80 ± 11.93 |
| Test drug medium-dose group | 2.0 | 10 | 75.60 ± 13.41$^{\Delta}$ |
| Test drug high-dose group | 6.0 | 10 | 55.72 ± 15.54$^{\Delta\Delta}$ |

Note:
**$P < 0.01$ vs. blank;
$^{\Delta\Delta}P < 0.01$ vs. model group.

4. Conclusion

The animal experimental studies demonstrate that Composition 7 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 7 is considered effective in resisting allergic asthma.

Example 66. Animal Experiment Report of Composition 8 Obtained in Example 8 Against Allergy and Allergic Dermatitis 1. Materials and Methods
1.1 Sources of Samples The test drug was Composition 8 (Radix Panacis Quinquefolii, Ganoderma, fermented *Cordyceps sinensis* powder, Flos Rosae Rugosae and Cordyceps) provided by Jiangzhong Pharmaceutical Co. Ltd. as composite powder. 1 g dry composite powder was equivalent to 13.78 g total crude drugs. Its daily intake recommended for one person was 24 g crude drug/60 kg body weight.

1.2 Laboratory Animals

The same as in Example 51.

1.3 Primary Reagents

The same as in Example 51.

1.4 Primary Instruments

The same as in Example 51.

2. Experimental Methods
2.1 Animal Grouping

Animals were randomly divided into groups with 10 animals per group based on the body weights. A model control group, groups on the low, medium and high doses of Composition 8, and a positive drug control group (prednisone) were established.

2.2 Dosage Regime

The daily intake of test drug Composition 8 recommended for one person was 24 g crude drug/60 kg body weight. On the basis thereof, the calculated daily intake for a mouse was: low dose group: 2.0 g crude drug/kg body weight; medium dose group: 4.0 g crude drug/kg body weight; high dose group: 12.0 g crude drug/kg body weight, which were 5, 10 and 30 times the daily intake for a human, respectively. Samples were prepared into intragastric solutions at corresponding concentrations (14.515 mg dry powder/ml, 29.03 mg dry powder/ml, and 87.09 mg dry powder/ml) with distilled water to carry out experiments.

The daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (7.255 mg dry powder/ml, 14.51 mg dry powder/ml, and 43.53 mg dry powder/ml) with distilled water to carry out experiments.

2.3 Effect of Composition 8 on Passive Anaphylaxis (PCA) in Rats Caused by Ovalbumin
2.3.1 Preparation of Antiserum The same as in Example 51.

2.3.2 Establishment of the Rat Anti-Ovalbumin Serum Models[1]

Anti-ovalbumin serum was taken and diluted at 1:4 or 1:8 with physiological saline. 50 rats were randomly divided into 5 groups, i.e., a model control group, groups on the low, medium and high doses of Composition 8, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 8 were intragastrically given test solutions at different concentrations at a dosing volume of 10 ml/kg; the intragastric administration was carried out once per day for 14 consecutive days. On day 15, the back of the rats were shaved, and was intradermally injected with a diluted antiserum at two spots on each side with 0.1 ml per spot. After 48 hours, a 1.0 ml mixed solution of 1% Evans Blue and 1% ovalbumin in physiological saline was injected into the tail vein of each rat. After 30 min, arterial blood was drawn, serum was isolated therefrom, and the histamine content was determined by the method[2]. The rats were then sacrificed, and their back skin was inverted to measure the diameter of blue reaction spots to determine the difference between the dosing groups and the model group. A sample of the rat skin tissue was fixed with neutral formaldehyde, dehydrated with an alcohol gradient, embedded in paraffin, and examined for mast cell degranulation in the tissue[3].

2.3.3 Effect of Composition 8 on Delayed Hypersensitivity in Mouse Auricle Skin Caused by 2,4-Dinitrochlorobenzene[4]

50 mice were randomly divided into 5 groups, i.e., a model control group, groups on the low, medium and high doses of Composition 8, and a positive drug control group (prednisone), with 10 mice per group. A 5% 2,4-dinitrochlorobenzene solution in ethanol was applied onto the abdominal skin (shaved) of the mice for sensitization. Intragastric administration was carried out two days before sensitization; the model control group was intragastrically given an equivalent volume of distilled water; the positive drug control group was intragastrically given prednisone at a dose of 5 mg/kg; the groups on the low, medium and high doses of Composition 8 were intragastrically given corresponding test solutions at a dosing volume of 0.1 ml/10 g body weight; the intragastric administration was carried out once per day for 10 consecutive days. 7 days after sensitization, a 1% 2,4-dinitrochlorobenzene solution was applied onto the right ear, and the mice were sacrificed after 24 hours, and both ears were cut off along the auricle baseline. Discs having a diameter of 8 mm were punctured out at the same position on both ears, precisely weighed on an electronic balance, and the weight difference between the left and right ears was taken as the value for delayed hypersensitivity.

2.3.4 Effect of Composition 8 on Local Itching in Mice Caused by Low-Molecular-Weight Dextran[5]

The mice were randomly divided into 5 groups, i.e., a model control group, groups on the low, medium and high doses of Composition 8, and a positive drug control group (prednisone), with 10 mice per group. Intragastric administration was carried out to the mice once per day for 10 consecutive days. 30 min after the final administration, a 0.0125% low-molecular-weight dextran solution was injected at 0.1 g/10 g into the tail vein. The number of itching events (itching events were indicated by scratching on the head with front paws, scratching on the body with hind paws, and biting on various parts over the body) occurred within 30 min after injection with the low-molecular-weight dextran solution into tail veins of the mice in each group was observed and recorded.

2.3.5 Effect of Composition 8 on Capillary Permeability in Rats[6]

The rats were randomly divided into 5 groups, i.e., a model control group, groups on the low, medium and high doses of Composition 8, and a positive drug control group (prednisone), with 10 rats per group. The model control group was intragastrically given distilled water; the positive drug control group was intragastrically given prednisone at a dose of 5 mg/kg; the groups on the low, medium and high doses of Composition 8 were intragastrically given test solutions at different concentrations at a dosing volume of 10 ml/kg; the intragastric administration was carried out once per day for 10 consecutive days. 1 hour after the final administration, the shaved area (shaved prior to the administration) of the back of the rats was intradermally injected with 1 mg/ml histamine phosphate at a dose of 0.1 ml/rat, and then the tail vein was immediately injected with a 1% Evans Blue aqueous solution at a dose of 1 ml/rat. After 20 minutes, the animals were sacrificed by cervical dislocation. Skin areas with blue spots were cut off and cut into small pieces, soaked in a 5 ml solution of acetone:physiological saline (7:3) for 48 hours, centrifuged, and the absorbance of the supernatant was measured at 610 nm.

2.4 Statistic Method

The same as in Example 51.

3. Results 3.1 Effect of Composition 8 on Passive Anaphylaxis in Rats

Test results were shown in Tables 1 and 2. As compared to the model control group, the low dose group on Composition 8 showed a tendency to decrease in the diameter of blue spots in 1:4 and 1:8 anti-ovalbumin serum-sensitized rats, to decrease in mast cell degranulation, and to decrease in serum histamine content, which however had no statistic significance; the prednisone control group and the groups on the medium and high doses of Composition 8 all showed an effect of significantly decreasing the diameter of blue spots in 1:4 and 1:8 anti-ovalbumin serum-sensitized rats, decreasing the mast cell degranulation, and decreasing the serum histamine content, with significant or highly significant statistic difference. This indicates that Composition 8 had a significant inhibitory effect on passive anaphylaxis in rats.

TABLE 1

Effect of Composition 8 on the diameter of PCA blue spots in rats ($\bar{x} \pm s$)

| Groups | Dose (g crude drug/kg) | Number of animals | Diameter of blue spots (mm) 1:4 | 1:8 |
|---|---|---|---|---|
| Model control group | 0.0 | 10 | 18.14 ± 3.08 | 11.93 ± 2.17 |
| Positive control group | 5.0 mg | 10 | 12.82 ± 2.62** | 8.54 ± 1.82** |
| Test drug low-dose group | 1.2 | 10 | 16.27 ± 2.75 | 10.81 ± 1.64 |
| Test drug medium-dose group | 2.4 | 10 | 15.04 ± 2.80* | 9.94 ± 1.47* |
| Test drug high-dose group | 7.2 | 10 | 13.89 ± 2.62** | 9.36 ± 1.80** |

*P < 0.05,
**P < 0.01 vs. model control group.

TABLE 2

Effect of Composition 8 on the mast cell degranulation and serum histamine content in PCA rats ($\bar{x} \pm s$)

| Groups | Dose (g crude drug/kg) | Number of animals | Degranulation | Histamine fluorescence (mg · L) |
|---|---|---|---|---|
| Model control group | 0.0 | 10 | 60.24 ± 12.47 | 4.28 ± 0.87 |
| Positive control group | 5.0 mg | 10 | 17.95 ± 11.82** | 2.25 ± 0.76** |
| Test drug low-dose group | 1.2 | 10 | 49.72 ± 10.98 | 3.52 ± 0.80 |
| Test drug medium-dose group | 2.4 | 10 | 45.90 ± 11.04* | 3.30 ± 0.69* |
| Test drug high-dose group | 7.2 | 10 | 33.16± 10.56** | 2.54 ± 0.83** |

*P < 0.05,
**P < 0.01 vs. model control group.

3.2 Effect of Composition 8 on Delayed Hypersensitivity in Mouse Auricle Skin Caused by 2,4-Dinitrochlorobenzene The results were shown in Table 3. As compared to the model control group, the swelling degree of mouse auricle discs significantly decreased in the groups on the medium and high doses of Composition 8, indicating that Composition 8 had a good inhibitory effect on delayed hypersensitivity in mouse auricle skin caused by 2,4-dinitrochlorobenzene.

TABLE 3

Effect of Composition 8 on delayed hypersensitivity in mouse auricle skin caused by 2,4-dinitrochlorobenzene ($\bar{x} \pm s$)

| Groups | Dose (g crude drug/kg) | Number of animals | swelling degree of mouse auricle discs (mg) |
|---|---|---|---|
| Model control group | 0.0 | 10 | 6.73 ± 0.65 |
| Positive control group | 5.0 mg | 10 | 4.60 ± 0.82** |
| Test drug low-dose group | 2.0 | 10 | 6.04 ± 0.97 |
| Test drug medium-dose group | 4.0 | 10 | 5.82 ± 0.83* |
| Test drug high-dose group | 12.0 | 10 | 5.08 ± 0.64** |

*P < 0.05,
**P < 0.01 vs. model control group.

3.3 Effect of Composition 8 on Local Itching in Mice Caused by Low-Molecular-Weight Dextran The test results were shown in Table 4. As compared to the model control group, the OD value significantly decreased in the rat groups on the medium and high doses of Composition 8, indicating that Composition 8 was significantly effective in decreasing the capillary permeability increase in rats caused by histamine phosphate.

TABLE 4

Effect of Composition 8 on local itching in mice caused by low-molecular-weight dextran ($\bar{x} \pm s$)

| Groups | Dose (g crude drug/kg) | Number of animals | Number of itching events (30 min) |
|---|---|---|---|
| Model control group | 0.0 | 10 | 26.60 ± 6.22 |
| Positive control group | 5.0 mg | 10 | 14.88 ± 5.08** |
| Test drug low-dose group | 2.0 | 10 | 21.53 ± 5.21 |
| Test drug medium-dose group | 4.0 | 10 | 18.94 ± 6.04* |
| Test drug high-dose group | 12.0 | 10 | 15.62 ± 4.78** |

*P < 0.05,
**P < 0.01 vs. model control group.

3.4 Effect of Composition 8 on Capillary Permeability in Rats

The test results were shown in Table 5. As compared to the model control group, the OD value significantly decreased in the rat groups on the medium and high doses of Composition 8, indicating that Composition 8 was significantly effective in decreasing the capillary permeability increase in rats caused by histamine phosphate.

TABLE 5

Effect of Composition 8 on capillary permeability in rats ($\bar{x} \pm s$)

| Groups | Dose (g crude drug/kg) | Number of animals | OD value |
| --- | --- | --- | --- |
| Model control group | 0.0 | 10 | 0.962 ± 0.069 |
| Positive control group | 5.0 mg | 10 | 0.662 ± 0.073** |
| Test drug low-dose group | 1.2 | 10 | 0.890 ± 0.084 |
| Test drug medium-dose group | 2.4 | 10 | 0.856 ± 0.089* |
| Test drug high-dose group | 7.2 | 10 | 0.724 ± 0.097** |

*$P < 0.05$,
**$P < 0.01$ vs. model control group.

4. Conclusion

The animal experimental studies demonstrate that Composition 8 is significantly effective in inhibiting passive anaphylaxis in rats caused by ovalbumin, that Composition 8 is effective in inhibiting delayed hypersensitivity in mouse auricle skin caused by 2,4-dinitrochlorobenzene, and that Composition 8 is significantly effective in decreasing the capillary permeability increase in rats caused by histamine phosphate. The above results indicate good effectiveness of Composition 8 in resisting allergy and in preventing and treating allergic diseases such as allergic dermatitis and urticaria.

Example 67. Animal Experiment Report of Composition 8 Obtained in Example 8 in Prevention and Treatment of Allergic Rhinitis 1. Materials and Methods
1.1 Sources of Samples The test drug was Composition 8 (Radix Panacis Quinquefolii, Ganoderma, fermented *Cordyceps sinensis* powder, Flos Rosae Rugosae and Cordyceps) provided by Jiangzhong Pharmaceutical Co. Ltd. as composite powder. 1 g dry composite powder was equivalent to 13.78 g total crude drugs.

1.2 Laboratory Animals
The same as in Example 52.
1.3 Primary Reagents
The same as in Example 52.
1.4 Primary Instruments
The same as in Example 52.
2. Experimental Methods
2.1 Effect on Allergic Rhinitis in Rats Caused by OVA
2.1.1 Animal Grouping Rats were randomly divided into two groups, i.e., a blank control group of 10 animals and a modeling group of 70 animals. After a successful modeling, the rats were randomly divided, on the basis of their score, into the following groups: a model control group, a positive drug group (Bi-yan-kang group), and groups on low, medium and high doses of Composition 8, with 10 animals in each group.

2.1.2 Dosage Regime

The daily intake of the test drug Composition 8 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (7.26 mg dry powder/ml, 14.51 mg dry powder/ml, and 43.54 mg dry powder/ml) with distilled water to carry out experiments. The volume of intragastric administration was calculated as 1.0 ml/100 g body weight. The blank control group and the allergic rhinitis model group were intragastrically given an equivalent volume of physiological saline; the Bi-yan-kang group was given the drug at a dose of 410 mg/kg. The intragastric administration was initiated after a successful modeling and carried out once per day for 21 consecutive days.

2.1.3 Establishment of Rat Allergic Rhinitis Animal Models
The same as in Example 52.
2.1.4 Assay Indicators
The same as in Example 52.
2.1.4.1 Blood cAMP and cGMP Measurement
The same as in Example 52.
2.1.4.2 Nasal Mucosal Mast Cell Counting
The same as in Example 52.
2.2 Effect on Guinea Pig Allergic Rhinitis Caused by TDI
2.2.1. The Same as in 2.1.1.
2.2.2. The Same as in 2.1.2.
2.2.3 Establishment of Guinea Pig Allergic Rhinitis Animal Models
The same as in Example 52.
2.2.4 Assay Indicators
The same as in Example 52.
2.2.4.1 Guinea Pig Behavior Observation
The same as in Example 52.
2.2.4.2 Counts of Eosinophils (EOS) in Nasal Secretion
The same as in Example 52.
2.2.4.3 Total Serum IgE and Blood Histamine Measurement
The same as in Example 52.
2.2.4.4 Nasal Mucosa Thickness Measurement
The same as in Example 52.
2.3 Statistic Method Experimental data were presented in $\bar{X} \pm S$. One-way ANOVA analysis was employed to compare the differences among the blank control group, the model control group and the groups on various doses of Composition 8. $P<0.05$ was considered as significantly different. $P<0.01$ was considered as highly significantly different.

3. Results
3.1 Effect of Composition 8 on Allergic Rhinitis in Rats Caused by Ovalbumin
3.1.1 Effect on Rat Behavior Results were shown in Table 2. After the modeling, the scores for signs of the rats in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased ($P<0.01$ or $P<0.05$), and the low-dose group also showed a tendency to decrease.

TABLE 2

Effect of Composition 8 on symptom scores of allergic rhinitis in rats before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.36 ± 0.38 | 0.44 ± 0.23 | 0.35 ± 0.29 | 0.35 ± 0.16 |
| Model control group | 10 | — | 6.78 ± 1.62** | 6.70 ± 1.37** | 6.98 ± 1.42** | 6.64 ± 1.06** |
| Bi-yan-kang group | 10 | 0.41 | 6.53 ± 1.14** | 3.14 ± 0.98^ΔΔ | 3.77 ± 1.14^ΔΔ | 2.76 ± 0.98^ΔΔ |
| Test drug low-dose group | 10 | 1.0 | 6.84 ± 1.25** | 5.90 ± 0.75 | 5.72 ± 1.29 | 5.78 ± 1.16 |
| Test drug medium-dose group | 10 | 2.0 | 6.42 ± 1.44** | 5.37 ± 1.33^Δ | 5.23 ± 1.53^Δ | 4.26 ± 1.35^ΔΔ |
| Test drug high-dose group | 10 | 6.0 | 6.79 ± 1.18** | 4.76 ± 0.92^ΔΔ | 4.30 ± 1.26^ΔΔ | 4.34 ± 1.23^ΔΔ |

Note:
**$P < 0.01$ vs. blank control group;
$^\Delta P < 0.05$,
$^{\Delta\Delta} P < 0.01$ vs. model group.

3.1.2 Effect of Composition 8 on Serum cAMP and cGMP Levels in Rats

Experimental results were shown in Table 3. As compared to the blank control group, the model group showed a significantly decreased serum cAMP level ($P<0.01$) and a significantly increased serum cGMP level ($P<0.01$). As compared to the model control group, the Bi-yan-kang group and all test drug groups showed a significantly increased serum cAMP level ($P<0.01$ or $P<0.05$); the Bi-yan-kang group and the test drug medium- and high-dose groups showed a significantly decreased serum cGMP level ($P<0.01$ or $P<0.05$), and the low dose group also showed a tendency to decrease.

3.1.3 Effect of Composition 8 on Mast Cells in Rat Nasal Mucosa

The experimental results were shown in Table 3. The number of nasal mucosa mast cells in the model control group significantly increased with a highly significant difference ($P<0.01$). As compared to the model control group, the number of nasal mucosa mast cells in the Bi-yan-kang group and the test drug treatment groups all significantly decreased with a significant difference ($P<0.01$)

TABLE 3

Effect of Composition 8 on serum cAMP and cGMP levels and nasal mucosa mast cells in rats ($\bar{x} \pm s$)

| Groups | Dose (g crude drug/kg) | Number of animals | cAMP (pmol/ml) | cGMP (pmol/ml) | Mast cell counts (cells) |
|---|---|---|---|---|---|
| Blank control group | — | 10 | 20.24 ± 4.87 | 9.88 ± 2.56 | 1.74 ± 1.38 |
| Model control group | — | 10 | 10.20 ± 3.90** | 14.95 ± 4.96** | 14.39 ± 4.83** |
| Bi-yan-kang group | 0.41 | 10 | 18.40 ± 3.49^ΔΔ | 9.08 ± 2.36^ΔΔ | 5.76 ± 2.09^ΔΔ |
| Test drug low-dose group | 1.0 | 10 | 14.25 ± 3.80^Δ | 12.55 ± 3.85 | 9.71 ± 3.57^ΔΔ |
| Test drug medium-dose group | 2.0 | 10 | 15.95 ± 5.34^Δ | 10.70 ± 2.72^Δ | 8.87 ± 3.11^ΔΔ |
| Test drug high-dose group | 6.0 | 10 | 16.85 ± 4.19^ΔΔ | 9.10 ± 3.86^ΔΔ | 6.64 ± 2.16^ΔΔ |

Note:
*$P < 0.05$,
**$P < 0.01$ vs. blank group;
$^\Delta P < 0.05$,
$^{\Delta\Delta} P < 0.01$ vs. model group.

3.2 Effect of Composition 8 on Allergic Rhinitis in Guinea Pigs Caused by TDI 3.2.1 Effect on Guinea Pig Behaviors Results were shown in Table 4. After the modeling, the scores for signs of the guinea pigs in each modeled group were qualified without significant difference therebetween, indicating a successful modeling. After the dosing and treatment, as compared to the model control group, the scores for signs in the test drug medium- and high-dose groups and in the Bi-yan-kang group all significantly decreased (P<0.01 or P<0.05), and the low-dose group also showed a tendency to decrease.

TABLE 4

Effect of Composition 8 on symptom scores of allergic rhinitis in guinea pigs before and after dosing ($\bar{x} \pm s$)

| Groups | Number of animals | Dose (g crude drug/kg) | Before dosing | After dosing Day 7 | Day 14 | Day 21 |
|---|---|---|---|---|---|---|
| Blank control group | 10 | — | 0.55 ± 0.71 | 0.41 ± 0.42 | 0.31 ± 0.39 | 0.45 ± 0.61 |
| Model control group | 10 | — | 6.18 ± 1.32** | 6.57 ± 1.27** | 6.64 ± 1.12** | 6.10 ± 0.86** |
| Bi-yan-kang group | 10 | 0.41 | 6.73 ± 1.07** | 5.24 ± 0.60$^\Delta$ | 5.72 ± 0.82$^\Delta$ | 4.98 ± 1.18$^\Delta$ |
| Test drug low-dose group | 10 | 1.0 | 6.64 ± 1.20** | 5.46 ± 1.25 | 5.59 ± 0.88 | 5.13 ± 1.42 |
| Test drug medium-dose group | 10 | 2.0 | 6.52 ± 1.17** | 5.13 ± 1.38$^\Delta$ | 4.66 ± 1.42$^{\Delta\Delta}$ | 4.20 ± 0.87$^{\Delta\Delta}$ |
| Test drug high-dose group | 10 | 6.0 | 6.79 ± 1.23** | 4.46 ± 1.17$^{\Delta\Delta}$ | 3.83 ± 0.74$^{\Delta\Delta}$ | 3.77 ± 0.83$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.2 Effect on Blood Histamine and Total Serum IgE in Guinea Pigs

Experimental results were shown in Table 5. As compared to the blank control group, the blood histamine and the total serum IgE in the model group both increased (P<0.01), indicating a successful experimental modeling. As compared to the model group, the fluorescence absorbance of histamine and the total serum IgE concentration in the test drug medium- and high-dose groups and in the Bi-yan-kang group significantly decreased (P<0.01 or P<0.05), wherein the histamine in the medium- and high-dose groups decreased to near the normal level, indicating that Composition 8 was effective in treating allergic rhinitis by inhibiting the blood histamine level and serum IgE.

TABLE 5

Effect of Composition 8 on blood histamine and total serum IgE in guinea pigs ($\bar{x} \pm s$)

| Groups | Number of animals | Dose (g crude drug/kg) | Histamine fluorescence (mg · L) | IgE (IU · ml$^{-1}$) |
|---|---|---|---|---|
| Blank control group | 10 | — | 2.04 ± 0.45 | 0.128 ± 0.032 |
| Model control group | 10 | — | 3.25 ± 0.98** | 0.172 ± 0.044** |
| Bi-yan-kang group | 10 | 0.41 | 2.03 ± 0.37$^{\Delta\Delta}$ | 0.112 ± 0.014$^{\Delta\Delta}$ |
| Test drug low-dose group | 10 | 1.0 | 3.10 ± 0.55 | 0.146 ± 0.038 |
| Test drug medium-dose group | 10 | 2.0 | 2.42 ± 0.32$^\Delta$ | 0.138 ± 0.015$^\Delta$ |
| Test drug high-dose group | 10 | 6.0 | 2.19 ± 0.28$^{\Delta\Delta}$ | 0.130 ± 0.020$^{\Delta\Delta}$ |

Note:
*P < 0.05,
**P < 0.01 vs. blank group;
$^\Delta$P < 0.05,
$^{\Delta\Delta}$P < 0.01 vs. model group.

3.2.3 Effect on Eosinophils (EOS) in Nasal Secretion of Guinea Pigs

Experimental results were shown in Table 6. The number of eosinophils in the model group significantly increased (P<0.01). As compared to the model group, the number of eosinophils in the Bi-yan-kang group and the drug treatment groups all significantly decreased (P<0.05 or P<0.01).

3.2.4 Effect on the Nasal Mucosa Thickness in Guinea Pigs

Experimental results were shown in Table 6. As a result, as compared to the blank control group, in the model group, the mucosal epithelium on the nasal septum of the guinea pigs was detached to various extents, having a nonuniform thickness and an unclear basal structure; the venules and capillaries in the lamina propria showed apparent dilation, the tissue space expanded, and the mucosa thickness significantly increased (P<0.01). As compared to the model control group, the above pathological changes in the Bi-yan-kang group and in the drug treatment groups were alleviated, and the mucosa thickness significantly decreased (P<0.01).

TABLE 6

Effect of Composition 8 on EOS in nasal secretion and nasal mucosa thickness in guinea pigs ($\bar{x} \pm s$)

| Groups | Dose (g crude drug/kg) | Number of animals | Number of EOS ($\times 10^{-9}$/L) | Mucosa thickness (mm) |
|---|---|---|---|---|
| Blank control group | — | 10 | 2.63 ± 1.02 | 0.151 ± 0.055 |
| Model control group | — | 10 | 18.77 ± 4.28** | 0.289 ± 0.082** |
| Bi-yan-kang group | 0.41 | 10 | 13.19 ± 3.70$^{\Delta\Delta}$ | 0.188 ± 0.039$^{\Delta\Delta}$ |
| Test drug low-dose group | 1.0 | 10 | 13.38 ± 4.21$^{\Delta\Delta}$ | 0.188 ± 0.058$^{\Delta\Delta}$ |
| Test drug medium-dose group | 2.0 | 10 | 13.52 ± 3.46$^{\Delta\Delta}$ | 0.182 ± 0.079$^{\Delta\Delta}$ |
| Test drug high-dose group | 6.0 | 10 | 12.24 ± 2.70$^{\Delta\Delta}$ | 0.177 ± 0.071$^{\Delta\Delta}$ |

Note:
*P < 0.05,
**P < 0.01 vs. blank group;
$^\Delta$P < 0.05,
$^{\Delta\Delta}$P < 0.01 vs. model group.

4. Conclusion

The animal experimental studies demonstrate that the effectiveness of Composition 8 is primarily reflected in the following aspects: 1) it is capable of significantly decreasing the nasal symptom score of modeled rats, increasing the serum cAMP level and decreasing the cGMP level in rats with allergic rhinitis; 2) decreasing the number of mast cells in rat nasal mucosa and decreasing their infiltration in inflamed sites; 3) it is capable of decreasing the nasal symptom score of modeled guinea pigs; 4) decreasing the number of EOSs in guinea pig's nasal secretion and reducing infiltration of EOSs in inflamed sites; 5) it is capable of significantly decreasing the blood histamine concentration in guinea pigs and reducing inflammatory mediators; 6) alleviating swelling in nasal mucosa of guinea pigs. According to the results of the experimental studies, it is considered that Composition 8 is effective in resisting allergic rhinitis.

Example 68. Animal Experiment Report of Composition 8 Obtained in Example 8 in Prevention and Treatment of Allergic Asthma 1. Materials and Methods
1.1 Sources of Samples The test drug was Composition 8 (Radix Panacis Quinquefolii, Ganoderma, fermented *Cordyceps sinensis* powder, Flos Rosae Rugosae and Cordyceps) provided by Jiangzhong Pharmaceutical Co. Ltd. as composite powder. 1 g dry composite powder was equivalent to 13.78 g total crude drugs.

1.2 Laboratory Animals
The same as in Example 53.
1.3 Primary Reagents
The same as in Example 53.
1.4 Primary Instruments
The same as in Example 53.

2. Experimental Methods
2.1 Effect on Allergic Asthma in Rats Caused by OVA
2.1.1 Animal Grouping Rats (half thereof were male and the other half female) were randomly divided into two groups, i.e., a blank control group of 10 animals and a modeling group of 70 animals. After a successful modeling, the rats were randomly divided into the following groups: a model control group, a positive drug group (dexamethasone group), and groups on low, medium and high doses of Composition 8, with 10 animals in each group.

2.1.2 Establishment of Rat Allergic Asthma Animal Models
The same as in Example 53.
2.1.3 Dosage Regime The daily intake of the test drug Composition 8 composite powder recommended for one person was 24 g crude drug/60 kg body weight. On the basis thereof, the calculated daily intake for a rat was: low dose group: 1.0 g crude drug/kg body weight; medium dose group: 2.0 g crude drug/kg body weight; high dose group: 6.0 g crude drug/kg body weight, which were 2.5, 5 and 15 times the daily intake for a human, respectively. Samples were prepared into intragastric solutions at corresponding concentrations (7.26 mg dry powder/ml, 14.51 mg dry powder/ml, 43.54 mg dry powder/ml) to carry out experiments. The volume of intragastric administration was calculated as 1.0 ml/100 g body weight. The model control group was intragastrically given an equivalent volume of 0.9% physiological saline 30 minutes before challenging; and the positive drug group was given dexamethasone at a dose of 0.5 mg/kg 30 min before each challenging[2]. The groups on the low, medium and high doses of Composition 8 were each intragastrically given the respective dose of the test drug 30 min before each challenging. Meanwhile, the blank control group was intraperitoneally injected with, challenged by atomization with, or intragastrically administered with an equivalent volume of 0.9% physiological saline. The intragastric administration was carried out once per day for 21 consecutive days.

2.1.4 Recording of Latent Period of Asthma in Rats
The same as in Example 53.
2.1.5 Measurements of IL-4 and IFN-γ Levels
The same as in Example 53.
2.1.6 Measurement of EOS Content in the Lung Tissues
The same as in Example 53.
2.2 Effect on Allergic Asthma in Guinea Pigs Caused by a Mixed Gas of Ach and his
2.2.1. The Same as in 2.1.1.
2.2.2 Establishment of Guinea Pig Allergic Asthma Animal Models
The same as in Example 53.
2.2.3 Dosage Regime
The same as in 2.1.3.
2.2.4 Recording of Latent Period of Asthma
The same as in 2.1.4.1.
2.2.5 Measurement of IgE in Serum and BALF
The same as in Example 53.
2.3 Statistic Method
The same as in Example 53.

3. Results
3.1 Effect of Composition 8 on Allergic Asthma in Rat Caused by OVAs
3.1.1 Effect on the Latent Period of Asthma Induced in Rats Results were shown in Table 1. The latent periods of asthma induced in rats from each modeled group were qualified without significant difference therebetween, which indicates a successful modeling. After the dosing and treatment, as compared to the model control group, the latent periods of asthma induced in the rats in the positive control group and the test drug medium- and high-dose groups were all significantly prolonged (P<0.05 or P<0.01).

TABLE 1

Effect of Composition 8 on the latent period of asthma induced in rats ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 78.24 ± 13.92** | 75.44 ± 12.76** |
| Positive control group | 10 | 0.5 mg/kg | 73.66 ± 11.19** | 159.87 ± 20.38$^{\Delta\Delta}$ |
| Test drug low-dose group | 10 | 1.0 | 76.63 ± 15.20** | 85.13 ± 21.42 |
| Test drug medium-dose group | 10 | 2.0 | 78.42 ± 14.17** | 96.60 ± 20.75$^{\Delta}$ |
| Test drug high-dose group | 10 | 6.0 | 78.49 ± 17.23** | 106.54 ± 20.97$^{\Delta\Delta}$ |

Note:
**P < 0.01 vs. blank group;
$^{\Delta}$P < 0.05,
$^{\Delta\Delta}$P < 0.01 vs. model group.

3.1.2 Effect on Serum IL-4 and IFN-γ Levels in Rats

Experimental results were shown in Table 2. As compared to the blank control group, the model group showed a significantly decreased serum IFN-γ level (P<0.01) but a significantly increased serum IL-4 level (P<0.01), indicating a severe imbalance of the IFN-γ/IL-4 ratio during asthma onsets. As compared to the model group, the dexamethasone group and the test drug medium- and high-dose groups all showed a significantly decreased IL-4 level (P<0.05 or P<0.01) and a significantly increased IFN-γ level (P<0.05 or P<0.01), indicating that the test drug can redress the imbalanced IFN-γ/IL-4 ratio.

TABLE 2

Effect of Composition 8 on serum IL-4 and IFN-γ levels in rats ($\bar{x} \pm s$)

| Groups | Dose (g crude drug/kg) | Number of animals | IL-4 (pg/ml) | IFN-γ (pg/ml) |
|---|---|---|---|---|
| Blank control group | — | 10 | 12.75 ± 2.63 | 24.41 ± 4.27 |
| Model control group | — | 10 | 22.55 ± 3.68** | 11.95 ± 3.36** |
| Positive control group | 0.5 mg/kg | 10 | 13.41 ± 4.21$^{\Delta\Delta}$ | 20.16 ± 4.96$^{\Delta\Delta}$ |
| Test drug low-dose group | 1.0 | 10 | 20.67 ± 3.28 | 13.88 ± 3.87 |
| Test drug medium-dose group | 2.0 | 10 | 18.35 ± 4.24$^{\Delta}$ | 15.70 ± 3.92$^{\Delta}$ |
| Test drug high-dose group | 6.0 | 10 | 16.22 ± 3.47$^{\Delta\Delta}$ | 17.46 ± 4.86$^{\Delta\Delta}$ |

Note:
**P < 0.01 vs. blank group;
$^{\Delta}$P < 0.05,
$^{\Delta\Delta}$P < 0.01 vs. model group.

3.1.3 Effect on the EOS Content in Rat Lung Tissues

Experimental results were shown in Table 3. The number of EOS in rats in the model group significantly increased (P<0.01). As compared to the model group, the positive control group and the test drug medium- and high-dose groups showed a significantly decreased number of EOS (P<0.01), indicating that Composition 8 is effective in treating allergic asthma possibly by reducing the EOS content in rat lung tissues.

TABLE 3

Effect of Composition 8 on the EOS content in rat lung tissues ($\bar{x} \pm s$)

| Groups | Dose (g crude drug/kg) | Number of animals | EOS (cells/HP) |
|---|---|---|---|
| Blank control group | — | 10 | 2.24 ± 0.85 |
| Model control group | — | 10 | 103.60 ± 13.94** |
| Positive control group | 0.5 mg/kg | 10 | 28.39 ± 4.26$^{\Delta\Delta}$ |
| Test drug low-dose group | 1.0 | 10 | 93.21 ± 11.29 |
| Test drug medium-dose group | 2.0 | 10 | 72.13 ± 10.34$^{\Delta\Delta}$ |
| Test drug high-dose group | 6.0 | 10 | 65.22 ± 8.49$^{\Delta\Delta}$ |

Note:
**P < 0.01 vs. blank group;
$^{\Delta\Delta}$P < 0.01 vs. model group.

3.2 Effect of Composition 8 on Allergic Asthma in Guinea Pigs Caused by a Mixed Gas of Ach and his

3.2.1 Effect on the Latent Period of Asthma Induced in Guinea Pigs

Results were shown in Table 4. After the modeling, the latent periods of asthma induced in guinea pigs from each modeled group were qualified without significant difference therebetween, which indicates a successful modeling. After the dosing and treatment, as compared to the model control group, the latent periods of asthma induced in the guinea pigs in the positive control group and the test drug medium- and high-dose groups were all significantly prolonged (P<0.05 or P<0.01), which indicates that Composition 8 greatly improves the asthmatic symptoms in guinea pig.

TABLE 4

Effect of Composition 8 on the latent period of asthma induced in guinea pigs ($\bar{x} \pm s$)

| Groups | Number of animals | Dose (g crude drug/kg) | Before dosing | After dosing |
|---|---|---|---|---|
| Blank control group | 10 | — | 360 | 360 |
| Model control group | 10 | — | 77.18 ± 10.92** | 78.00 ± 10.76** |
| Positive control group | 10 | 0.5 mg/kg | 74.63 ± 9.04** | 156.77 ± 16.18△△ |
| Test drug low-dose group | 10 | 1.0 | 76.64 ± 14.20** | 84.03 ± 21.42 |
| Test drug medium-dose group | 10 | 2.0 | 77.92 ± 15.17** | 97.40 ± 24.67△ |
| Test drug high-dose group | 10 | 6.0 | 79.79 ± 19.23** | 110.87 ± 24.53△△ |

Note:
**$P < 0.01$ vs. blank group;
△$P < 0.05$,
△△$P < 0.01$ vs. model group.

3.2.2 Effect on the Total IgE in Serum and BALF of Guinea Pigs

Experimental results were shown in Table 5. The total IgE content in serum and BALF in the model group significantly increased (P<0.01). As compared to the model group, the total IgE contents in serum and BALF in the dexamethasone group and in the groups on the medium and high doses of the test drug all significantly decreased (P<0.01 or P<0.05), indicating that both dexamethasone and the test drug can inhibit allergic inflammatory response in guinea pigs' lung and improve asthmatic symptoms.

TABLE 5

Effect of Composition 8 on the total IgE in serum and BALF of guinea pigs ($\bar{x} \pm s$)

| Groups | Dose (g crude drug/g) | Number of animals | Serum (U/L) | BALF (U/L) |
|---|---|---|---|---|
| Blank control group | — | 10 | 2.10 ± 0.87 | 3.69 ± 0.86 |
| Model control group | — | 10 | 5.72 ± 1.47** | 5.42 ± 1.34** |
| Positive control group | 0.5 mg/kg | 10 | 3.65 ± 1.21△△ | 3.62 ± 0.62△△ |
| Test drug low-dose group | 1.0 | 10 | 5.21 ± 2.08 | 4.25 ± 1.67 |
| Test drug medium-dose group | 2.0 | 10 | 4.35 ± 1.24△ | 3.82 ± 1.55△ |
| Test drug high-dose group | 6.0 | 10 | 3.98 ± 1.19△△ | 3.79 ± 0.86△△ |

Note:
**$P < 0.01$ vs. blank group;
△$P < 0.05$,
△△$P < 0.01$ vs. model group.

3.2.3 Effect on the EOS Content in Guinea Pigs' Lung Tissues

Experimental results were shown in Table 6. As compared to the blank control group, the level of EOS counts in guinea pigs in the model group significantly increased (P<0.01). As compared to the model group, the level of EOS counts in the positive control group and the test drug medium- and high-dose groups significantly decreased (P<0.01), indicating that Composition 8 is effective in treating allergic asthma possibly by decreasing the EOS content in guinea pigs' lung tissues.

TABLE 6

Effect of Composition 8 on the EOS content in guinea pigs' lung tissues ($\bar{x} \pm s$)

| Groups | Dose (g crude drug/kg) | Number of animals | EOS (cells/HP) |
|---|---|---|---|
| Blank control group | — | 10 | 5.26 ± 2.85 |
| Model control group | — | 10 | 94.60 ± 14.98** |
| Positive control group | 0.5 mg/kg | 10 | 30.69 ± 7.35△△ |
| Test drug low-dose group | 1.0 | 10 | 82.38 ± 12.29 |
| Test drug medium-dose group | 2.0 | 10 | 67.35 ± 12.05△△ |
| Test drug high-dose group | 6.0 | 10 | 59.32 ± 11.79△△ |

Note:
**$P < 0.01$ vs. blank group;
△△$P < 0.01$ vs. model group.

4. Conclusion

The animal experimental studies demonstrate that Composition 8 is capable of significantly improving asthmatic symptoms in rats and prolonging the latent period of asthma induced in guinea pigs in the model groups; decreasing the serum IL-4 level, increasing the serum IFN-γ level, and redressing the imbalanced IFN-γ/IL-4 ratio in rats with asthma; decreasing the number of EOSs in lung tissues of rats and guinea pigs, and ameliorating infiltration of EOSs in inflamed sites; decreasing the total IgE content in serum and BALF of guinea pigs, and improving pulmonary inflammatory symptoms. Thus, Composition 8 is considered effective in resisting allergic asthma.

The invention claimed is:
1. A method of preventing or treating allergic diseases, comprising the step of administering to a subject in need thereof a composition, wherein the active ingredients of the composition comprise the following raw materials:
   (i) Ganoderma,
   (ii) Radix Panacis Quinquefolii or Radix Et Rhizoma Ginseng,
   (iii) fermented *Cordyceps sinensis* powder and/or Cordyceps, and
   (iv) Flos Rosae Rugosae.
2. The method of claim 1, characterized in that the active ingredients comprise:
   (i) 5 to 200 parts by weight of Ganoderma,
   (ii) 5 to 150 parts by weight of Radix Panacis Quinquefolii or Radix Et Rhizoma Ginseng,
   (iii) 1 to 90 parts by weight of fermented Cordyceps *sinensis* powder and/or 1 to 120 parts by weight of Cordyceps, and
   (iv) 5 to 90 parts by weight of Flos Rosae Rugosae.

3. The method of claim 1, characterized in that the active ingredients of the composition consist of:
 (i) 5 to 200 parts by weight of Ganoderma,
 (ii) 5 to 90 parts by weight of Flos Rosae Rugosae,
 (iii) 5 to 150 parts by weight of Radix Panacis Quinquefolii or Radix Et Rhizoma Ginseng, and
 (iv) 1 to 90 parts by weight of fermented *Cordyceps sinensis* powder and/or 1 to 120 parts by weight of Cordyceps.

4. The method of claim 1, characterized in that the active ingredients of the composition comprise:
 (i) 20 to 120 parts by weight of Ganoderma,
 (ii) 10 to 60 parts by weight of Flos Rosae Rugosae,
 (iii) 10 to 90 parts by weight of Radix Panacis Quinquefolii or Radix Et Rhizoma Ginseng, and
 (iv) 3 to 60 parts by weight of fermented *Cordyceps sinensis* powder and/or 3 to 90 parts by weight of Cordyceps.

5. The method of claim 1, characterized in that the active ingredients of the composition comprise:
 (i) 40 parts by weight of Ganoderma,
 (ii) 30 parts by weight of Flos Rosae Rugosae,
 (iii) 30 parts by weight of Radix Panacis Quinquefolii or Radix Et Rhizoma Ginseng, and
 (iv) 20 parts by weight of fermented *Cordyceps sinensis* powder and/or 6.7 parts by weight of Cordyceps.

6. The method of claim 1, characterized in that the allergic diseases are allergic rhinitis, allergic dermatitis, allergic asthma, and/or urticaria.

7. The method of claim 1, characterized in that the composition is prepared by a method comprising:
 (i) directly mixing all the raw materials; or
 (ii) mixing all the raw materials, and then extracting them with water and/or alcohol to obtain the composition; or
 (iii) extracting a portion of the raw materials with water and/or alcohol and mixing the extract with the other portion of the raw materials.

8. The method of claim 7, characterized in that the composition is prepared by the following steps:
 1) weighing out all the raw materials; and
 2) extracting the raw materials under reflux with alcohol or water, so as to obtain a liquid extract as the active ingredient, and adding auxiliary agent(s) to prepare various dosage forms.

9. The method of claim 7, characterized in that the composition is prepared by the following steps:
 1) weighing out all the raw materials, adding methanol or ethanol thereto to carry out extraction, recovering methanol or ethanol from the extraction liquid, to obtain Extract I;
 2) evaporating methanol or ethanol from the residual drugs, adding water to carry out extraction, to obtain Extract II; and
 3) combining Extract I and Extract II, carrying out filtration, concentrating the filtrate to an appropriate amount, adding pharmaceutically conventional auxiliary agent(s) to prepare a desired formulation by a pharmaceutically conventional process.

10. The method of claim 1, characterized in that the composition is prepared into dosage form by adding thereto auxiliary agent(s) or excipient(s) which is/are acceptable in health care products, medicaments or products.

11. The method of claim 10, characterized in that the dosage form is any one of a tablet, an oral liquid, a granule, a capsule, an electuary, a pill, powder, a lozenge, a fluid extract, an extract, an injection, and a syrup.

12. A method of preventing or treating allergic diseases, comprising the step of administering to a subject in need thereof a composition, wherein the active ingredients of the composition consist of:
 (i) Ganoderma,
 (ii) Radix Panacis Quinquefolii or Radix Et Rhizoma Ginseng,
 (iii) fermented *Cordyceps sinensis* powder and/or Cordyceps, and
 (iv) one or more materials selected from the group consisting of Flos Rosae Rugosae, Ganoderma spore powder, Ganoderma spore oil, Radix Pseudostellariae, Folium Ginseng, Radix Codonopsis, and Radix Astragali.

13. The method of claim 12, characterized in that the active ingredients of the composition consist of:
 (i) 5 to 200 parts by weight of Ganoderma,
 (ii) 5 to 150 parts by weight of Radix Panacis Quinquefolii or Radix Et Rhizoma Ginseng,
 (iii) 1 to 90 parts by weight of fermented *Cordyceps sinensis* powder and/or 1 to 120 parts by weight of Cordyceps, and
 (iv) one or more materials selected from the group consisting of Flos Rosae Rugosae, Ganoderma spore powder, Ganoderma spore oil, Radix Pseudostellariae, Folium Ginseng, Radix Codonopsis, and Radix Astragali.

14. The method of claim 12, characterized in that the active ingredients of the composition consist of:
 (i) 20 to 120 parts by weight of Ganoderma,
 (ii) 10 to 90 parts by weight of Radix Panacis Quinquefolii or Radix Et Rhizoma Ginseng,
 (iii) 3 to 60 parts by weight of fermented *Cordyceps sinensis* powder and/or 3 to 90 parts by weight of Cordyceps, and
 (iv) one or more materials selected from the group consisting of Flos Rosae Rugosae, Ganoderma spore powder, Ganoderma spore oil, Radix Pseudostellariae, Folium Ginseng, Radix Codonopsis, and Radix Astragali.

15. The method of claim 12, characterized in that the active ingredients of the composition consist of:
 (i) 40 parts by weight of Ganoderma,
 (ii) 30 parts by weight of Radix Panacis Quinquefolii or Radix Et Rhizoma Ginseng,
 (iii) 20 parts by weight of fermented *Cordyceps sinensis* powder and/or 6.7 parts by weight of Cordyceps, and
 (iv) one or more materials selected from the group consisting of Flos Rosae Rugosae, Ganoderma spore powder, Ganoderma spore oil, Radix Pseudostellariae, Folium Ginseng, Radix Codonopsis, and Radix Astragali.

16. The method of claim 12, characterized in that component (iv) is one or more materials selected from the group consisting of 5 to 90 parts by weight of Flos Rosae Rugosae, 5 to 150 parts by weight of Ganoderma spore powder, 1 to 90 parts by weight of Ganoderma spore oil, 10 to 400 parts by weight of Radix Pseudostellariae, 1 to 120 parts by weight of Folium Ginseng, 3 to 400 parts by weight of Radix Codonopsis, and 3 to 400 parts by weight of Radix Astragali.

17. The method of claim 16, characterized in that component (iv) is one or more materials selected from the group consisting of 10 to 60 parts by weight of Flos Rosae Rugosae, 10 to 120 parts by weight of Ganoderma spore powder, 10 to 60 parts by weight of Ganoderma spore oil, 20 to 200 parts by weight of Radix Pseudostellariae, 20 to 90 parts by weight of Folium Ginseng, 20 to 200 parts by weight of Radix Codonopsis, and 20 to 200 parts by weight of Radix Astragali.

18. The method of claim 17, characterized in that component (iv) is one or more materials selected from the group consisting of 30 parts by weight of Flos Rosae Rugosae, 30 parts by weight of Ganoderma spore powder, 20 parts by weight of Ganoderma spore oil, 40 parts by weight of Radix Pseudostellariae, 30 parts by weight of Folium Ginseng, 40 parts by weight of Radix Codonopsis, and 40 parts by weight of Radix Astragali.

* * * * *